United States Patent
Kim et al.

(10) Patent No.: US 11,142,559 B2
(45) Date of Patent: *Oct. 12, 2021

(54) GLUCAGON DERIVATIVE, CONJUGATE THEREOF, COMPOSITION COMPRISING SAME, AND THERAPEUTIC USE THEREOF

(71) Applicant: HANMI PHARM. CO., LTD, Hwaseong-si (KR)

(72) Inventors: Jung Kuk Kim, Hwaseong-si (KR); Young Jin Park, Hwaseong-si (KR); In Young Choi, Hwaseong-si (KR); Sung Youb Jung, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/233,890

(22) Filed: Dec. 27, 2018

(65) Prior Publication Data

US 2019/0119347 A1   Apr. 25, 2019

Related U.S. Application Data

(63) Continuation of application No. PCT/KR2017/006922, filed on Jun. 29, 2017.

(30) Foreign Application Priority Data

Jun. 29, 2016 (KR) .......................... 10-2016-0081995
Dec. 29, 2016 (KR) .......................... 10-2016-0182982
Jun. 2, 2017 (KR) .......................... 10-2017-0069217

(51) Int. Cl.
| | | |
|---|---|---|
| A61K 38/26 | (2006.01) | |
| C07K 14/605 | (2006.01) | |
| A61K 45/06 | (2006.01) | |
| A61K 38/28 | (2006.01) | |
| A61K 47/50 | (2017.01) | |
| A61K 38/17 | (2006.01) | |
| A61K 47/68 | (2017.01) | |
| A61K 47/60 | (2017.01) | |
| A61P 3/08 | (2006.01) | |
| A61P 3/04 | (2006.01) | |

(52) U.S. Cl.
CPC ............ *C07K 14/605* (2013.01); *A61K 38/17* (2013.01); *A61K 38/26* (2013.01); *A61K 38/28* (2013.01); *A61K 45/06* (2013.01); *A61K 47/50* (2017.08); *A61K 47/60* (2017.08); *A61K 47/6811* (2017.08); *A61P 3/04* (2018.01); *A61P 3/08* (2018.01)

(58) Field of Classification Search
None
See application file for complete search history.

(56) References Cited

U.S. PATENT DOCUMENTS

| | | | |
|---|---|---|---|
| 5,408,037 A | 4/1995 | Smith et al. | |
| 7,994,122 B2 | 8/2011 | Riber et al. | |
| 8,450,270 B2 | 5/2013 | Dimarchi et al. | |
| 8,454,971 B2 | 6/2013 | Day et al. | |
| 8,507,428 B2 | 8/2013 | DiMarchi et al. | |
| 8,703,701 B2 | 4/2014 | DiMarchi | |
| 2006/0275254 A1 | 12/2006 | Kim et al. | |
| 2009/0111739 A1 | 4/2009 | Kajihara et al. | |
| 2010/0105877 A1 | 4/2010 | Song et al. | |
| 2010/0190699 A1 | 7/2010 | Dimarchi et al. | |
| 2010/0190701 A1* | 7/2010 | Day ..................... | C07K 14/605 514/1.1 |
| 2010/0330108 A1* | 12/2010 | Song ................. | A61K 47/6835 424/179.1 |
| 2011/0082079 A1 | 4/2011 | Spetzler et al. | |
| 2012/0165503 A1 | 6/2012 | Carrington et al. | |
| 2012/0288511 A1 | 11/2012 | Dimarchi | |
| 2012/0329715 A1 | 12/2012 | Greig et al. | |
| 2013/0116173 A1 | 5/2013 | DiMarchi et al. | |
| 2013/0143798 A1 | 6/2013 | Lau et al. | |
| 2013/0203659 A1 | 8/2013 | Miranda et al. | |
| 2014/0011738 A1 | 1/2014 | DiMarchi | |
| 2014/0128318 A1 | 5/2014 | Jung et al. | |
| 2015/0164997 A1 | 6/2015 | Haack et al. | |
| 2015/0183847 A1 | 7/2015 | Qin | |
| 2015/0368310 A1 | 12/2015 | DiMarchi et al. | |
| 2018/0311315 A1 | 11/2018 | Oh et al. | |

FOREIGN PATENT DOCUMENTS

| | | |
|---|---|---|
| CN | 102892425 A | 1/2013 |
| CN | 103732618 A | 4/2014 |
| CO | NC2017/0006308 | 9/2017 |
| EA | 201791333 A1 | 12/2017 |
| EP | 3241841 A1 | 11/2017 |
| EP | 3354664 A1 | 8/2018 |
| JP | 10-2012-0052973 A | 5/2012 |
| JP | 2014-507402 A | 3/2014 |
| JP | 5476304 B2 | 4/2014 |

(Continued)

OTHER PUBLICATIONS

KR 10-2015-0093265 Jun. 30 2015 total of 62 pages. (Year: 2015).*
Translation of 10-2015-0093265, received Jun. 3, 2019, 30 pages (Year: 2019).*
Endocrine Abstracts (43rd Annual Meeting of the British Society for Paediatric Endocrinology and Diabetes, v39 Nov. 2015 total of 77 pages) (Year: 2015).*
Australian Patent Office; Communication dated Feb. 7, 2019 in Australian application No. 2017289014.

(Continued)

*Primary Examiner* — Ronald T Niebauer
(74) *Attorney, Agent, or Firm* — Sughrue Mion, PLLC

(57) ABSTRACT

The present invention relates to a glucagon derivative, a conjugate thereof, and a composition comprising the same, and a therapeutic use thereof, and in particular, for metabolic syndrome, hypoglycemia, and congenital hyperinsulinism.

22 Claims, 8 Drawing Sheets

Specification includes a Sequence Listing.

(56) References Cited

FOREIGN PATENT DOCUMENTS

| | | |
|---|---|---|
| JP | 2015-521622 A | 7/2015 |
| KR | 10-2009-0096498 A | 9/2009 |
| KR | 10-2009-0119876 A | 11/2009 |
| KR | 10-2012-0010146 A | 2/2012 |
| KR | 10-2012-0068755 A | 6/2012 |
| KR | 1020120139579 A | 12/2012 |
| KR | 10-2013-0018410 A | 2/2013 |
| KR | 10-2014-0018462 A | 2/2014 |
| KR | 10-1382593 B1 | 4/2014 |
| KR | 10-2015-0023013 A | 3/2015 |
| KR | 10-2015-0096398 A | 8/2015 |
| KR | 10-2015-0096433 A | 8/2015 |
| MA | 40709 A1 | 12/2017 |
| MA | 41887 A1 | 12/2018 |
| TW | 201307380 A | 2/2013 |
| TW | 201309323 A | 3/2013 |
| TW | 201607553 A | 3/2016 |
| TW | I713541 B | 12/2020 |
| WO | 96/16196 A2 | 5/1996 |
| WO | 96/16196 A3 | 5/1996 |
| WO | 96/32478 A1 | 10/1996 |
| WO | 97/34631 A1 | 9/1997 |
| WO | 97/43631 A1 | 9/1997 |
| WO | 0183527 A2 | 11/2001 |
| WO | 2004/093823 A2 | 11/2004 |
| WO | 2008101017 A2 | 8/2008 |
| WO | 2009099763 A1 | 8/2009 |
| WO | 2010/011439 A2 | 1/2010 |
| WO | 2010/096052 A1 | 8/2010 |
| WO | 2010148089 A1 | 12/2010 |
| WO | 2011038900 A2 | 4/2011 |
| WO | 2011/075393 A2 | 6/2011 |
| WO | 2011/088837 A1 | 7/2011 |
| WO | 2011/117415 A1 | 9/2011 |
| WO | 2011143208 A1 | 11/2011 |
| WO | 2012/011752 A2 | 1/2012 |
| WO | 2012/088116 A2 | 6/2012 |
| WO | 2012/158965 A2 | 11/2012 |
| WO | 2012150503 A2 | 11/2012 |
| WO | 2012/169798 A2 | 12/2012 |
| WO | 2012/173422 A1 | 12/2012 |
| WO | 2013/004983 A1 | 1/2013 |
| WO | 2013/074910 A1 | 5/2013 |
| WO | 2013/192129 A1 | 12/2013 |
| WO | 2013/192130 A1 | 12/2013 |
| WO | 2014/017843 A1 | 1/2014 |
| WO | 2014/017845 A2 | 1/2014 |
| WO | 2014049610 A2 | 4/2014 |
| WO | 2014/073842 A1 | 5/2014 |
| WO | 2014/073845 A1 | 5/2014 |
| WO | 2014/081864 A1 | 5/2014 |
| WO | 2014/081872 A1 | 5/2014 |
| WO | 2014/096145 A1 | 6/2014 |
| WO | 2014/096150 A1 | 6/2014 |
| WO | 2014/170496 A1 | 10/2014 |
| WO | 2015022420 A1 | 2/2015 |
| WO | 2015/095406 A1 | 6/2015 |
| WO | 2015/183054 A1 | 12/2015 |
| WO | 2016/043533 A1 | 3/2016 |
| WO | 2016/049190 A1 | 3/2016 |
| WO | 2016/108586 A1 | 7/2016 |
| WO | 2017/003191 A1 | 1/2017 |
| WO | 2017/095201 A1 | 6/2017 |

OTHER PUBLICATIONS

Ecuador Patent Office; Communication dated Feb. 3, 2019 in Ecuadorian application No. SENADI-2018-53055.
Ecuador Patent Office; Communication dated Feb. 3, 2019 in Ecuadorian application No. SENADI-2018-53053.
Brian Finan, et al., "A rationally designed monomeric peptide triagonist corrects obesity and diabetes in rodents", Nat Med., Jan. 2015, 1-13 pages, vol. 21, No. 1.
Daniel J. Drucker, et al., "The Incretin system: glucagon-like peptide-1 receptor agonists and dipeptidyl peptidase-4 inhibitors in type 2 diabetes", The Lancet, 2006, pp. 1696-1705, vol. 368, No. 11.
International Searching Authority; International Search Report for PCT/KR2016/015554 dated Apr. 10, 2017 [PCT/ISA/210].
International Searching Authority; International Search Report for PCT/KR2016/015555 dated Apr. 10, 2017 [PCT/ISA/210].
Jonathan W. Day, et al., "A new glucagon and GLP-1 co-agonist eliminates obesity in rodents", Nature Chemical Biology, Oct. 2009, pp. 749-757, vol. 5, No. 10.
Korean Intellectual Property Office, Communication dated Jul. 11, 2018, issued in Korean Application No. 10-2016-0183500.
Korean Intellectual Property Office, Communication dated Jul. 11, 2018, issued in Korean Application No. 10-2016-0183499.
Yahiya Y. Syed, et al., "Exenatide Extended-Release: An Updated Review of Its Use in Type 2 Diabetes Mellitus", Drugs, Jun. 2015, 12 pages, vol. 10.
Australian Patent Office; Communication dated Jul. 31, 2018 in application No. 2016382393.
Australian Patent Office; Communication dated Jul. 31, 2018 in application No. 2016382394.
Ecuador Patent Office; Communication dated Feb. 3, 2018 in application No. IEPI-2018-3879.
United States Patent and Trademark Office; Communication dated Feb. 27, 2019, issued in U.S. Appl. No. 16/023,994.
United States Patent and Trademark Office; Communication dated Jan. 11, 2019 in counterpart U.S. Appl. No. 16/024,014.
United States Patent and Trademark Office; Communication dated Oct. 31, 2018, issued in U.S. Appl. No. 16/024,014.
"Calculating approximate isoelectric points for amino acids and peptides", Nov. 1, 2011, pp. 1-2, XP055471990, Retrieved from the Internet: URL:http://www.elcamino.edu/faculty/pdoucette/calculating-approximate-isoelectric-points.pdf (2 pages total).
Colombia Patent Office; Communication dated Jul. 17, 2018 in application No. NC2017/0006308.
European Patent Office; Communication dated Jun. 12, 2018 in application No. 15875680.9.
United States Patent and Trademark; Communication dated May 2, 2019, issued in U.S. Appl. No. 15/540,729.
"The Isoelectric Point", Chapter 23.4, Chemistry LibreTexts, Jul. 29, 2014 (13 pages total).
Perfetti, et al., "Glucagon-like peptide-1: a major regulator of pancreatic β-cell function", European Journal of Endocrinology, 2000, vol. 143, pp. 717-725 (9 pages total).
Gutniak, et al., "Antidiabetogenic Effect of Glucagon-Like Peptide-I (7-36)Amide in Normal Subjects and Patients With Diabetes Mellitus", The New England Journal of Medicine, May 14, 1992, pp. 1316-1322 (7 pages total).
John Eng et al., "Isolation and Characterization of Exendin-4, an Exendin-3 Analogue, from Heloderma suspectum Venom," The Journal of Biological Chemistry, Apr. 15, 1992, pp. 7402-7405, vol. 267, No. 11.
Joseph Chabenne et al., "A glucagon analog chemically stabilized for immediate treatment of life-threatening hypoglycemia," Molecular Metabolism, Jan. 2014, pp. 293-300, vol. 3.
Kevin L. Shaw et al., "The effect of net charge on the solubility, activity, and stability of ribonuclease SA," Protein Science, 2001, pp. 1206-1215, vol. 10.
International Search Report of PCT/KR2015/014422 dated Apr. 14, 2016.
Columbia Patent Office; Communication dated Jul. 17, 2018 in counterpart application No. NC2017/0006308.
Supplementary Partial European Search Report of EP 15 87 5680 dated May 8, 2018.
Anonymous, "Calculating approximate isoelectric points for amino acids and peptides", Nov. 1, 2011, pp. 1-2, XP055471990, Retrieved from the Internet: URL:http://www.elcamino.edu/faculty/pdoucette/calculating-approximate-isoelectric-points.pdf (2 pages total).
Korean Intellectual Property Office; Communication dated Jul. 12, 2018 in counterpart application No. 10-2016-0081976.
Elisabeth Gasteiger et al., "ExPASy: the proteomics server for in-depth protein knowledge and analysis," Nucleic Acids Research, 2003, pp. 3784-3788. vol. 31, No. 13, 2003.

(56) References Cited

OTHER PUBLICATIONS

International Search Report for PCT/KR2016/006984, dated Sep. 12, 2016 (PSA/ISA/210).
Written Opinion of the International Searching Authority for PCT/KR2016/006984, dated Sep. 12, 2016 (PCT/ISA/237).
International Search Report for PCT/KR2017/006922, dated Dec. 7, 2017.
United States Patent and Trademark Office; Communication dated Sep. 9, 2019, issued in U.S. Appl. No. 15/740,668.
Biosynthesis, "N-Terminal Acetylation Amidation Peptides Chemically Synthesized Aminopeptidases Intracellular", Nov. 11, 2008, URL biosyn.com/faq/why-acetylate-and-amidate-a-peptide.aspx (1 page total).
Unson et al., "The Role of Histidine-1 in Glucagon Action", Archives of Biochemistry and Biophysics, Feb. 1, 1993, vol. 300, No. 2, pp. 747-750 (total 5 pages).
Krstenansky et al., "Examination of the Conformational Requirements Glucagon at its Receptor", Peptides Structure and Function, Proceedings of the Ninth American Peptide Symposium, 1985. pp. 591-594 (total 8 pages).
Cornier et al., "The Metabolic Syndrome", Endocrine Reviews, 2008, vol. 29, No. 7, pp. 777-822 (total 46 pages).
Santoprete et al., "DPP-IV-resistant, long-acting oxyntomodulin derivatives", Journal of Peptide Science, vol. 17, No. 4, Apr. 1, 2011, pp. 270-280, XP055000397.
Chabenne et al., "Optimization of the Native Glucagon Sequence for Medicinal Purposes", Journal of Diabetes Science and Technology, vol. 4, Issue 6, Nov. 2010 (10 pages total).
Holz et al., "Glucagon-Like Peptide-1 Synthetic Analogs: New Therapeutic Agents for Use in the Treatment of Diabetes Mellitus", Current Medicinal Chemistry, vol. 10, 2003, pp. 2471-2483.
Knudsen et al., "Potent Derivatives of Glucagon-like Peptide-1 with Pharmacokinetic Properties Suitable for Once Daily Administration," J. Med. Chem., vol. 43, 2000, pp. 1664-1669.
Huang et al., "Characterization of Poly(ethylene glycol) and PEGylated Products by LC/MS with Postcolumn Addition of Amines", Anal. Chem., 2009, vol. 81, pp. 567-577 (11 pages total).
Stigsnaes et al., "Characterisation and physical stability of PEGylated glucagon", International Journal of Pharmaceutics, 2007, vol. 330, pp. 89-98 (10 pages total).
Lee et al., "PEGylated glucagon-like peptide-1 displays preserved effects on insulin release in isolated pancreatic islets and improved biological activity in db/db mice", Diabetologia, 2006, vol. 49, pp. 1608-1611.
Oka et al., "Endogenous GLP-1 is involved in β-amyloid protein-induced memory impairment and hippocampal neuronal death in rats", Brain Research, 2000, vol. 878, pp. 194-198 (5 pages total).
Suzuki E et al., "A Role of Endogenous GLP-1 in Amnesia and Neuronal Death Induced By Continuous I.C.V. Infusion of Beta-Amyloid Protein in Rat", Japanese Journal of Pharmacology, the Japanese Pharmacological Society, Kyoto, JP, (2000), vol. 82, No. SUPPL 1, p. 236P.

\* cited by examiner

[FIG. 1]
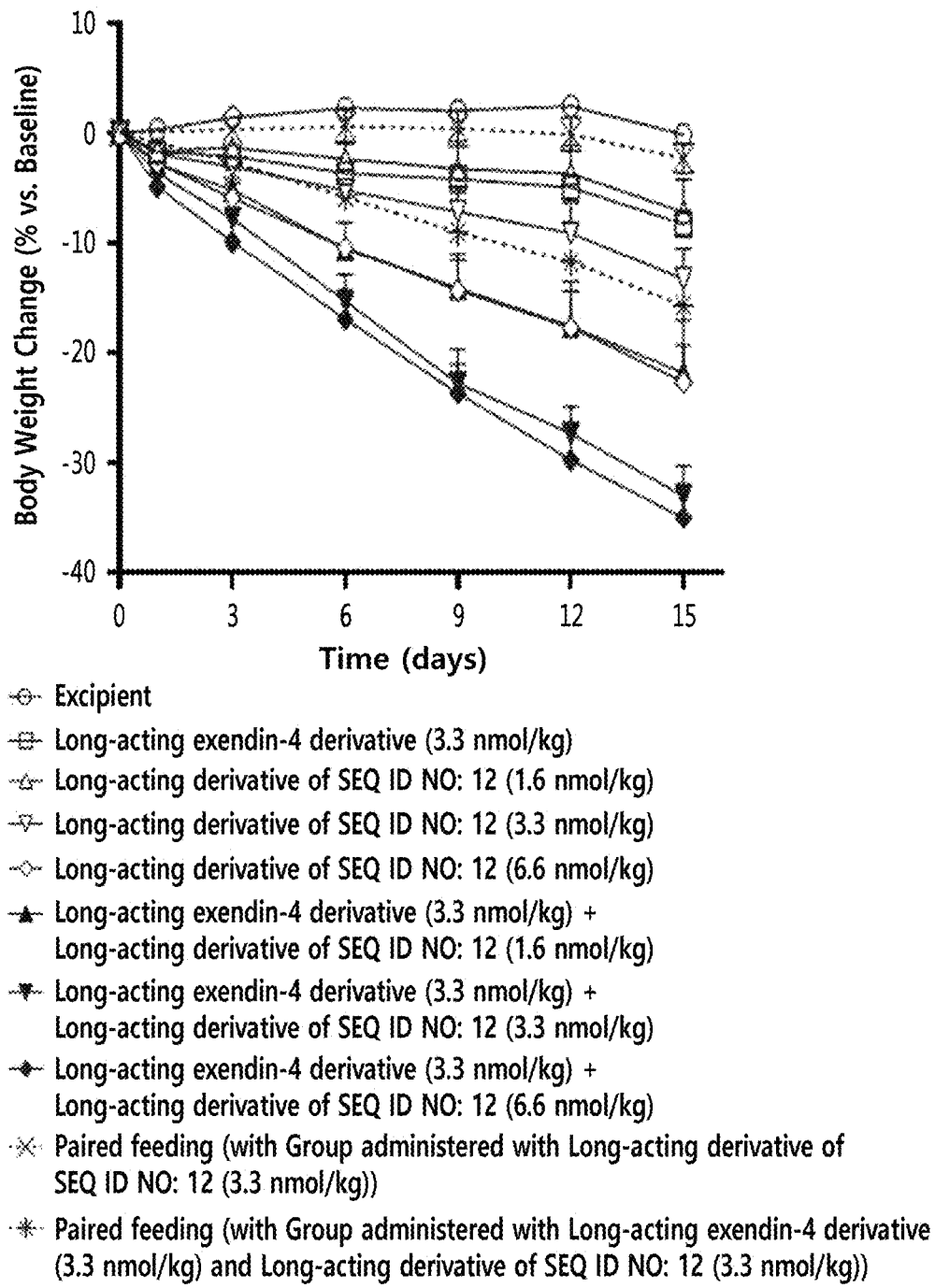

[FIG. 2]

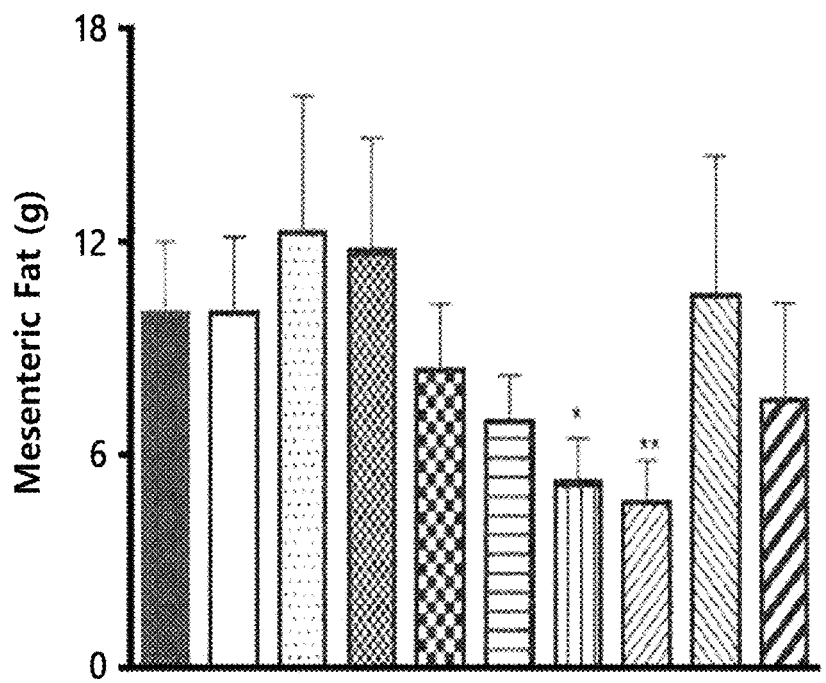

▓ Excipient
☐ Long-acting exendin-4 derivative (3.3 nmol/kg)
▦ Long-acting derivative of SEQ ID NO: 12 (1.6 nmol/kg)
▦ Long-acting derivative of SEQ ID NO: 12 (3.3 nmol/kg)
▦ Long-acting derivative of SEQ ID NO: 12 (6.6 nmol/kg)
▭ Long-acting exendin-4 derivative (3.3 nmol/kg) +
  Long-acting derivative of SEQ ID NO: 12 (1.6 nmol/kg)
▦ Long-acting exendin-4 derivative (3.3 nmol/kg) +
  Long-acting derivative of SEQ ID NO: 12 (3.3 nmol/kg)
▨ Long-acting exendin-4 derivative (3.3 nmol/kg) +
  Long-acting derivative of SEQ ID NO: 12 (6.6 nmol/kg)
▨ Paired feeding (with Group administered with Long-acting derivative of
  SEQ ID NO: 12 (3.3 nmol/kg))
▨ Paired feeding (with Group administered with Long-acting exendin-4 derivative
  (3.3 nmol/kg) and Long-acting derivative of SEQ ID NO: 12 (3.3 nmol/kg))

[FIG. 3]

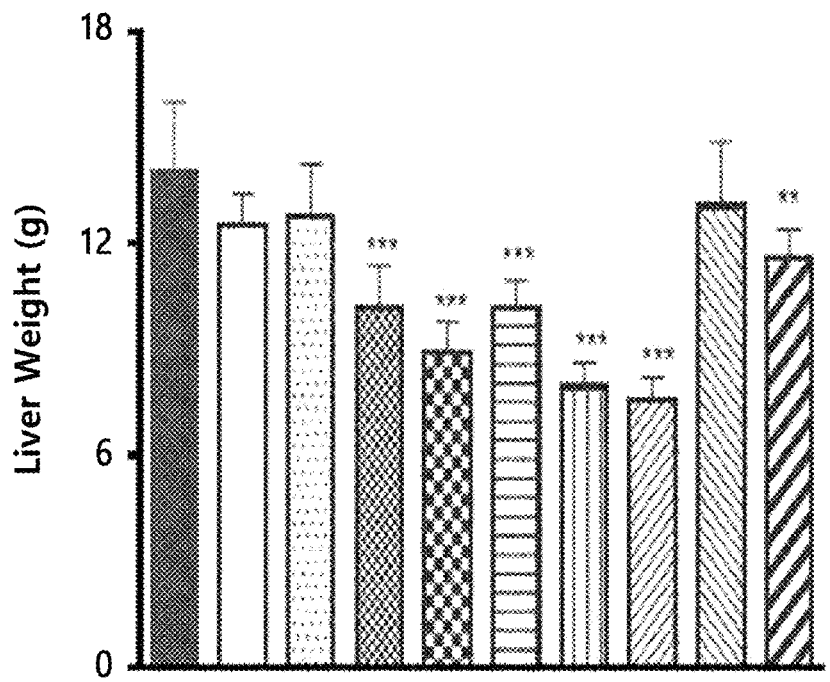

▓ Excipient
☐ Long-acting exendin-4 derivative (3.3 nmol/kg)
▒ Long-acting derivative of SEQ ID NO: 12 (1.6 nmol/kg)
▓ Long-acting derivative of SEQ ID NO: 12 (3.3 nmol/kg)
▓ Long-acting derivative of SEQ ID NO: 12 (6.6 nmol/kg)
☐ Long-acting exendin-4 derivative (3.3 nmol/kg) +
   Long-acting derivative of SEQ ID NO: 12 (1.6 nmol/kg)
▓ Long-acting exendin-4 derivative (3.3 nmol/kg) +
   Long-acting derivative of SEQ ID NO: 12 (3.3 nmol/kg)
▓ Long-acting exendin-4 derivative (3.3 nmol/kg) +
   Long-acting derivative of SEQ ID NO: 12 (6.6 nmol/kg)
▓ Paired feeding (with Group administered with Long-acting derivative of
   SEQ ID NO: 12 (3.3 nmol/kg))
▓ Paired feeding (with Group administered with Long-acting exendin-4 derivative
   (3.3 nmol/kg) and Long-acting derivative of SEQ ID NO: 12 (3.3 nmol/kg))

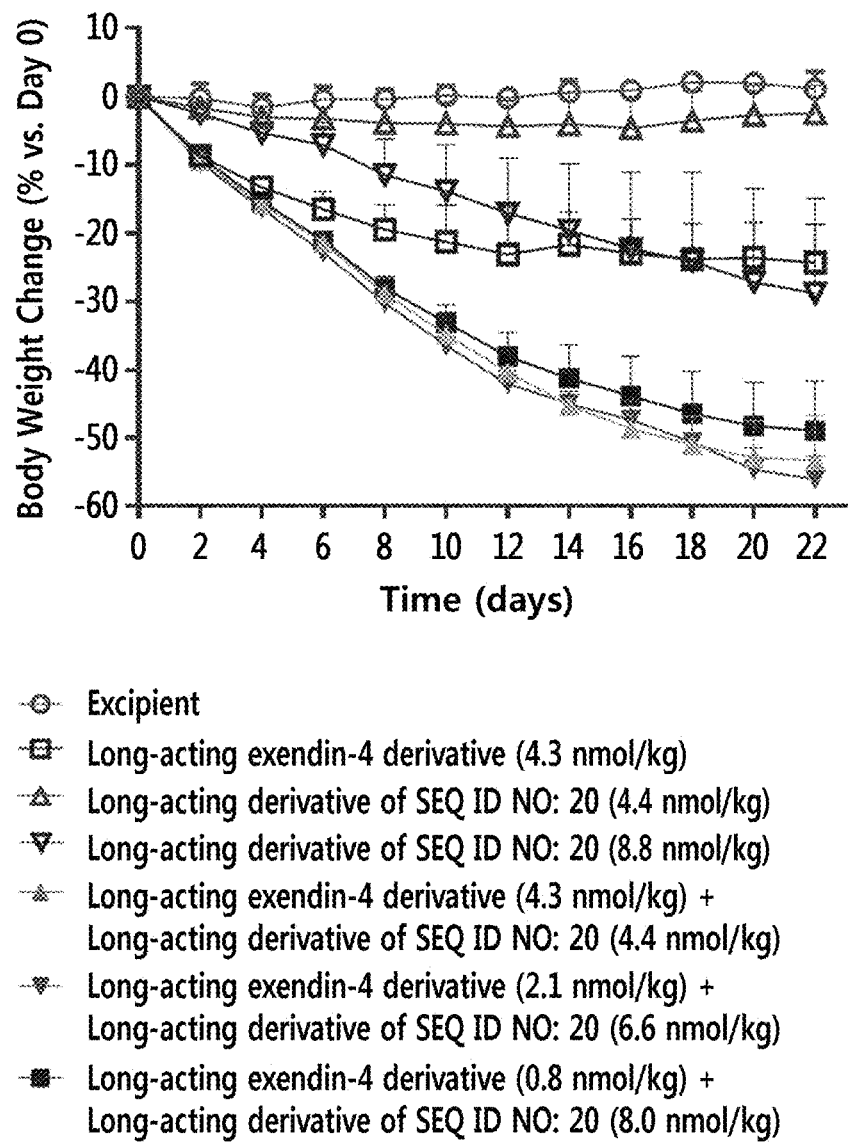

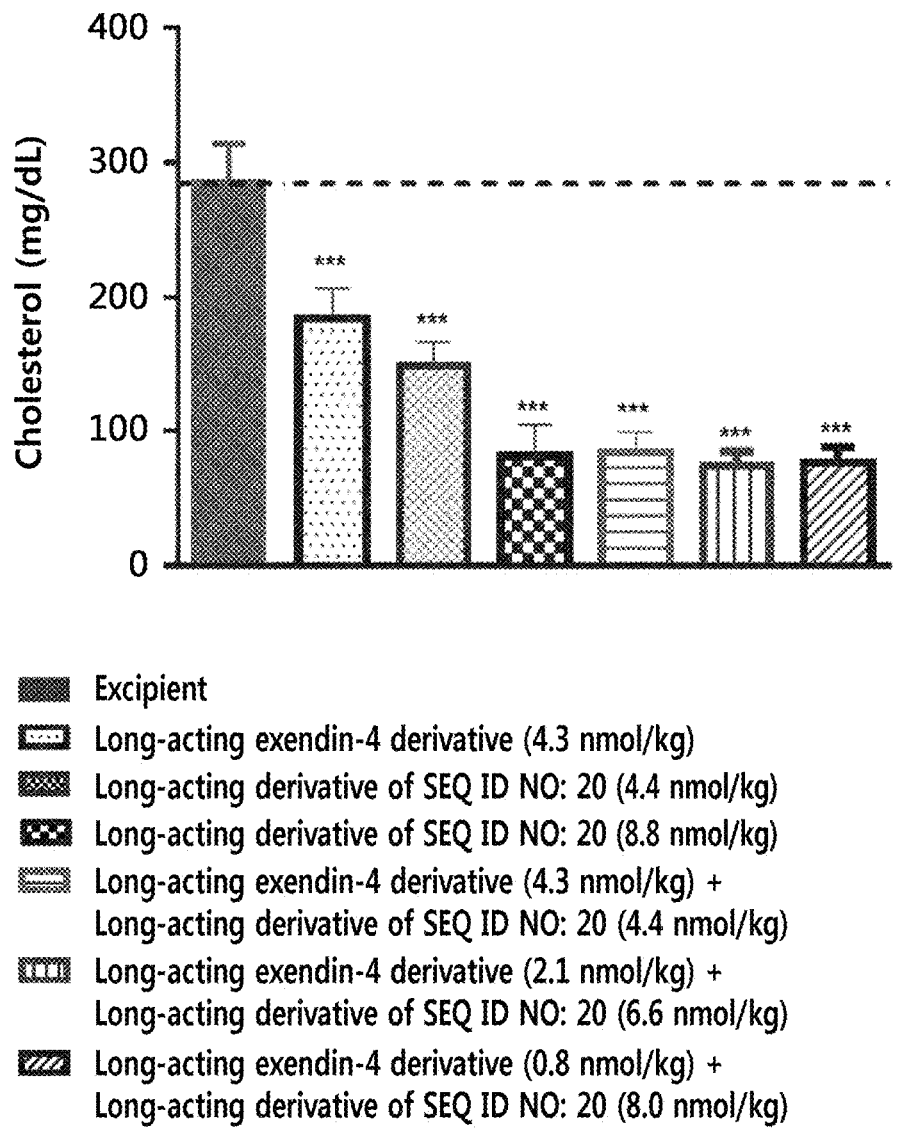

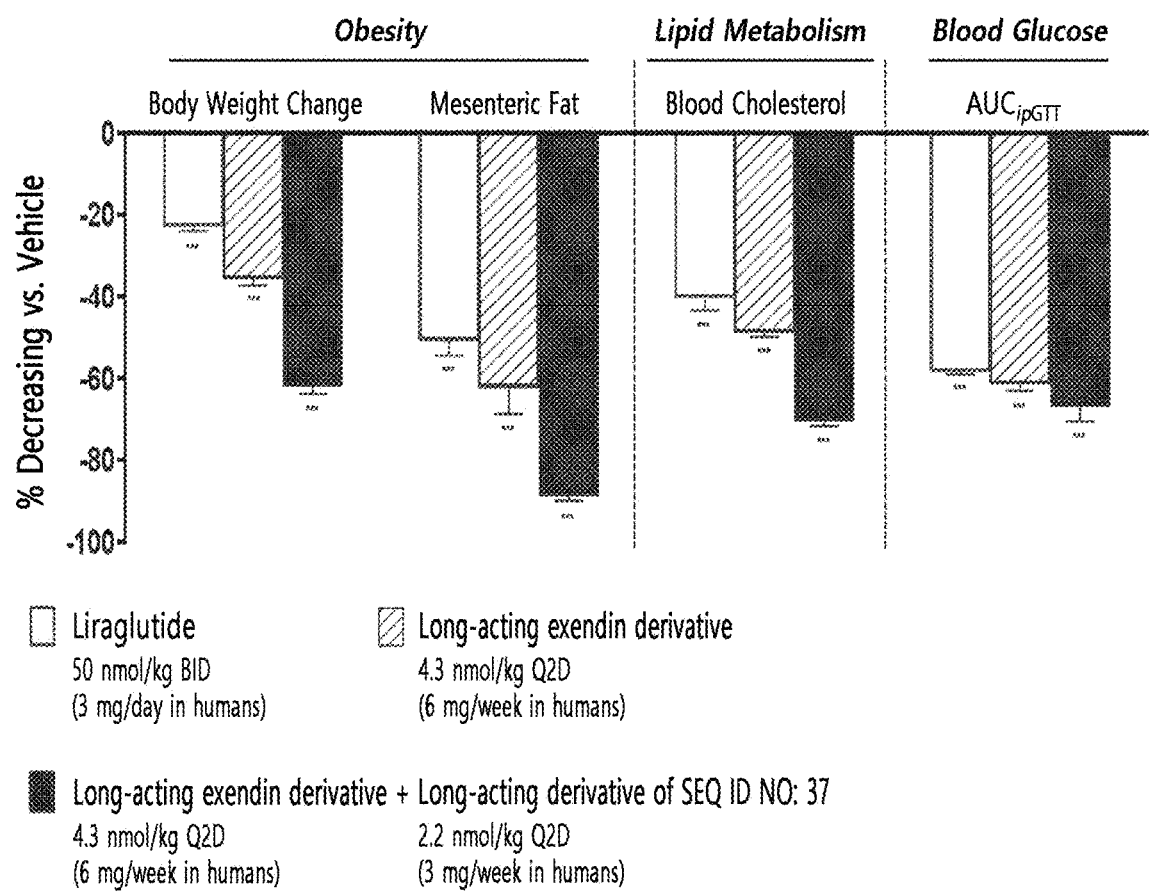
[FIG. 6]

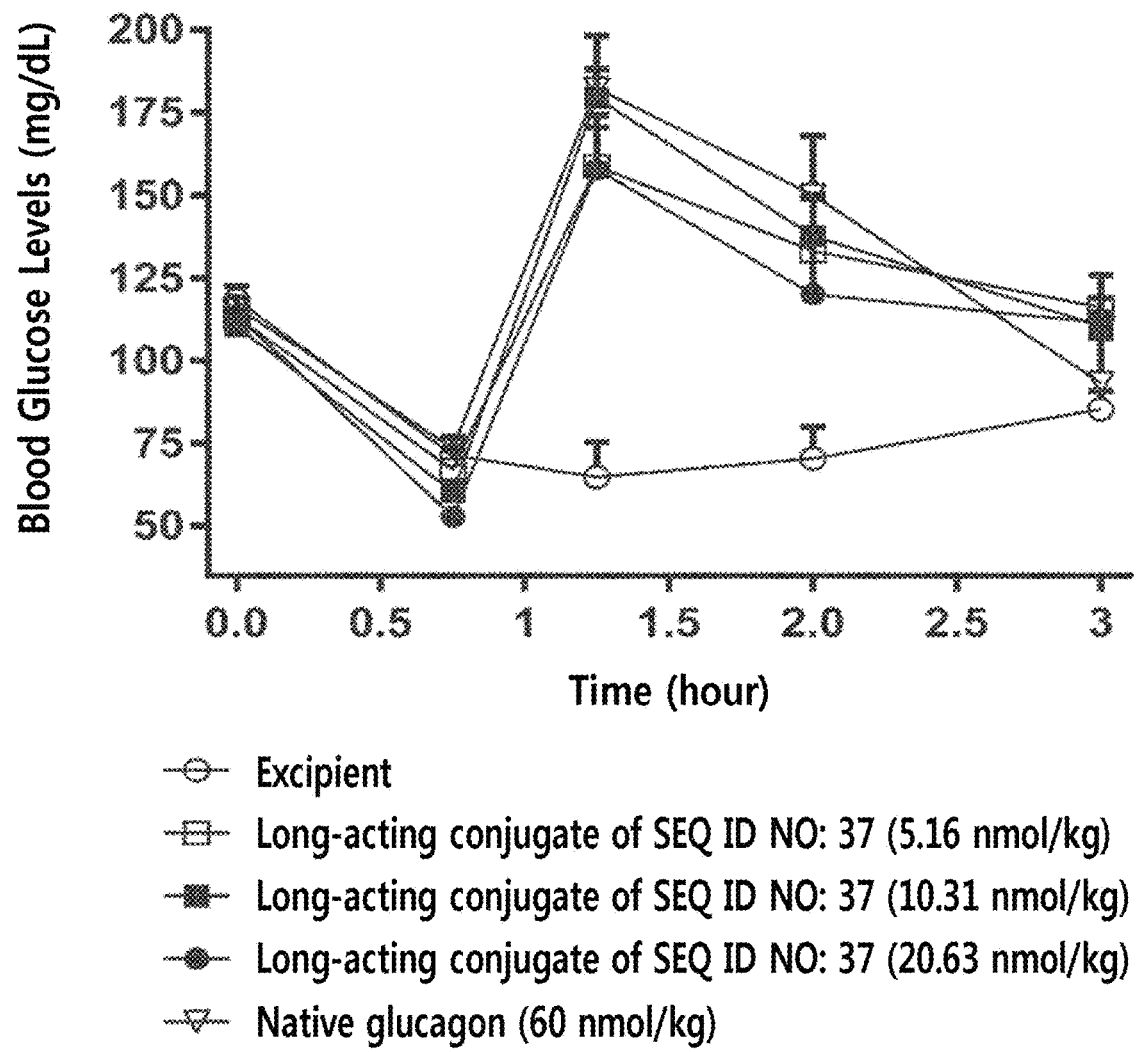
[FIG. 7]

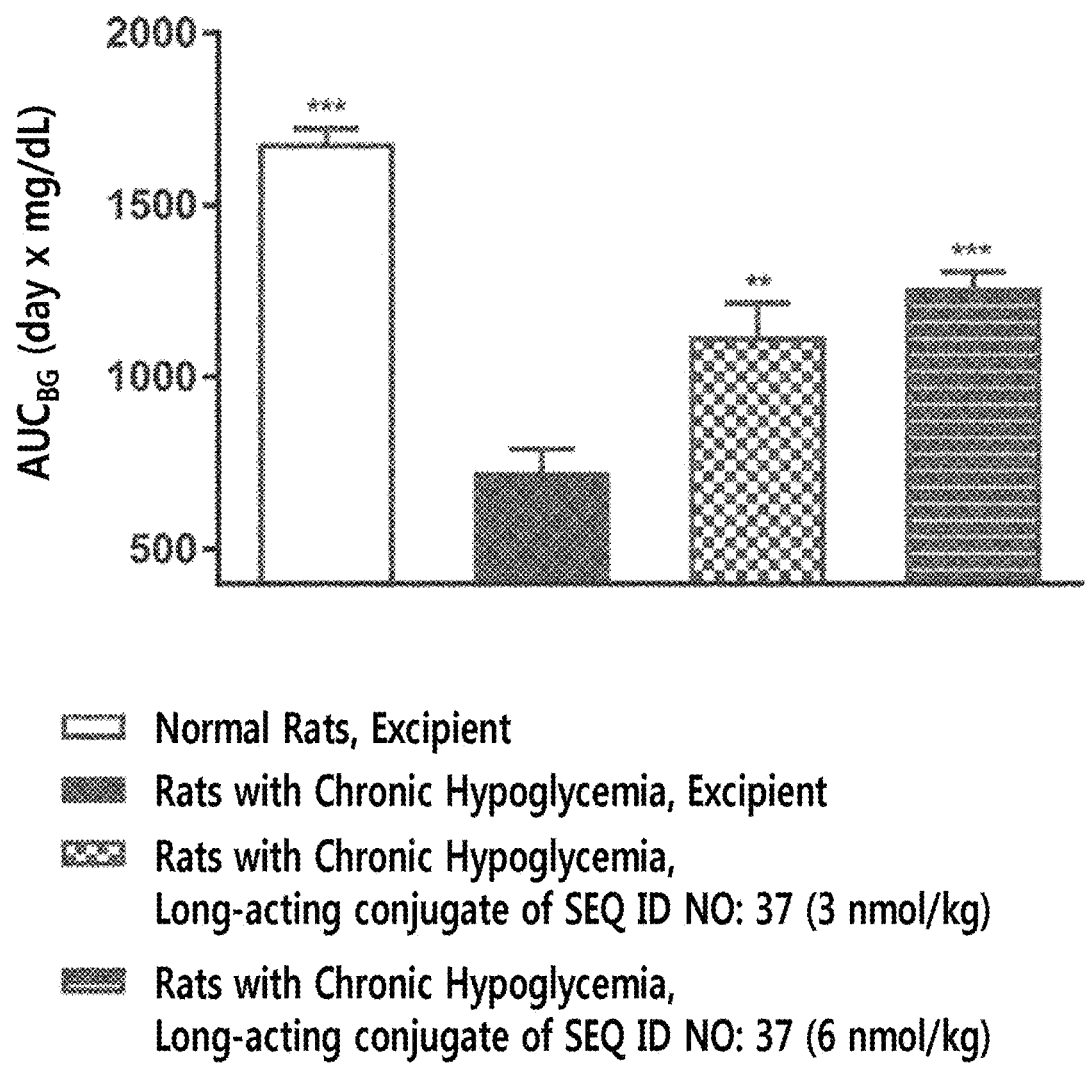
[FIG. 8]

GLUCAGON DERIVATIVE, CONJUGATE THEREOF, COMPOSITION COMPRISING SAME, AND THERAPEUTIC USE THEREOF

CROSS REFERENCE TO RELATED APPLICATIONS

This application is a Bypass Continuation of International Application No. PCT/KR2017/006922 filed Jun. 29, 2017, claiming priority based on Korean Patent Application No. 10-2016-0081995 filed Jun. 29, 2016, 10-2016-0182982 filed Dec. 29, 2016 and 10-2017-0069217 filed Jun. 6, 2017.

TECHNICAL FIELD

The present invention relates to a glucagon derivative, a conjugate thereof, and a composition containing the same, and a use thereof, in particular, a therapeutic use for metabolic syndrome, hypoglycemia, and congenital hyperinsulinism thereof.

BACKGROUND ART

Due to recent economic growth and changes in dietary habits, etc., the incidence of metabolic syndrome-associated diseases including various diseases such as obesity, hyperlipidemia, hypertension, arteriosclerosis, hyperinsulinemia, diabetes, and liver diseases is rapidly increasing. These diseases may occur independently but in general they mostly occur in a close relationship with each other, being accompanied by various symptoms.

Overweight and obesity are responsible for increasing blood pressure and cholesterol levels and causing or worsening various diseases, such as cardiac diseases, diabetes, arthritis, etc. In addition, the problem of obesity is also becoming a major cause in the increased incidence of arteriosclerosis, hypertension, hyperlipidemia, or heart diseases in children or teenagers as well as in adults.

However, obesity is not easy to treat, because it is a complex disease associated with the mechanisms of appetite control and energy metabolism. Accordingly, the treatment of obesity requires not only the efforts of obese patients, but also a method capable of treating abnormal mechanisms associated with appetite control and energy metabolism. Thus, efforts have been made to develop drugs for treating the abnormal mechanisms.

As a result of these efforts, drugs such as Rimonabant® (Sanofi-Aventis), Sibutramin® (Abbott), Contrave® (Takeda), Orlistat® (Roche), etc. have been developed, but they have the disadvantages of serious adverse effects or very weak anti-obesity effects. For example, according to a report, Rimonabant® shows a side-effect of central nervous system disorder, Sibutramine® and Contrave® show cardiovascular side-effects, and Orlistat® shows only about 4 kg of weight loss when taken for one year.

Meanwhile, glucagon is produced by the pancreas when blood glucose levels drop as a result of other medications or diseases, or hormone or enzyme deficiencies. Glucagon sends a signal for glycogen breakdown in the liver and a subsequent glucose release and plays a role in increasing blood glucose levels to a normal range. Additionally, glucagon has been shown to be effective in treating hypoglycemia. The hypoglycemic therapeutic effect of glucagon is the result of stimulating the degradation of glycogen to glucose (glycogen breakdown) or increasing glucose production (glucose biosynthesis) derived from amino acid precursors resulting in increased glucose outflow from the liver.

In addition to the effect of increasing the blood glucose levels, glucagon suppresses appetite and activates hormone-sensitive lipase of adipocytes to facilitate lipolysis, thereby showing an anti-obesity effect. However, the use of glucagon as a therapeutic agent has been limited because it has a low solubility and it is precipitated at a neutral pH.

Accordingly, the glucagon with improved properties alone can be effectively used for the treatment of severe hypoglycemia, nonalcoholic steatohepatitis (NASH), dyslipidemia, etc. due to its activities of fat decomposition and β-oxidation in the liver.

One of the glucagon derivatives, glucagon-like peptide-1 (GLP-1), is under development as a therapeutic agent for treating hyperglycemia in patients with diabetes, GLP-1 has the functions of stimulating insulin synthesis and secretion, inhibiting glucagon secretion, slowing gastric emptying, increasing glucose utilization, and inhibiting food intake.

Exendin-4, prepared from lizard venom and having an amino acid homology of about 50% with GLP-1, was also reported to activate the GLP-1 receptor, thereby improving hyperglycemia in patients with diabetes (*J Biol Chem.* 1992 Apr. 15; 267 (11): 7402-5). However, anti-obesity drugs containing GLP-1 are reported to show side-effects such as vomiting and nausea.

As an alternative to GLP-1, therefore, much attention has been focused on oxyntomodulin, which can bind to both receptors of the two peptides, GLP-1 and glucagon. Oxyntomodulin is a peptide prepared from a glucagon precursor, pre-glucagon, and has the functions of inhibiting food intake and enhancing satiety of GLP-1, and has lipolytic activity like glucagon, thus increasing its potency in anti-obesity therapy.

However, oxyntomodulin or derivatives thereof have a serious drawback in that an excess amount of the drug should be administered daily because they have low efficacy and a short in vivo half-life. Additionally, when both activities of GLP-1 and glucagon are present in a single peptide, the activity ratio thereof becomes fixed, and thus it is difficult to use a dual agonist with various ratios. Accordingly, a combined therapy capable of using various activity ratios by adjusting the contents of GLP-1 and glucagon may be more effective. However, for the combined therapy, it is required to improve the physical characteristics of glucagon, which aggregates at a neutral pH and precipitates with time, thus showing poor solubility.

Meanwhile, congenital hyperinsulinism is one of the most common causes of severe and persistent hypoglycemia in newborns and children. Insulin is a hormone that regulates blood glucose in the human body. It plays a role in lowering blood glucose levels when blood glucose level rises due to food intake, etc. However, in congenital hyperinsulinism, insulin does not play such a role and the pancreas secretes insulin regardless of blood glucose levels. As a result, the patients become hypoglycemic.

When hypoglycemia occurs, the levels of glucose, ketone, lactose, etc., which the brain cells mostly utilize, cannot be maintained and the energy supply from proteins and fats in the body is blocked, resulting in damage to brain cells and thereby causing seizures, learning disorders, cerebral palsy, blindness, and even death in severe cases.

Hypoglycemia may occur temporarily due to excessive insulin secretion. Additionally, hypoglycemia also occurs in infants who have undergone fetal distress. Although the cause of insulin secretion is unclear, in this case, hypoglycemia can be improved within days to months. Infants born to mothers with diabetes mellitus may have transient hypoglycemia if the sugar level is not well-controlled, but it does not recur if the feeding proceeds well and hypoglycemia disappears. Another cause is persistent hyperinsulinism due to several genetic defects. Reportedly, the causes of hyperinsulinism due to genetic defects include a mutation of SUR gene or Kir6.2 gene on the 11p15.1 chromosome or mutation of the glucokinase (GK) gene on the 7p15-p13 chromosome, increase of GK activity, which increases GK activity, and a mutation of the glutamate dehydrogenase (GDH) gene, which activates GDH and thereby increases the ATP in beta-islet cells, etc.

Accordingly, immediate treatment of hypoglycemia is important for preventing brain damage. Hypoglycemia may be treated by drinking a carbohydrate-containing beverage, but in a severe case, glucose or glucagon injection into the vein is essential. The goal of the treatment is to allow children to manage a normal dietary cycle with a safety device. For example, in the case of one-year-old infants, they may be allowed to stay fasted for at least 14 hours to 15 hours with medication because they sleep without eating for 10 hours to 12 hours at night.

Examples of the drugs to be used may include diazoxide, octreotide, glucagon, etc. Diazoxide is administered orally two or three times a day. Diazoxide inhibits insulin secretion by acting on ATP dependent $K^+$ (KATP) channel and thus it may be effective for the treatment of GK hyperinsulinism or GDH hyperinsulinism, but it is often unresponsive in autosomal recessive hyperinsulinism caused by a defect in the KATP pathway. Octreotide is administered by subcutaneous injection. When octreotide is administered, the effect of octreotide is initially exhibited, but sometimes its effect decreases after a period of time. Glucagon promotes glucose release from the liver and is administered by subcutaneous or intravenous injection, which is known to be used when an oral administration is not available in an emergency situation.

Among these, glucagon is currently used as a lyophilized formulation due to its low solubility and precipitation at neutral pH, which is inconvenient because it is to be dissolved in a solvent before use. Furthermore, when glucagon is used as a therapeutic agent for the treatment of congenital hyperinsulinism, which requires long-term treatment due to its short half-life, the use of glucagon has been limited due to frequent administration.

DISCLOSURE

Technical Problem

An object of the present invention is to provide a composition containing a glucagon derivative or a conjugate containing the same, and specifically, a pharmaceutical composition for preventing or treating congenital hyperinsulinism, hypoglycemia, or metabolic syndrome containing a glucagon derivative or a conjugate containing the same.

Another object of the present invention is to provide a glucagon derivative.

Still another object of the present invention is to provide an isolated polynucleotide encoding a glucagon derivative, a vector including the polynucleotide, and an isolated cell including the polynucleotide or the vector.

Still another object of the present invention is to provide an isolated conjugate which includes a peptide moiety and a biocompatible material moietywhich is covalently linked to the peptide moiety. Still another object of the present invention is to provide a kit contatining a glucagon derivative or a conjugate containing the same, and specifically, a kit for preventing or treating congenital hyperinsulinism, hypoglycemia, or metabolic syndrome contatining a glucagon derivative or a conjugate containing the same.

Still another object of the present invention is to provide a method for preventing or treating congenital hyperinsulinism including administering the glucagon derivative or an isolated conjugate containing the same or a composition containing the same to a subject in need thereof.

Still another object of the present invention is to provide use of the glucagon derivative or an isolated conjugate containing the same or a composition containing the same in the preparation of a medicament for preventing or treating congenital hyperinsulinism.

Still another object of the present invention is to provide a method for preventing or treating hypoglycemia including administering the glucagon derivative or an isolated conjugate containing the same or a composition containing the same to a subject in need thereof.

Still another object of the present invention is to provide use of the glucagon derivative or an isolated conjugate containing the same or a composition containing the same in the preparation of a medicament for preventing or treating hypoglycemia.

Still another object of the present invention is to provide a method for preventing or treating metabolic syndrome including administering a glucagon derivative or an isolated conjugate or a composition containing the same to a subject in need thereof.

Still another object of the present invention is to provide use of the glucagon derivative or an isolated conjugate containing the same or the composition containing the same in the preparation of a medicament (or a pharmaceutical composition) for preventing or treating metabolic syndrome.

Technical Solution

An aspect of the present invention provides a composition containing a glucagon derivative or a conjugate containing the same, and specifically, a pharmaceutical composition for preventing or treating congenital hyperinsulinism, hypoglycemia, or metabolic syndrome containing a glucagon derivative or a conjugate containing the same.

In a specific embodiment, the present invention relates to a composition containing a glucagon derivative peptide including the amino acid sequence of the following General Formula 1, and specifically, a pharmaceutical composition for preventing or treating congenital hyperinsulinism, hypoglycemia, or metabolic syndrome containing a glucagon derivative peptide including the amino acid sequence of the following General Formula 1:

(General Formula 1, SEQ ID NO: 45)
X1-X2-QGTF-X7-SD-X10-S-X12-X13-X14-X15-X16-X17-
X18-X19-X20-X21-F-X23-X24-W-L-X27-X28-X29-X30 wherein, in General Formula 1,

X1 is histidine (H), desamino-histidyl, N-dimethyl-histidyl, β-hydroxy imidazopropionyl, 4-imidazoacetyl, β-carboxy imidazopropionyl, tryptophan (W), or tyrosine (Y), or is absent;

X2 is α-methyl-glutamic acid, aminoisobutyric acid (Aib), D-alanine, glycine (G), Sar (N-methylglycine), serine (S), or D-serine;

X7 is threonine (T), valine (V), or cysteine (C);

X10 is tyrosine (Y) or cysteine (C);

X12 is lysine (K) or cysteine (C);

X13 is tyrosine (Y) or cysteine (C);

X14 is leucine (L) or cysteine (C);

X15 is aspartic acid (D), glutamic acid (E), or cysteine (C);

X16 is glutamic acid (E), aspartic acid (D), serine (S), α-methyl-glutamic acid, or cysteine (C), or is absent;

X17 is aspartic acid (D), glutamine (Q), glutamic acid (E), lysine (K), arginine (R), serine (S), cysteine (C), or valine (V), or is absent;

X18 is alanine (A), aspartic acid (D), glutamic acid (E), arginine (R), valine, or cysteine (C), or is absent;

X19 is alanine (A), arginine (R), serine (S), valine (V), or cysteine (C), or is absent;

X20 is lysine (K), histidine (H), glutamine (Q), aspartic acid (D), arginine (R), α-methyl-glutamic acid, or cysteine (C), or is absent;

X21 is aspartic acid (D), glutamic acid (E), leucine (L), valine (V), or cysteine (C), or is absent;

X23 is isoleucine (I), valine (V), or arginine (R), or is absent;

X24 is valine (V), arginine (R), alanine (A), cysteine (C), glutamic acid (E), lysine (K), glutamine (Q), α-methyl-glutamic acid, or leucine (L), or is absent;

X27 is isoleucine (I), valine (V), alanine (A), lysine (K), methionine (M), glutamine (Q), or arginine (R), or is absent;

X28 is glutamine (Q), lysine (K), asparagine (N), or arginine (R), or is absent;

X29 is lysine (K), alanine (A), glycine (G), or threonine (I), or is absent; and X30 is cysteine (C), or is absent;

with the proviso that when the amino acid sequence of General Formula 1 is identical to SEQ ID NO: 1, it is excluded.

The following are additional specific embodiments of the present invention.

Specifically, as a pharmaceutical composition according to the previous specific embodiment:
in General Formula 1,
X1 is histidine (H), tryptophan (W), or tyrosine (Y), or is absent;
X2 is serine (S) or aminoisobutyric acid (Aib);
X7 is threonine (T), valine (V), or cysteine (C);
X10 is tyrosine (Y) or cysteine (C);
X12 is lysine (K) or cysteine (C);
X13 is tyrosine (Y) or cysteine (C);
X14 is leucine (L) or cysteine (C);
X15 is aspartic acid (D) or cysteine (C);
X16 is glutamic acid (E), serine (S), or cysteine (C);
X17 is aspartic acid (D), glutamic acid (E), lysine (K), arginine (R), serine (S), cysteine (C), or valine (V);
X18 is aspartic acid (D), glutamic acid (E), arginine (R), or cysteine (C);
X19 is alanine (A) or cysteine (C);
X20 is glutamine (Q), aspartic acid (D), lysine (K), or cysteine (C);
X21 is aspartic acid (D), glutamic acid (E), leucine (L), valine (V), or cysteine (C);
X23 is isoleucine (I), valine (V), or arginine (R);
X24 is valine (V), arginine (R), alanine (A), glutamic acid (E), lysine (K), glutamine (Q), or leucine (L);
X27 is isoleucine (I), valine (V), alanine (A), methionine (M), glutamine (Q), or arginine (R);
X28 is glutamine (Q), lysine (K), asparagine or arginine (R);
X29 is threonine (T); and
X30 is cysteine (C) or is absent.

As the pharmaceutical composition according to any one of the previous specific embodiments:
in General Formula 1,
X1 is histidine (H), tryptophan (W), or tyrosine (Y);
X2 is serine (S) or aminoisobutyric acid (Aib);
X7 is cysteine (C), threonine (T), or valine (V);
X10 is tyrosine (Y) or cysteine (C);
X12 is lysine (K) or cysteine (C);
X13 is tyrosine (Y) or cysteine (C);
X14 is leucine (L) or cysteine (C);
X15 is aspartic acid (D) or cysteine (C);
X16 is glutamic acid (F), serine (S), or cysteine (C);
X17 is glutamic acid (E), lysine (K), arginine (R), cysteine (C), or valine (V);
X18 is arginine (R) or cysteine (C);
X19 is alanine (A) or cysteine (C);
X20 is glutamine (Q) or lysine (K);
X21 is aspartic acid (D), glutamic acid (E), valine (V), or cysteine (C);
X23 is valine (V);
X24 is valine (V) or glutamine (Q);
X27 is methionine (M);
X28 is asparagine (N) or arginine (R);
X29 is threonine (T); and
X30 is cysteine (C) or is absent.

As the pharmaceutical composition according to any one of the previous specific embodiments:
in General Formula 1,
X1 is tyrosine (Y);
X2 is aminoisobutyric acid (Aib);
X7 is cysteine (C), threonine (T), or valine (V);
X10 is tyrosine (Y) or cysteine (C);
X12 is lysine (K);
X13 is tyrosine (Y) or cysteine (C);
X14 is leucine (L) or cysteine (C);
X15 is aspartic acid (D) or cysteine (C);
X16 is glutamic acid (E), serine (S), or cysteine (C);
X17 is lysine (K), arginine (R), cysteine (C), or valine (V);
X18 is arginine (R) or cysteine (C);
X19 is alanine (A) or cysteine (C);
X20 is glutamine (Q) or lysine (K);
X21 is aspartic acid (D), glutamic acid (E), or cysteine (C);
X23 is valine (V);
X24 is glutamine (Q);
X27 is methionine (M);
X28 is asparagine (N) or arginine (R);
X29 is threonine (T); and
X30 is cysteine (C) or is absent.

As the pharmaceutical composition according to any one of the previous specific embodiments:
in General Formula 1,
X1 is histidine (H), tryptophan (W), or tyrosine (Y), or is absent;
X2 is serine (S) or aminoisobutyric acid (Aib);
X7 is threonine (T), valine (V), or cysteine (C);
X10 is tyrosine (Y) or cysteine (C);
X12 is lysine (K) or cysteine (C);
X13 is tyrosine (Y) or cysteine (C);
X14 is leucine (L) or cysteine (C);
X15 is aspartic acid (D) or cysteine (C);
X16 is glutamic acid (E), serine (S), or cysteine (C);
X17 is aspartic acid (D), glutamic acid (E), lysine (K), arginine (R), serine (S), cysteine (C), or valine (V);
X18 is aspartic acid (D), glutamic acid (E), arginine (R), or cysteine (C);

X19 is alanine (A) or cysteine (C);
X20 is glutamine (Q), aspartic acid (D), or lysine (K);
X21 is aspartic acid (D) or glutamic acid (E);
X23 is valine (V);
X24 is valine (V) or glutamine (Q);
X27 is isoleucine (I) or methionine (M);
X28 is asparagine (N) or arginine (R);
X29 is threonine (T); and
X30 is cysteine (C) or is absent.

As the pharmaceutical composition according to any one of the previous specific embodiments:
in General Formula 1,
X1 is tyrosine (Y);
X2 is aminoisobutyric acid (Aib);
X7 is threonine (T);
X10 is tyrosine (Y);
X12 is lysine (K);
X13 is tyrosine (Y);
X14 is leucine (L);
X15 is aspartic acid (D) or cysteine (C);
X16 is glutamic acid (E), serine (S), or cysteine (C);
X17 is lysine (K) or arginine (R);
X18 is arginine (R);
X19 is alanine (A);
X20 is glutamine (Q), cysteine (C), or lysine (K);
X21 is aspartic acid (D), cysteine (C), valine (V), or glutamic acid (E);
X23 is valine (V) or arginine (R);
X24 is glutamine (Q) or leucine (L);
X27 is methionine (M);
X28 is asparagine (N) or arginine (R);
X29 is threonine (T); and
X30 is absent.

As the pharmaceutical composition according to any one of the previous specific embodiments, the peptide contains the amino acid sequence of the following General Formula 2:

(General Formula 2, SEQ ID NO: 46)
Y-Aib-QGTF-X7-SD-X10-S-X12-Y-L-X15-X16-X17-R-A-X20-X21-F-V-X24-W-L-M-N-T-X30 wherein, in General Formula 2,
X7 is threonine (T), valine (V), or cysteine (C);
X10 is tyrosine (Y) or cysteine (C);
X12 is lysine (K) or cysteine (C);
X15 is aspartic acid (D) or cysteine (C),
X16 is glutamic acid (E) or serine (S);
X17 is lysine (K) or arginine (R);
X20 is glutamine (Q) or lysine (K);
X21 is aspartic acid (D) or glutamic acid (E);
X24 is valine (V) or glutamine (Q); and
X30 is cysteine (C) or is absent.

As the pharmaceutical composition according to any one of the previous specific embodiments, the peptide has an isoelectric point (pI) value different from that of native glucagon (6.8), e.g., a pI of 6.5 or less, or a pI of 7.0 or higher.

As the pharmaceutical composition according to any one of the previous specific embodiments, in a specific embodiment of the present invention, each amino acid in at least one amino acid pair among the amino acid pairs of X10 and X14, X12 and X16, X16 and X20, X17 and X21, X20 and X24, and X24 and X28 in General Formula 1 or 2 is substituted with glutamic acid or lysine, which is capable of forming a ring, respectively.

As the pharmaceutical composition according to any one of the previous specific embodiments, in a specific embodiment of the present invention, each amino acid in the amino acid pair of X12 and X16 or each amino acid in the amino acid pair of X16 and X20 or each amino acid in the amino acid pair of X17 and X21 in General Formula 1 or 2 is respectively substituted with glutamic acid or lysine, which is capable of forming a ring.

As the pharmaceutical composition according to any one of the previous specific embodiments, in a specific embodiment of the present invention, in General Formula 1 or 2, a ring (e.g., a lactam ring) is formed between each amino acid in at least one amino acid pair among the amino acid pairs of X10 and X11, X12 and X16, X16 and X20, X17 and X21, X20 and X24, and X24 and X28.

As the pharmaceutical composition according to any one of the previous specific embodiments, in a specific embodiment of the present invention, in General Formula 1 or 2, X16 is glutamic acid, X20 is lysine, and the side chains of X16 and X20 form a lactam ring.

As the pharmaceutical composition according to any one of the previous specific embodiments, the C-terminus of the peptide is amidated or unmodified.

As the pharmaceutical composition according to any one of the previous specific embodiments, the peptide is a native glucagon derivative capable of activating a glucagon receptor.

As the pharmaceutical composition according to any one of the previous specific embodiments, the peptide includes an amino acid sequence selected from the group consisting of SEQ ID NOS: 2 to 44.

As the pharmaceutical composition according to any one of the previous specific embodiments, the peptide includes an amino acid sequence selected from the group consisting of SEQ ID NOS: 12, 13, 15, and 36 to 44.

As the pharmaceutical composition according to any one of the previous specific embodiments, the peptide includes the amino acid sequence of SEQ ID NO: 37.

As the pharmaceutical composition according to any one of the previous specific embodiments, the peptide is in the form of a long-acting conjugate, in which a hiocompatible material moiety is linked to the peptide moiety, and specifically to the peptide moiety including the amino acid sequence of General Formula 1 or 2.

As the pharmaceutical composition according to any one of the previous specific embodiments, the biocompatible material moiety is selected from the group consisting of a polymer, fatty acid, cholesterol, albumin and a fragment thereof an albumin-binding material, a polymer of repeating units of a particular amino acid sequence, an antibody, an antibody fragment, an FcRn-binding material, in vivo connective tissue or a derivative thereof a nucleotide, fibronectin, transferrin, a saccharide, heparin, and elastin.

As the pharmaceutical composition according to any one of the previous specific embodiments, the polymer is selected from the group consisting of a polyethylene glycol, a polypropylene glycol, an ethylene glycol-propylene glycol copolymer, polyoxyethylated polyol, polyvinyl alcohol, a polysaccharide, dextran, polyvinyl ethyl ether, a biodegradable polymer, a lipid polymer, chitin, hyaluronic acid, an oligonucleotide, and a combination thereof.

As the pharmaceutical composition according to any one of the previous specific embodiments, the FcRn-binding material is a polypeptide containing an immunoglobulin Fc region.

As the pharmaceutical composition according to any one of the previous specific embodiments, the peptide moiety and the biocompatible material moiety are linked through a linker.

As the pharmaceutical composition according to any one of the previous specific embodiments, the linker is selected from the group consisting of a peptide, fatty acid, a saccharide, a polymer, a low molecular weight compound, a nucleotide, and a combination thereof.

As the pharmaceutical composition according to any one of the previous specific embodiments, the polymer is selected from the group consisting of a polyethylene glycol, a polypropylene glycol, an ethylene glycol-propylene glycol copolymer, polyoxyethylated polyvinyl alcohol, a polysaccharide, dextran, polyvinyl ethyl ether, a biodegradable polymer, a lipid polymer, chitin, hyaluronic acid, an oligonucleotide, and a combination thereof.

As the pharmaceutical composition according to any one of the previous specific embodiments, the linker is a polyethylene glycol.

As the pharmaceutical composition according to any one of the previous specific embodiments, the immunoglobulin Fc region is aglycosylated.

As the pharmaceutical composition according to any one of the previous specific embodiments, the immunoglobulin Fc region is selected from the group consisting of:

(a) a CH1 domain, a CH2 domain, a CH3 domain, and a CH4 domain;
(b) a CH1 domain and a CH2 domain;
(c) a CH1 domain and a CH3 domain;
(d) a CH2 domain and a CH3 domain;
(e) a combination between one or at least two domains among a CH1 domain, a CH2 domain, a CH3 domain, and a CH4 domain, and an immunoglobulin hinge region or a part of the hinge region; and
(f) a dimer between each domain of the heavy chain constant region and the light chain constant region.

As the pharmaceutical composition according to any one of the previous specific embodiments, the polypeptide containing an immunoglobulin Fc region is in the form of a dimer.

As the pharmaceutical composition according to any one of the previous specific embodiments, the immunoglobulin Fc region is a native Fc derivative in which the region capable of forming a disulfide bond is deleted, a native Fc derivative in which a part of the amino acid(s) in the N-terminus is removed, a native Fc derivative in which a methionine residue is added to the N-terminus, a native Fc derivative in which a complement-binding site is deleted, or a native Fc derivative in which an antibody dependent cell mediated cytotoxicity (ADCC) site is deleted.

As the pharmaceutical composition according to any one of the previous specific embodiments, the immunoglobulin Fc region is derived from an immunoglobulin selected from the group consisting of IgG, IgA, IgD, IgE, and IgM.

As the pharmaceutical composition according to any one of the previous specific embodiments, the immunoglobulin Fc region is an IgG4 Fc region.

As the pharmaceutical composition according to any one of the previous specific embodiments, the immunoglobulin Fc region is an aglycosylated Fc region derived from human IgG4.

As the pharmaceutical composition according to any one of the previous specific embodiments, the linker is linked to a cysteine residue of a peptide including the amino acid sequence of General Formula 1 or 2.

As the pharmaceutical composition according to any one of the previous specific embodiments, in a specific embodiment of the present invention, the linker of the conjugate is respectively linked to the peptide moiety and the biocompatible material moiety through covalent bonds, which were respectively formed when one end of the linker reacted with an amine group or thiol group of the biocompatible material moiety while the other end of the linker reacted with an amine group or thiol group of the peptide moiety including the amino acid sequence of General Formula 1 or 2, respectively.

Another aspect of the present invention provides a glucagon derivative.

In a specific embodiment, the present invention relates to an isolated peptide including the amino acid sequence of General Formula 1 represented by SEQ ID NO: 45.

In another specific embodiment, the present invention relates to an isolated peptide including the amino acid sequence of the following General Formula 2:

(General Formula 2, SEQ ID NO: 46)
Y-Aib-QGTF-X7-SD-X10-S-X12-Y-L-X15-X16-X17-R-A-X20-X21-F-V-X24-W-L-M-N-T-X30 wherein, in General Formula 2,
X7 is threonine (T), valine (V), or cysteine (C);
X10 is tyrosine (Y) or cysteine (C);
X12 is lysine (K) or cysteine (C);
X15 is aspartic acid (D) or cysteine (C);
X16 is glutamic acid (E) or serine (S);
X17 is lysine (K) or arginine (R);
X20 is glutamine (Q) or lysine (K);
X21 is aspartic acid (D) or glutamic acid (E);
X24 is valine (V) or glutamine (Q); and
X30 is cysteine (C) or is absent.

In the isolated peptide according to the previous specific embodiment, the peptides corresponding to SEQ ID NOS: 19, 33, 49, and 50 may be excluded from the isolated peptides including the amino acid sequence of General Formula 2.

In the isolated peptide according to any one of the previous specific embodiments, in General Formula 2, X16 is glutamic acid, X20 is lysine, and the side chains of X16 and X20 form a lactam ring.

In the isolated peptide according to any one of the previous specific embodiments, the C-terminus of the peptide comprising the amino acid sequence of General Formula 2 is amidated or unmodified.

In the isolated peptide according to any one of the previous specific embodiments, the peptide is a glucagon derivative capable of activating a glucagon receptor.

In the isolated peptide according to any one of the previous specific embodiments, the peptide includes an amino acid sequence selected from the group consisting of SEQ ID NOS: 12, 13, 15, and 36 to 44.

Still another aspect of the present invention provides an isolated polynucleotide encoding the isolated peptide (specifically, the isolated peptide which includes the amino acid sequence of General Formula 1 or 2), a vector including the isolated polynucleotide, and an isolated cell including the polynucleotide or vector.

Still another aspect of the present invention provides an isolated conjugate including a peptide moiety and a biocompatible material moiety covalently linked to the peptide moiety, in which the peptide moiety has the same amino acid sequence of General Formula 1 or 2 or includes the same.

In a specific embodiment, the present invention relates to an isolated conjugate including a peptide moiety and a biocompatible material moiety covalently linked to the peptide moiety, in which the peptide moiety has the same amino acid sequence of General Formula 1 or includes the same.

In a specific embodiment, the present invention relates to an isolated conjugate including a peptide moiety and a biocompatible material moiety covalently linked to the peptide moiety, in which the peptide moiety has the same amino acid sequence of General Formula 2 or includes the same.

In the conjugate according to the previous specific embodiment, the biocompatible material moiety is selected from the group consisting of a polymer, fatty acid, cholesterol, albumin and a fragment thereof, an albumin-binding material, a polymer of repeating units of a particular amino acid sequence, an antibody, an antibody fragment, an FcRn-binding material, in vivo connective tissue or a derivative thereof, a nucleotide, fibronectin, transferrin, a saccharide, heparin, and elastin.

In the conjugate according to any one of the previous specific embodiments, the polymer is selected from the group consisting of a polyethylene glycol, a polypropylene glycol, an ethylene glycol-propylene glycol copolymer, polyoxyethylated polyol, polyvinyl alcohol, a polysaccharide, dextran, polyvinyl ethyl ether, a biodegradable polymer, a lipid polymer, chitin, hyaluronic acid, an oligonucleotide, and a combination thereof.

In the conjugate according to any one of the previous specific embodiments, the FcRn-binding material is a polypeptide comprising an immunoglobulin Fc region.

In the conjugate according to any one of the previous specific embodiments, the peptide region and the biocompatible material moiety are linked through a linker.

As the conjugate according to any one of the previous specific embodiments, the linker is selected from the group consisting of a peptide, fatty acid, a saccharide, a polymer, a low molecular weight compound, a nucleotide, and a combination thereof.

In the conjugate according to any one of the previous specific embodiments, the linker is a polymer selected from the group consisting of a polyethylene glycol, a polypropylene glycol, an ethylene glycol-propylene glycol copolymer, polyoxyethylated polyol, polyvinyl alcohol, a polysaccharide, dextran, polyvinyl ethyl ether, a biodegradable polymer, a lipid polymer, chitin, hyaluronic acid, an oligonucleotide, and a combination thereof.

In the conjugate according to any one of the previous specific embodiments, the biocompatible material moiety is an FcRn-binding material, and the biocompatible material moiety is linked to the peptide moiety through a linker selected from the group consisting of a peptide, fatty acid, a saccharide, a polymer, a low molecular weight compound, a nucleotide, and a combination thereof.

In the conjugate according to any one of the previous specific embodiments, the linker is a polyethylene glycol.

In the conjugate according to any one of the previous specific embodiments, imrrlunoglobulin Fc region is aglycosylated.

In the conjugate according to any one of the previous specific embodiments, the immunoglobulin Fc region is selected from the group consisting of: (a) a CH1 domain, a CH2 domain, a CH3 domain, and a CH4 domain; (b) a. CH1 domain and a CH2 domain; (c) a CH1 domain and a CH3 domain; (d) a CH2 domain and a CH3 domain; (e) a combination between one or at least two domains among a CH1 domain, a CH2 domain, a CH3 domain, and a CH4 domain, and an immunoglobulin hinge region or a part of the hinge region; and (f) a dimer between each domain of the heavy chain constant region and the light chain constant region.

In the conjugate according to any one of the previous specific embodiments, the polypeptide including an immunoglobulin Fc region is in the form of a dimer.

In the conjugate according to any one of the previous specific embodiments, the immunoglobulin Fc region is a native Fc derivative in which the region capable of forming a disulfide bond is deleted, a native Fc derivative in which a part of the amino acid(s) in the N-terminus is removed, a native Fc derivative in which a methionine residue is added to the N-terminus, a native Fc derivative in which a complement-binding site is deleted, or a native Fc derivative in which an antibody dependent cell mediated cytotoxicity (ADCC) site is deleted.

In the conjugate according to any one of the previous specific embodiments, the immunoglobulin Fc region is derived from an immunoglobulin selected from the group consisting of IgG, IgA, IgD, IgE, and IgM.

In the conjugate according to any one of the previous specific embodiments, the immunoglobulin Fc region is an IgG4 Fc region.

In the conjugate according to any one of the previous specific embodiments, the immunoglobulin Fc region is an aglycosylated Fc region derived from human IgG4.

In the conjugate according to any one of the previous specific embodiments, the linker is linked to a cysteine residue of the peptide.

In the conjugate according to any one of the previous specific embodiments, in a specific embodiment of the present invention, the linker of the conjugate is respectively linked to the peptide moiety and the biocompatible material moiety through covalent bonds, which were respectively formed when one end of the linker reacted with an amine group or thiol group of the biocompatible material moiety while the other end of the linker reacted with an amine group or thiol group of the peptide moiety including the amino acid sequence of General Formula 1 or 2, respectively.

Still another aspect of the present invention provides a pharmaceutical composition for preventing or treating hypoglycemia containing a glucagon derivative or a conjugate containing the same and a pharmaceutically acceptable excipient.

In a specific embodiment, the present invention relates to a pharmaceutical composition for preventing or treating hypoglycemia, which contains the isolated peptide or the isolated conjugate, which includes a peptide moiety, that has the same sequence as that of the isolated peptide or includes a sequence including the same, and a biocompatible material moiety covalently linked to the peptide moiety.

Still another aspect of the present invention provides a pharmaceutical composition for preventing or treating metabolic syndrome containing a glucagon derivative or a conjugate containing the same and a pharmaceutically acceptable excipient.

In a specific embodiment, the present invention relates to a pharmaceutical composition for preventing or treating metabolic syndrome, which contains the isolated peptide; or the isolated conjugate, which includes a peptide moiety, that has the same sequence as that of the isolated peptide or includes a sequence including the same, and a biocompatible material moiety covalently linked to the peptide moiety.

In the pharmaceutical composition according to any one of the previous specific embodiments, the pharmaceutical composition further contains at least one compound or material having the therapeutic activity for metabolic syndrome.

In the pharmaceutical composition according to any one of the previous specific embodiments, the compound or material having the therapeutic activity for metabolic syndrome is selected from the group consisting of an insulinotropic peptide, a glucagon like peptide-1 (GLP-1) receptor agonist, a leptin receptor agonist, a dipeptidyl peptidase-IV (DPP-IV) inhibitor, a Y5 receptor antagonist, a melanin-concentrating hormone (MCH) receptor antagonist, a Y2/4 receptor agonist, a melanocortin 3/4 (MC 3/4) receptor agonist, a gastric/pancreatic lipase inhibitor, an agonist of 5-hydroxytryptamine receptor 2C (5HT2$_C$, G-protein coupled), a β3A receptor agonist, an amylin receptor agonist, a ghrelin antagonist, a ghrelin receptor antagonist, a peroxisome proliferator-activated receptor alpha (PPARα) agonist, a peroxisome proliferator-activated receptor delta (PPARδ) agonist, a Farnesoid X receptor (FXR) agonist, an acetyl-CoA carboxylase inhibitor, a peptide YY, cholecystokinin (CCK), xenin, glicentin, obestatin, secretin, nesfatin, insulin, and a glucose-dependent insulinotropic peptide (GIP).

In the pharmaceutical composition according to any one of the previous specific embodiments, the insulinotropic peptide is selected from the group consisting of GLP-1, exendin-3, exendin-4, an agonist thereof, a derivative thereof, a fragment thereof, a variant thereof, and a combination thereof.

In the pharmaceutical composition according to any one of the previous specific embodiments, the insulinotropic peptide is an insulinotropic peptide derivative in which the N-terminal histidine of the insulinotropic peptide is substituted with one selected from the group consisting of desamino-histidyl, N-dimethyl-histidyl, β-hydroxy imidazopropionyl, 4-imidazoacetyl, and β-carboxy imidazopropionyl.

In the pharmaceutical composition according to any one of the previous specific embodiments, the insulinotropic peptide is selected from the group consisting of a native exendin-4; an exendin-4 derivative in which the N-terminal amine group of exendin-4 is deleted; an exendin-4 derivative in which the N-terminal amine group of exendin-4 is substituted with a hydroxyl group; an exendin-4 derivative in which the N-terminal amine group of exendin-4 is modified with a dimethyl group; an exendin-4 derivative in which the α-carbon of the 1$^{st}$ amino acid of exendin-4, histidine, is deleted; an exendin-4 derivative in which the 12$^{th}$ amino acid of exendin-4, lysine, is substituted with serine, and an exendin-4 derivative in which the 12$^{th}$ amino acid of exendin-4, lysine, is substituted with arginine.

In the pharmaceutical composition according to any one of the previous specific embodiments, the insulinotropic peptide is in the form of a long-acting conjugate, which includes a peptide moiety, that includes the same amino acid sequence as that of the insulinotropic peptide, and a biocompatible material moiety covalently linked to the peptide moiety.

In the pharmaceutical composition according to any one of the previous specific embodiments, the biocompatible material moiety is selected from the group consisting of a polymer, fatty acid, cholesterol, albumin and a fragment thereof, an albumin-binding material, a polymer of repeating units of a particular amino acid sequence, an antibody, an antibody fragment, an FcRn-binding material, in vivo connective tissue or a derivative thereof, a nucleotide, fibronectin, transferrin, a saccharide, heparin, and elastin.

In the pharmaceutical composition according to any one of the previous specific embodiments, the polymer is selected from the group consisting of a polyethylene glycol, a polypropylene glycol, an ethylene glycol-propylene glycol copolymer, polyoxvethylated polyol, polyvinyl alcohol, a polysaccharide, dextran, polyvinyl ethyl ether, a biodegradable polymer, a lipid polymer, chitin, hyaluronic acid, an oligonucleotide, and a combination thereof.

In the pharmaceutical composition according to any one of the previous specific embodiments, the FcRn-binding material is a polypeptide including an immunoglobulin Fc region.

In the pharmaceutical composition according to any one of the previous specific embodiments, the peptide moiety including the amino acid sequence of the insulinotropic peptide is linked to the biocompatible material moiety through a linker.

In the pharmaceutical composition according to any one of the previous specific embodiments, the linker is selected from the group consisting of a peptide, fatty acid, a saccharide, a polymer, a low molecular weight compound, a nucleotide, and a combination thereof.

In the pharmaceutical composition according to any one of the previous specific embodiments, the linker is a polymer selected from the group consisting of a polyethylene glycol, a polypropylene glycol, an ethylene glycol-propylene glycol copolymer, polyoxyethylated polyol, polyvinyl alcohol, a polysaccharide, dextran, polyvinyl ethyl ether, a biodegradable polymer, a lipid polymer, chitin, hyaluronic acid, an oligonucleotide, and a combination thereof.

In the pharmaceutical composition according to any one of the previous specific embodiments, the metabolic syndrome is selected from the group consisting of impaired glucose tolerance, hypercholesterolemia, dyslipidemia, obesity, diabetes, hypertension, nonalcoholic steatohepatitis (NASH), atherosclerosis caused by dyslipidemia, atherosclerosis, arteriosclerosis, coronary heart disease, stroke, etc.

In the pharmaceutical composition according to any one of the previous specific embodiments, the insulinotropic peptide is linked to a biocompatible material moiety through a linker selected from the croup consisting of a polyethylene glycol, a polypropylene glycol, an ethylene glycol-propylene glycol copolymer, polyoxyethylated polyol, polyvinyl alcohol, a polysaccharide, dextran, polyvinyl ethyl ether, a biodegradable polymer such as polylactic acid (PLA) and polylactic-glycolic acid (PLGA), a lipid polymer, chitins, hyaluronic acid, fatty acid, a polymer, a low molecular weight compound, a nucleotide, and a combination thereof.

In the pharmaceutical composition according to any one of the previous specific embodiments, the biocompatible material moiety is an FcRn-binding material, and the peptide moiety including the amino acid sequence of the insulinotropic peptide is linked to a biocompatible material moiety through a peptide linker; or a non-peptide linker selected from the group consisting of a polyethylene glycol, a polypropylene glycol, an ethylene glycol-propylene glycol copolymer, polyoxyethylated polyol, polyvinyl alcohol, a polysaccharide, dextran, polyvinyl ethyl ewer, a biodegradable polymer such as polylactic acid (PLA) and polylactic-glycolic acid (PLGA), a lipid polymer, chitins, hyaluronic acid, and a combination thereof.

In the pharmaceutical composition according to any one of the previous specific embodiments, the composition may include both (i) a conjugate, which includes the peptide moiety including the amino acid sequence of SEQ ID NO: 37, and a biocompatible material moiety covalently linked to the peptide moiety; and (ii) a conjugate, which includes an imidazo-acetyl exendin-4 moiety where the α-carbon of the 1$^{st}$ amino acid of exendin-4 (i.e., histidine) is deleted and a biocompatible material moiety covalently linked to the imidazo-acetyl exendin-4 moiety.

In the pharmaceutical composition according to any one of the previous specific embodiments, the peptide moiety including the amino acid sequence of SEQ ID NO: 37 and the imidazo-acetyl exendin-4 moiety are linked to their respective biocompatible material moiety's through a linker.

In the pharmaceutical composition according to any one of the previous specific embodiments, the FcRn-binding material is a polypeptide including an immunoglobulin. Fc region.

Still another aspect of the present invention provides a method for preventing or treating congenital hyperinsulinism including administering the glucagon derivative or a conjugate containing the same or a composition containing the same to a subject in need thereof.

Still another aspect of the present invention provides use of the glucagon derivative or the conjugate containing the same or the composition containing the same in the preparation of a medicament for preventing or treating congenital hyperinsulinism.

Still another aspect of the present invention provides a method for preventing or treating hypoglycemia including administering the glucagon derivative or a conjugate containing the same or a composition containing the same to a subject in need thereof.

Still another aspect of the present invention provides use of the glucagon derivative or the conjugate containing the same or the composition containing the same in the preparation of a medicament for preventing or treating hypoglycemia.

Still another aspect of the present invention provides a method for preventing or treating metabolic syndrome including administering the glucagon derivative or a conjugate containing the same or a composition containing the same to a subject in need thereof.

In a specific embodiment, the method further includes administering at least one compound or material having a therapeutic activity for metabolic syndrome.

In the method according to any one of the previous specific embodiments, the glucagon derivative or a conjugate containing the same and the compound or material having a therapeutic activity for metabolic syndrome is administered simultaneously, individually, or sequentially.

Still another aspect of the present invention provides use of the glucagon derivative or the conjugate containing the same or the composition containing the same in the preparation of a medicament (or pharmaceutical compositon) for preventing or treating metabolic syndrome.

[Advantageous Effects of the Invention]

The glucagon derivatives of the present invention have improved physical properties compared to those of native glucagon, and can be effectively used for the prevention and treatment of metabolic syndrome, such as obesity, diabetes, and nonalcoholic steatohepatitis (NASH), and congenital hyperinsulinism.

BRIEF DESCRIPTION OF THE DRAWINGS

FIG. 1 shows a graph illustrating the changes in body weight of obesity animal models (rats), which were prepared by high-fat diet, during a single or combined administration of a long-acting insulinotropic peptide conjugate (named as a long-acting exendin-4 derivative) and a long-acting glucagon derivative conjugate (named as a long-acting derivative of SEQ ID NO: 12) with an adjusted dose to the rats, at 3-day intervals for 15 days.

FIG. 2 shows a result illustrating the amount of mesenteric fat of obesity animal models (rats), which were prepared by high-fat diet, measured after a single or combined administration of a long-acting insulinotropic peptide conjugate (named as a long-acting exendin-4 derivative) and a long-acting glucagon derivative conjugate (named as a long-acting derivative of SEQ ID NO: 12) with an adjusted dose to the rats for 15 days (*p<0.05 compared to vehicle, **p<0.01 vs. one-way ANOVA analysis).

FIG. 3 shows a result illustrating the difference in liver weight of obesity animal models (rats), which were prepared by high-fat diet, measured after a single or combined administration of a long-acting insulinotropic peptide conjugate (named as a long-acting exendin-4 derivative) and a long-acting glucagon derivative conjugate (named as a long-acting derivative of SEQ ID NO: 12) with an adjusted dose to the rats for 15 days (*p<0.01, *p<0.001 compared to vehicle vs. one-way ANOVA analysis).

FIG. 4 shows a graph illustrating the changes in body weight (BW) of obesity animal models (mice), which were prepared by high-fat diet, after a single or combined administration of a long-acting insulinotropic peptide conjugate (named as a long-acting exendin-4 derivative) and a long-acting glucagon derivative conjugate (named as a long-acting derivative of SEQ ID NO: 20) with an adjusted dose to the mice for 22 days.

FIG. 5 shows a result illustrating the changes in cholesterol content in blood of obesity animal models (mice), which were prepared by high-fat diet, after a single or combined administration of a long-acting insulinotropic peptide conjugate (named as a long-acting exendin-4 derivative) and a long-acting glucagon derivative conjugate (named as a long-acting derivative of SEQ ID NO: 20) with an adjusted dose to the mice for 22 days.

FIG. 6 shows a result illustrating the changes in body weight, blood cholesterol levels, fat weight, and impaired glucose tolerance of obesity animal models (mice), which were prepared by high-fat diet, after a single administration of liraglutide (Novo Nordisk) and a long-acting insulinotropic peptide conjugate (named as a long-acting exendin-4 derivative), or combined administration of a long-acting insulinotropic peptide conjugate (named as a long-acting exendin-4 derivative) and a long-acting glucagon derivative conjugate (named as a long-acting derivative of SEQ ID NO: 37) with an adjusted dose to the mice for 28 days. The effects compared to vehicle (administered with an excipient) are shown.

FIG. 7 shows a result illustrating the effect of ameliorating hypoglycemia according to the administration of a long-acting conjugate of glucagon derivative of SEQ ID NO: 37 in acute hypoglycemia animal models (rats).

FIG. 8 shows a result illustrating the effect of ameliorating hypoglycemia according to the administration of a long-acting conjugate of glucagon derivative of SEQ ID NO: 37 in chronic hypoglycemia animal models (rats).

BEST MODE

Detailed Description of Preferred Embodiments

The specific details of the present invention may be explained as follows. In particular, the explanations and embodiments disclosed in the present invention may be applied to other explanations and embodiments, respectively. That is, all combinations of various elements disclosed in the present invention belong to the scope of the present invention. Additionally, the scope of the present invention should not be limited by the specific descriptions described herein below.

Additionally, those of ordinary skill in the art may be able to recognize or confirm, using only conventional experimentation, many equivalents to the particular aspects of the invention described in this application. Furthermore, it is also intended that these equivalents be included in the present invention.

Throughout the disclosure of the present invention, not only the conventional 1-letter codes and 3-letter codes for amino acids present in nature but also the 3-letter codes, such as Aib (α-aminoisobutyric acid), Sar(N-methylglycine) generally used for other amino acids, are used. Additionally, the amino acids mentioned in abbreviation in the present disclosure are described according to the IUPAC-IUB Nomenclature.

| alanine A | arginine R |
| asparagine N | aspartic acid D |
| cysteine C | glutamic acid E |
| glutamine Q | glycine G |
| histidine H | isoleucine I |
| leucine L | lysine K |
| methionine M | phenylalanine F |
| proline P | serine S |
| threonine T | tryptophan W |
| tyrosine Y | valine V |

An aspect of the present invention provides a composition containing a glucagon derivative or a conjugate containing the same, and specifically, a pharmaceutical composition for preventing or treating congenital hyperinsulinism, hypoglycemia, or metabolic syndrome containing a glucagon derivative or a conjugate containing the same.

The glucagon derivative according to the present invention includes a peptide having at least one difference in the amino acid sequence compared to native glucagon, a peptide in which the sequence of native glucagon is modified by modifying native glucagon, and a native glucagon mimetic that can activate glucagon receptors like native glucagon.

Such a glucagon derivative may be one having improved physical properties by having an altered pI relative to native glucagon. Additionally, the glucagon derivative may be one with improved solubility while having the activity of activating glucagon receptors, but is not limited thereto.

Additionally, the glucagon derivative may be a non-naturally occurring glucagon.

In particular, native glucagon may have the following amino acid sequence:

(SEQ ID NO: 1)
His-Ser-Gln-Gly-Thr-Phe-Thr-Ser-Asp-Tyr-Ser-Lys-
Tyr-Leu-Asp-Ser-Arg-Arg-Ala-Gln-Asp-Phe-Val-Gln-
Trp-Leu-Met-Asn-Thr

As used herein, the term "isoelectric point" or "pI" refers to the pH value at which a molecule such as a polypeptide or peptide has no net charge (0). In the case of a polypeptide with various charged functional groups, the net charge of the total polypeptide is "0" at a point where the pH value is the same as that of the pI. The net charge of the polypeptide at a pH higher than the pI will be negative while the net charge of the polypeptide at a pH lower than the pI will be positive.

The pI values may be determined on an immobilized pH gradient gel consisting of polyacrylamide, starch, or agarose by isoelectric electrophoresis, or may be estimated, for example, from an amino acid sequence using a pI/MW tool (expasy.org/tools/pi_tool; Gasteiger et al., 2003) in an ExPASy server.

As used herein, the term "altered pI" refers to a pI which is different from that of native glucagon due to the substitution of a part of the amino acid sequence of native glucagon with an amino acid residue having a negative charge or a positive charge, i.e., a reduced or increased pi value. The peptide with such an altered pI can exhibit improved solubility and/or high stability at a neutral pH as a glucagon derivative, but is not particularly limited thereto.

More specifically, the glucagon derivative may have an altered pI value, not the pI value (6.8) of native glucagon, and even more specifically, a pI value of less than 6.8, more specifically, 6.7 or less, more specifically 6.5 or less, and additionally, a pI value exceeding 6.8, 7 or higher, more specifically, 7.5 or higher, but is not limited thereto, and any pI value different from that of native glucagon will belong to the scope of the present invention. In particular, when the pI value is different from that of native glucagon and thus exhibits an improved solubility at a neutral pH compared to that of native glucagon thus showing a low level of aggregation, it will particularly belong to the scope of the present invention.

More specifically, the glucagon derivative may have a pI value of from 4 to 6.5 and/or from 7 to 9.5, specifically from 7.5 to 9.5, and more specifically, from 8.0 to 9.3, but the pI value is not limited thereto. In this case, due to the lower or higher pI value compared to that of native glucagon, an improved solubility and high stability at a neutral pH compared to that of native glucagon can be exhibited, but is not particularly limited thereto.

Specifically, a derivative of native glucagon may be modified by any one method of substitution, addition, deletion, and modification, or a combination thereof in part of the amino acid of native glucagon.

Examples of the glucagon derivatives prepared by a combination of the above methods include a peptide which differs in at least one amino acid residue of the amino acid sequence compared to that of native glucagon and in which the N-terminal amino acid residue is deatninated, having the function of activating a glucagon receptor, but is not limited thereto, and the native glucagon derivatives can be prepared by a combination of various methods for preparing the derivatives.

Additionally, such modification for the preparation of native glucagon derivatives may include all of the modifications using L-type or D-type amino acids, and/or non-native type amino acids; and/or a modification of native sequence, for example, modification of a functional group, an intramolecular covalent bonding (e.g, a ring formation between side chains), methylation, acylation, ubiquitination, phosphorylation, aminohexanation, biotinylation, etc. Additionally, the modification may also include substitutions into non-native compounds.

Additionally, the modification may also include all those where one or more amino acids are added to the amino and/or carboxy terminal of native glucagon.

During the substitution or addition of amino acids, not only the 20 amino acids commonly found in human proteins, but also atypical or non-naturally occurring amino acids can be used. Commercial sources of atypical amino acids may include Sigma-Aldrich, ChemPep Inc., and Genzyme Pharmaceuticals. The peptides including these amino acids and typical peptide sequences may be synthesized and purthased from commercial suppliers, e.g., American Peptide Company, Bachem (USA), or Antigen (Korea).

Amino acid derivatives may also be obtained in a similar manner, for example, 4-imidazoacetic acid, etc., may be used.

Since glucagon has a pH of about 7, it is insoluble in a solution having a physiological pH (pH 4 to 8) and tends to precipitate at a neutral pH. In an aqueous solution with a pH of 3 or below, glucagon is dissolved at the initial stage but precipitates within one hour by forming a gel. Since the gelated glucagon mainly consists of β-sheet fibrils, the administration of the thus-precipitated glucagon via an injection needle or intravenous injection will block blood vessels, and thus is not suitable for use as an injection agent. In order to delay the precipitation process, acidic (pH 2 to 4) formulations are commonly used, and by doing so, glucagon can be maintained in a relatively non-aggregated state for a short period of time. However, glucagon can form fibrils very rapidly at a low pH, and thus these acidic formulations must be injected upon preparation.

In this regard, the present inventors have developed glucagon derivatives with extended action profiles by modifying the pi of native glucagon via substitution of amino acid residues having negative charges and positive charges. The glucagon derivatives of the present invention, by having an altered pI compared to that of native glucagon, are characterized in having improved solubility and/or high stability at a neutral pH, compared to that of native glucagon.

In a specific embodiment of the present invention, the glucagon derivative may be a peptide which includes the amino acid sequence of the following General Formula. 1:

(General Formula 1, SEQ ID NO: 45)
X1-X2-QGTF-X7-SD-X10-S-X12-X13-X14-X15-X16-X17-
X18-X19-X20-X21-F-X23-X24-W-L-X27-X28-X29-X30

In the above Formula,

X1 is histidine, desamino-histidyl, β-hydroxy imidazopropionyl, 4-imidazoacetyl, β-carboxy imidazopropionyl, tryptophan, or tyrosine, or is absent;

X2 is α-methyl-glutamic acid, aminoisobutyric acid (Aib), D-alanine, glycine, Sar(N-methylglycine), serine, or D-serine;

X7 is threonine, valine, or cysteine;

X10 is tyrosine or cysteine;

X12 is lysine or cysteine;

X13 is tyrosine or cysteine;

X14 is leucine or cysteine;

X15 is aspartic acid, glutamic acid, or cysteine;

X16 is glutamic acid, aspartic acid, serine, α-methyl-glutamic acid, or cysteine, or is absent;

X17 is aspartic acid, glutamine, glutamic acid, lysine, arginine, serine, cysteine, or valine, or is absent;

X18 is alanine, aspartic acid, glutamic acid, arginine, valine, or cysteine, or is absent;

X19 is alanine, arginine, serine, valine, or cysteine, or is absent;

X20 is lysine, histidine, glutamine, aspartic acid, arginine, α-methyl-glutamic acid, or cysteine, or is absent;

X21 is aspartic acid, glutamic acid, leucine, valine, or cysteine, or is absent;

X23 is isoleucine, valine, or arginine, or is absent;

X24 is valine, arginine, alanine, cysteine, glutamic acid, lysine, glutamine, α-methyl-glutamic acid, or leucine, or is absent;

X27 is isoleucine, valine, alanine, lysine, methionine, glutamine, or arginine, or is absent;

X28 is glutamine, lysine, asparagine, or arginine, or is absent;

X29 is lysine, alanine, glycine, or threonine, or is absent; and

X30 is cysteine or is absent;

with the proviso that when the amino acid sequence of General Formula 1 is identical to SEQ ID NO: 1, it is excluded.

More specifically, in General Formula 1,

X1 is histidine, tryptophan, or tyrosine, or is absent:

X2 is serine or aminoisobutyric acid (Aib);

X7 is threonine, valine, or cysteine;

X10 is tyrosine or cysteine;

X12 is lysine or cysteine;

X13 is tyrosine or cysteine;

X14 is leucine or cysteine;

X15 is aspartic acid or cysteine;

X16 is glutamic acid, serine, or cysteine;

X17 is aspartic acid, glutamic acid, lysine, arginine, serine, cysteine, or valine;

X18 is aspartic acid, glutamic acid, arginine, or cysteine;

X19 is alanine or cysteine,

X20 is glutamine, aspartic acid, lysine, or cysteine;

X21 is aspartic acid, glutamic acid, leucine, valine, or cysteine;

X23 is isoleucine, valine, or arginine;

X24 is valine, arginine, alanine, glutamic acid, lysine, glutamine, or leucine;

X27 is isoleucine, valine, alanine, methionine, glutamine, or arginine;

X28 is glutamine, lysine, asparagine, or arginine;

X29 is threonine: and

X30 is cysteine or is absent with the proviso that when the amino acid sequence of General Formula 1 is identical to SEQ ID NO: 1, it is excluded.

For example, the peptide may be one which includes an amino acid sequence selected from the group consisting of SEQ ID NOS: 2 to 44, and specifically, one which (essentially) consists of an amino acid sequence selected from the group consisting of SEQ ID NOS: 2 to 44, but is not limited thereto.

Additionally, although described as "a peptide consisting of a particular SEQ ID NO" in the present invention, such expression does not exclude a mutation in the peptide that can occur by a meaningless sequence addition upstream or downstream of the amino acid sequence of the corresponding SEQ ID NO, or a naturally-occurring mutation therein, or a silent mutation therein, as long as the peptide having such mutation has an activity the same as or corresponding to that of the peptide which consists of an amino acid sequence of the corresponding SEQ ID NO. Even when the sequence addition or a mutation is present, it obviously belongs to the scope of the present invention.

Those described above may be also applied to other specific embodiments or aspects of the present invention, but are not limited thereto.

Specifically, in General Formula 1 above,

X1 may be histidine, tryptophan, or tyrosine;

X2 may be serine or aminoisobutyric acid (Aib);

X7 may be cysteine, threonine, or valine;

X10 may be tyrosine or cysteine;

X12 may be lysine or cysteine;

X13 may be tyrosine or cysteine;

X14 may be leucine or cysteine;
X15 may be aspartic acid or cysteine;
X16 may be glutamic acid, serine, or cysteine;
X17 may be glutamic acid, lysine, arginine, cysteine, or valine;
X18 may be arginine or cysteine;
X19 may be alanine or cysteine;
X20 may be glutamine or lysine;
X21 may be aspartic acid, glutamic acid, valine, or cysteine;
X23 may be valine;
X24 may be valine or glutamine;
X27 may be methionine;
X28 may be asparagine or arginine;
X29 may be threonine; and
X30 may be cysteine or is absent.

For example, the peptide may be one which includes an amino acid sequence selected from the group consisting of SEQ ID NOS: 3, 11 to 17, 19 to 27, 29, 31, 33, and 35 to 44, and specifically, one which (essentially) consists of an amino acid sequence selected from the group consisting of SEQ ID NOS: 3, 11 to 17, 19 to 27, 29, 31, 33, and 35 to 44, but is not limited thereto.

Specifically, in General Formula 1 above,
X1 may be tyrosine;
X2 may be aminoisobutyric acid (Aib);
X7 may be cysteine, threonine, or valine;
X10 may be tyrosine or cysteine;
X12 may be lysine;
X13 may be tyrosine or cysteine;
X14 may be leucine or cysteine;
X15 may be aspartic acid or cysteine;
X16 may be glutamic acid, serine, or cysteine;
X17 may be lysine, arginine, cysteine, or valine;
X18 may be arginine or cysteine;
X19 may be alanine or cysteine;
X20 may be glutamine or lysine;
X21 may be aspartic acid, glutamic acid, or cysteine;
X23 may be valine;
X24 may be glutamine;
X27 may be methionine;
X28 may be asparagine or arginine;
X29 may be threonine; and
X30 may be cysteine or is absent,
with the proviso that when the amino acid sequence of General Formula 1 is identical to SEQ ID NO: 1, it is excluded.

For example, the peptide may be one which includes an amino acid sequence selected from the group consisting of SEQ ID NOS: 12, 14, 17, 19 to 25, 27, 29, 33, 35 to 38, 40 to 42, and 44, and specifically, one which (essentially) consists of an amino acid sequence selected from the group consisting of SEQ ID NOS: 12, 14, 17, 19 to 25, 27, 29, 33, 35 to 38, 40 to 42, and 44, but is not limited thereto.

Specifically, in General Formula 1,
X1 may be histidine, tryptophan, or tyrosine, or is absent;
X2 may be serine or aminoisobutyric acid (Aib);
X7 may be threonine, valine, or cysteine;
X10 may be tyrosine or cysteine;
X12 may be lysine or cysteine;
X13 may be tyrosine or cysteine;
X14 may be leucine or cysteine;
X15 may be aspartic acid or cysteine;
X16 may be glutamic acid, serine, or cysteine;
X17 may be aspartic acid, glutamic acid, lysine, arginine, serine, cysteine, or valine;
X18 may be aspartic acid, glutamic acid, arginine, or cysteine;
X19 may be alanine or cysteine;
X20 may be glutamine, aspartic acid, or lysine;
X21 may be aspartic acid or glutamic acid;
X23 may be valine;
X24 may be valine or glutamine;
X27 may be isoleucine or methionine;
X28 may be asparagine or arginine;
X29 may be threonine; and
X30 may be cysteine or may be absent,
with the proviso that when the amino acid sequence of General Formula 1 is identical to SEQ ID NO: 1, it is excluded.

For example, the peptide may be one which includes an amino acid sequence selected from the group consisting of SEQ ID NOS: 2 to 13, 15, 17, 20 to 24, 26 to 30, and 32 to 44, and specifically, one which (essentially) consists of an amino acid sequence selected from the group consisting of SEQ ID NOS: 2 to 13, 15, 17, 20 to 24, 26 to 30, and 32 to 44, but is not limited thereto.

Specifically, in the General Formula 1,
X1 may be tyrosine;
X2 may be aminoisobutyric acid (Aib);
X7 may be threonine;
X10 may be tyrosine;
X12 may be lysine;
X13 may be tyrosine;
X14 may be leucine;
X15 may be aspartic acid or cysteine;
X16 may be glutamic acid, serine, or cysteine;
X17 may be lysine or arginine;
X18 may be arginine;
X19 may be alanine;
X20 may be glutamine, cysteine, or lysine;
X21 may be aspartic acid, cysteine, valine, or glutamic acid;
X23 may be valine or arginine;
X24 may be glutamine or leucine;
X27 may be methionine;
X28 may be asparagine or arginine;
X29 may be threonine; and
X30 may be absent.

For example, the peptide may be one which includes an amino acid sequence selected from the group consisting of SEQ ID NOS: 14, 16, 18, 19, 25, and 31, and specifically, one which (essentially) consists of an amino acid sequence selected from the group consisting of SEQ ID NOS: 14, 16, 18, 19, 25, and 31, but is not limited thereto.

More specifically, the peptide may be a peptide which includes the amino acid sequence of the following General Formula 2:

(General Formula 2, SEQ ID NO: 46)
Y-Aib-QGTF-X7-SD-X10-S-X12-Y-L-X15-X16-X17-R-A-X20-X21-F-V-X24-W-L-M-N-T-X30

In General Formula 2,
X7 may be threonine, valine, or cysteine;
X10 may be tyrosine or cysteine;
X12 may be lysine or cysteine;
X15 may be aspartic acid or cysteine;
X16 may be glutamic acid or serine;
X17 may be lysine or arginine;
X20 may be glutamine or lysine;
X21 may be aspartic acid or glutamic acid;
X24 may be valine or glutamine; and
X30 may be cysteine or may be absent.

For example, the peptide may be one which includes an amino acid sequence selected from the group consisting of SEQ ID NOS: 12, 13, 15, and 36 to 44, and specifically, one which (essentially) consists of an amino acid sequence selected from the group consisting of SEQ ID NOS: 12, 13, 15, and 36 to 44, but is not limited thereto. More specifically, the peptide may be one which includes an amino acid sequence of SEQ ID NO: 12, SEQ ID NO: 20, or SEQ ID NO: 37, or (essentially) consists of the corresponding amino acid sequence, but is not limited thereto.

Specifically, in General Formula 2,

X7 may be threonine, valine, or cysteine;
X10 may be tyrosine or cysteine;
X12 may be lysine;
X15 may be aspartic acid;
X16 may be glutamic acid or serine;
X17 may be lysine or arginine;
X20 may be glutamine or lysine;
X21 may be aspartic acid or glutamic acid;
X24 may be glutamine; and
X30 may be cysteine or may be absent, but is not particularly limited thereto.

For example, the peptide may be one which includes an amino acid sequence selected from the group consisting of SEQ ID NOS: 12, 36 to 38, 40 to 42, and 44, and specifically, one which (essentially) consists of an amino acid sequence selected from the group consisting of SEQ ID NOS: 12, 36 to 38, 40 to 42, and 44, but is not limited thereto.

However, among the isolated peptides, the peptides corresponding to SEQ ID NOS: 2 to 11, 14, 16 to 35, 49, and 50, and specifically, the peptides corresponding to SEQ ID NOS: 19, 33, 49, and 50 may be excluded from the claimed scope, but is not particularly limited thereto, and all of the peptides described in claims must belong to the scope of the present invention unless specified otherwise.

The glucagon derivative described above may include an intramolecular bridge (e.g., covalent crosslinking or non-covalent crosslinking), and specifically, may be in a form including a ring. For example, the glucagon derivative may be in a form where a ring is formed between the 16$^{th}$ and 20$^{th}$ amino acids of the glucagon derivative, but it is not particularly limited thereto.

Non-limiting examples of the ring may include a lactam crosslinking (or a lactam ring).

Additionally, the glucagon derivative includes all of those which are modified to include an amino acid capable of forming a ring at the desired site so as to include a ring.

The ring may be formed between side chains of amino acids within the glucagon derivative (e.g., in the form of a ring formation between a side chain of lysine and a side chain of a glutamic acid), but is not particularly limited thereto.

For example, the peptide including the amino acid sequence of General Formula 1 or 2 may be one in which each amino acid in each amino acid pair among the amino acid pairs of X10 and X14, X12 and X16, X16 and X20, X17 and X21, X20 and X24, and X24 and X28 in General Formula 1 or 2 may be substituted with glutamic acid or lysine, respectively, but is not limited thereto. In the $X_n$ (n is an integer), n refers to the position of the amino acid from the N-terminus of an amino acid sequence provided.

Additionally, the peptide including the amino acid sequence of General Formula 1 or 2 may be one in which each amino acid in each amino acid pair of X12 and X16 or the amino acid pair of X16 and X20 or the amino acid pair of X17 and X21 is respectively substituted with glutamic acid or lysine, which is capable of forming a ring.

Additionally, in General Formula 1 or 2, the peptide may be one in which a ring (e.g., a lactam ring) is formed between each amino acid in each amino acid pair among the amino acid pairs of X10 and X14, X12 and X16, X16 and X20, X17 and X21, X20 and X24, and X24 and X28, but is not limited thereto.

Additionally, in General Formula 1 or 2, X16 may be glutamic acid, X20 may be lysine, and the side chains of X16 and X20 may form a lactam ring, but they are not limited thereto.

Additionally, the peptide according to the present invention may be in the form where the N-terminus and/or C-terminus is not modified, however, those variants, where the amino terminus and/or carboxy terminus, etc., of the peptide is chemically modified or protected by organic groups, or amino acids added to the end of the peptide for its protection from proteases in vivo while increasing its stability, may also be included in the scope of the peptides of the present invention. In a case where the C-terminus is not modified, the end of the peptide according to the present invention may have a carboxyl group, but is not particularly limited thereto.

In particular, in the case of a chemically-synthesized peptide, its N- and C-termini are electrically charged and thus the N- and C-termini of the peptide may be acetylated and/or amidated, but the peptide is not particularly limited thereto.

Unless specified otherwise in the present invention, the description in the detailed description or claims with respect to "the peptide" according to the present invention or a "conjugate", in which such a peptide is covalently linked to a biocompatible material, may be applied to the forms, which include not only include the corresponding peptide or conjugate but also the salts of the corresponding peptide or conjugate (e.g., pharmaceutically acceptable salts thereof), or solvates thereof. Accordingly, even in a case where a "peptide" or "conjugate" is described in the present invention, the description may also be equally applied to a particular salt thereof, a particular solvate thereof, and a particular solvate of the particular salt thereof. These salts may be, for example, in a form where any pharmaceutically acceptable salts are used. The kind of the salt is not particularly limited. However, the salt is preferably one that is safe and effective to a subject, e.g., a mammal, but is not particularly limited thereto.

The term "pharmaceutically acceptable" refers to a material which can be effectively used for the intended use within the scope of pharmaco-medical decision without inducing excessive toxicity, irritation, allergic responses, etc.

As used herein, the term "pharmaceutically acceptable salt" refers to a salt derived from pharmaceutically acceptable inorganic salts, organic salts, or bases. Examples of the suitable salts may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzenesulfonic acid, etc. Examples of the salts derived from suitable bases may include alkali metals such as sodium, potassium, etc.; alkali earth metals such as magnesium; ammonium, etc.

Additionally, as used herein, the term "solvate" refers to a complex formed between the peptide, conjugate, or a salt thereof according to the present invention and a solvent molecule.

Additionally, the peptide of the present invention may be synthesized by a method well-known in the art, according to its length, e.g., by an automatic peptide synthesizer, and may be produced by genetic engineering technology.

Specifically, the peptide of the present invention may be prepared by a standard synthesis method, a recombinant expression system, or any other method known in the art. Accordingly, the glucagon derivative of the present invention may be synthesized by various methods including, for example, the methods described below:

(a) a method of synthesizing a peptide by a solid-phase or liquid-phase method stepwise or by fragment assembly, followed by isolation and purification of the final peptide product; or (b) a method of expressing a nucleic acid construct encoding a peptide in a host cell and recovering the expression product from the host cell culture; or (c) a method of performing an in vitro cell-free expression of a nucleic acid construct encoding a peptide and recovering the expression product therefrom; or a method of obtaining peptide fragments by any combination of the methods (a), (b), and (c), obtaining the peptide by linking the peptide fragments, and then recovering the peptide.

In a more specific example, a desired glucagon derivative may be produced by genetic manipulation, which includes preparing a fusion gene encoding a fusion protein, including a fusion partner and a glucagon derivative, transforming the resultant into a host cell, expressing in the form of a fusion protein, and cleaving the glucagon derivative from the fusion protein using a protease or a compound which is capable of protein cleavage followed by separation. For this purpose, for example, an amino acid residue-encoding DNA sequence that can be cleaved by a protease such as Factor Xa or enterokinase, CNBr, or a compound such as hydroxylamine, may be inserted between the fusion partner and a polynucleotide encoding a glucagon derivative.

In a more specific embodiment, a glucagon derivative, for example, a peptide including the amino acid sequence of General Formula 1 or 2, may be in the form of a long-acting conjugate in which a biocompatible material moiety capable of increasing in vivo half-life of the peptide is linked to the peptide, but is not limited thereto. The biocompatible material moiety may be interchangeably used with a carrier.

Specifically, the conjugate includes a peptide moiety and a biocompatible material moiety which is covalently linked to the peptide moiety, and the peptide moiety may be a sequence which is the same as the amino acid sequence of General Formula 1 or 2, or a sequence including the same.

As used herein, the term "long-acting conjugate", being in the form where a biocompatible material moiety or carrier is linked to a physiologically active material (e.g., a glucagon derivative, insulinotropic peptide, etc.), refers to a conjugate which exhibits an enhanced efficacy of duration (e.g., an increase of in vivo half-life) compared to that of a physiologically active material to which a biocompatible material moiety or carrier is not linked. In the long-acting conjugate, the biocompatible material moiety or carrier may be one that is covalently linked to the physiologically active material, but is not particularly limited thereto.

In a specific embodiment of the present invention, the duration of efficacy of the above conjugate of a glucagon derivative may increase compared to native glucagon or a glucagon derivative thereof, to which a carrier is not linked.

As used herein, the term "biocompatible material moiety" refers to a material which can be linked to a physiologically active material (e.g., a glucagon derivative, insulinotropic peptide, etc.) and thereby enhance the efficacy of duration compared to a physiologically active material to which a biocompatible material moiety or carrier is not linked. The biocompatible material moiety may be one that is covalently linked to the physiologically active material, but is not particularly limited thereto.

Examples of the biocompatible material moiety may include a polymer, fatty acid, cholesterol, albumin and a fragment thereof, an albumin-binding material, a polymer of repeating units of a particular amino acid sequence, an antibody, an antibody fragment, an FcRn-binding material, in vivo connective tissue or a derivative thereof, a nucleotide, fibronectin, transferrin, a saccharide, heparin, and elastin, but are not limited thereto.

Examples of the polymer may be those selected from the group consisting of a polyethylene glycol, a polypropylene glycol, an ethylene glycol-propylene glycol copolymer, polyoxyethylated polyol, polyvinyl alcohol, a polysaccharide, dextran, polyvinyl ethyl ether, a biodegradable polymer, a lipid polymer, chitin, hyaluronic acid, an oligonucleotide, and a combination thereof, but is not particularly limited thereto.

The polyethylene glycol is a general term including all of the forms of homopolymers of ethylene glycol, PEG copolymers, and monomethyl-substituted PEG polymers (mPEG), but is not particularly limited thereto.

Additionally, the biocompatible material moiety may include poly-amino acids such as poly-lysine, poly-aspartic acid, and poly-glutamic acid, but is not limited thereto.

Additionally, the fatty acid may be one having a binding affinity to albumin in vivo, but is not particularly limited thereto.

In a more specific embodiment, the FcRn-binding material may be an immunoglobulin Fc region, and more specifically, an IgG Fc region, but is not particularly limited thereto.

At least one amino acid side chain within the peptide of the present invention may be attached to the biocompatible material moiety in order to increase in vivo solubility and/or half-life, and/or increase bioavailability thereof. These modifications can reduce the clearance of therapeutic proteins and peptides.

The biocompatible material moiety may be soluble (amphipathic or hydrophilic) and/or non-toxic and/or pharmaceutically acceptable.

It is a known fact to a skilled person in the art that the thus-modified glucagon derivative can exhibit a superior therapeutic effect compared to native glucagon. Accordingly, the variants of the glucagon derivative as described above also belong to the scope of the present invention.

The biocompatible material moiety may be directly attached to the glucagon derivative or linked thereto through a linker. When the biocompatible material moiety is linked to the glucagon derivative directly or via a linker, the linkage may be a covalent bond.

Specifically, the linker may be a peptide linker or non-peptide linker.

When linker is a peptide linker it can include one or more amino acids, for example, 1 to 1000 amino acids, but is not particularly limited thereto. In the present invention, various known peptide linkers may be used (e.g., including [GS]x linker, [GGGS (SEQ ID NO: 51)]x linker, and [GGGGS (SEQ ID NO: 52)]x linker, etc., wherein x is a natural number of at least 1), but the peptide linkers are not limited thereto.

As used herein, "non-peptide linker" includes a biocompatible polymer in which at least two repeating units are linked. The repeating units are linked with each other by any covalent bond instead of a peptide bond. The non-peptide linker may be one constitution that establishes a moiety of a long-acting conjugate of the present invention.

As used herein, the term "non-peptide linker" may be used interchangeably with "non-peptide polymer".

In a specific embodiment, the biocompatible material moiety and the peptide may be covalently linked through a non-peptide linker which includes a reactive group that can be linked to the biocompatible material moiety (specifically, an immunoglobulin Fc region) and the peptide at both ends thereof, respectively.

Specifically, the non-peptide linker may be one selected from the group consisting of fatty acid, a saccharide, a polymer, a low molecular weight compound, a nucleotide, and a combination thereof.

Although not particularly limited, the molecular weight of the non-peptide polymer to be used in the present invention may be in the range of greater than 0 kDa to about 100 kDa or less, specifically, about 1 kDa to about 100 kDa, and more specifically, about 1 kDa to about 20 kDa, but is not limited thereto.

Although not particularly limited, the non-peptide linker may be one selected from the group consisting of a polyethylene glycol, a polypropylene glycol, an ethylene glycol-propylene glycol copolymer, polyoxyethylated polyol, polyvinyl alcohol, a polysaccharide, dextran, polyvinyl ethyl ether, a biodegradable polymer such as polylactic acid (PLA) and polylactic-glycolic acid (PLGA), lipid polymer, chitin, hyaluronic acid, an oligonucleotide, and a combination thereof.

In a more specific embodiment, the non-peptide polymer may be polyethylene glycol, but is not limited thereto. Additionally, the derivatives which are already known in the art and the derivatives which can be easily prepared at the level of the technology in the art belong to the scope of the present invention.

The non-peptide linker to be used in the present invention may be any polymer which has a resistance to in vivo proteases, without limitation. The molecular weight of the non-peptide polymer may be in the range of greater than 0 kDa to about 100 kDa or less, specifically about 1 kDa to about 100 kDa, and more specifically, about 1 kDa to about 20 kDa, but is not limited thereto. Additionally, the non-peptide linker of the present invention, which is linked to the polypeptide including the immunoglobulin Fc region, may include not only a single kind of a polymer but also a combination of different kinds of polymers.

As used herein, the term "about" refers to a range including all of ±0.5, ±0.4, ±0.3, ±0.2, ±0.1, etc., and it includes all of the values equivalent to those which come immediately after the term "above" or those in a similar range.

Specifically, the linker may be one that is respectively linked to the peptide moiety and the biocompatible material moiety through covalent bonds, which were respectively formed when one end of the linker reacted with an amine group or thiol group of the biocompatible material moiety while the other end of the linker reacted with an amine group or thiol group of the peptide moiety (i.e., the peptide moiety including the amino acid sequence of General Formula 1 or 2).

In a specific embodiment, one end of the non-peptide linker may be linked to an amine group or thiol group of an immunoglobulin Fc region while the other end of the non-peptide linker may be linked to an amine group or thiol group of a glucagon derivative. Specifically, the non-peptide polymer may include a reactive group at both ends thereof, respectively, which can be linked to a biocompatible material moiety, specifically an immunoglobulin Fc region, and a glucagon derivative; for example, a reactive group which can respectively form a covalent bond to be linked to the biocompatible material and the glucagon derivative by reacting with an amine group of N-terminus or lysine of the glucagon derivative, or a thiol group of cysteine of the glucagon derivative, an amine group of N-terminus or lysine of the biocompatible material or a thiol group of cysteine of the biocompatible material (e.g., the immunoglobulin Fc region), but is not limited thereto.

Additionally, the reactive end group of the non-peptide polymer that can be linked to the biocompatible material moiety, specifically the immunoglobulin Fc region and the glucagon derivative may be selected from the group consisting of an aldehyde group, a maleimide group, and a succinimide derivative, but is not limited thereto.

In the above, examples of the aldehyde group may include a propionaldehyde group or a butyraldehyde group, but are not limited thereto.

In the above, as a succinimide derivative, succinimidyl valerate, succinimidyl methylbutanoate, succinimidyl methylpropionate, succinimidyl butanoate, succinimidyl propionate, N-hydroxysuccinimide, hydroxy succinimidyl, succinimidyl carboxymethyl, or succinimidyl carbonate may be used, but is not limited thereto.

Additionally, the final product produced through reductive amination via an aldehyde bond is more stable than that linked by an amide bond. The aldehyde reactive group selectively reacts with a N-terminus at a low pH condition while it can form a covalent bond with a lysine residue at high pH, e.g., pH 9.0.

The reactive groups at both ends of the non-peptide linker may be the same as or different from each other, for example, a maleimide reactive group may be provided at one end and an aldehyde group, a propionaldehyde group, or a butyraldehyde group may be provided at the other end. However, if an immunoglobulin Fc region and a glucagon derivative can be conjugated at each end of the non-peptide linker, it is not particularly limited.

For example, the non-peptide polymer may possess a maleimide group at one end and an aldehyde group, a propionaldehyde group, or a butyraldehyde group at the other end.

When a polyethylene glycol having a reactive hydroxy group at both ends thereof is used as the non-peptide polymer, the hydroxy group may be activated to various reactive groups by known chemical reactions, or a polyethylene glycol having a commercially available modified reactive group may be used so as to prepare the long-acting protein conjugate of the present invention.

In a specific embodiment, the non-peptide polymer may be one which can be linked to a cysteine residue of a glucagon derivative, and more specifically, to the —SH group of cysteine, but is not limited thereto. In particular, the non-peptide polymer may be polyethylene glycol, but is not particularly limited thereto, and other kinds of non-peptide polymers described previously may also be included therein.

In a specific embodiment, the conjugate may be one in which a peptide including the amino acid sequence of SEQ ID NO: 12, SEQ ID NO: 20, or SEQ ID NO: 37 is linked to the immunoglobulin Fc region by a non-peptide polymer, and in particular, the non-peptide polymer may be one which is linked to the cysteine residue located on the $30^{th}$ of the amino acid sequence of SEQ ID NO: 12, the cysteine residue located on the $17^{th}$ of the amino acid sequence of SEQ ID NO: 20, or the cysteine residue located on the $30^{th}$ of the amino acid sequence of SEQ ID NO: 37, but is not limited thereto. In particular, the non-peptide polymer may be polyethylene glycol, but is not particularly limited thereto, and other kinds of non-peptide polymers described previously may also be included therein.

When maleimide-PEG-aldehyde is used, the maleimide group may be linked to the —SH group of the glucagon derivative by a thioether bond and the aldehyde group may be linked to the —NH$_2$ of the immunoglobulin Fc through reductive amination, but is not limited thereto and the above is merely an embodiment.

Additionally, in the above conjugate, the reactive group of the non-peptide polymer may be one that is linked to NH$_2$ located at the N-terminus of the immunoglobulin Fc region, but this is merely an exemplary embodiment.

In the present invention, "immunoglobulin Fc region" refers to a region including the heavy chain constant region 2 (CH2) and/or the heavy chain constant region 3 (CH3), excluding the heavy chain and light chain variable regions of an immunoglobulin. The immunoglobulin Fc region may be one constitution that establishes a moiety of a protein conjugate of the present invention.

The immunoglobulin Fc region may include a hinge region in the heavy chain constant region, but is not limited thereto. Additionally, the immunoglobulin Fc region of the present invention may be an extended Fc region including a part or the entirety of the heavy chain constant region 1 (CH1) and/or the light chain constant region 1 (CL1), excluding the heavy chain and the light chain variable regions of the immunoglobulin, as long as the immunoglobulin Fc region has an effect substantially the same as or improved compared to the native type. Additionally, the immunoglobulin Fc region of the present invention may be a region in which a fairly long part of the amino acid sequence corresponding to CH2 and/or CH3 is removed.

For example, the immunoglobulin Fc region of the present invention may be 1) a CH1 domain, a CH2 domain, a CH3 domain, and a CH4 domain; 2) a CH1 domain and a CH2 domain; 3) a CH1 domain and a CH3 domain; 4) a CH2 domain and a CH3 domain; 5) a combination between one or two or more domains among a CH1 domain, a CH2 domain, a CH3 domain, and a CH4 domain and an immunoglobulin hinge region (or a part of the hinge region); and 6) a dimer between each domain of the heavy chain constant region and the light chain constant region, but is not limited thereto.

Additionally, in a specific embodiment, the immunoglobulin Fc region may be in a dimeric form, and one molecule of a glucagon derivative may be covalently linked to a Fc region in a dimeric form, and in particular, the immunoglobulin Fc and the glucagon derivative may be interlinked by a non-peptide polymer. Furthermore, two molecules of the glucagon derivative may be possibly conjugated in a symmetrical manner to a single Fc region in a dimeric form. In particular, the immunoglobulin Fc and the glucagon derivative or the insulinotropic peptide may be interlinked by a non-peptide linker, but are not limited to the embodiment described above.

Additionally, the immunoglobulin Fc region of the present invention not only includes a native amino acid sequence but also a sequence derivative thereof. An amino acid sequence derivative refers to an amino acid sequence which has a difference in at least one amino acid residue due to deletion, insertion, non-conservative or conservative substitution, or a combination thereof.

For example, the amino acid residues at positions 214 to 238, 297 to 299, 318 to 322, or 327 to 331, which are known to be in the binding of an immunoglobulin Fc, may be used as suitable sites for modification.

Additionally, other various derivatives are possible, including one that has a deletion of a region capable of forming a disulfide bond, or a deletion of some amino acid residues at the N-terminus of native Fc or an addition of a methionine residue at the N-terminus of native Fc. Further, to remove effector functions, a deletion may occur in a complement-binding site, such as a C1q-binding site and an antibody dependent cell mediated cytotoxicity (ADCC) site. Techniques of preparing such sequence derivatives of the immunoglobulin Fc region are disclosed in International Patent Publication Nos. WO 97/34631, WO 96/32478, etc.

Amino acid exchanges in proteins and peptides, which do not generally alter the activity of the proteins or peptides, are known in the art (H. Neurath, R. L. Hill, *The Proteins*, Academic Press, New York, 1979). The most commonly occurring exchanges are Ala/Ser, Asp/Glu, Thr/Ser, Ala/Gly, Ala/Thr, Ser/Asn, Ser/Gly, Thy/Phe, Ala/Pro, Lys/Arg, Asp/Asn, Leu/Ile, Leu/Val, Ala/Glu, and Asp/Gly, in both directions. In addition, the Fc region may, if necessary, be modified by phosphorylation, sulfation, acrylation, glycosylation, methylation, farnesylation, acetylation, amidation, etc.

The above-described Fc derivatives show biological activity identical to that of the Fc region of the present invention and have improved structural stability against heat, pH, etc.

Further, the immunoglobulin Fc region may be obtained from native forms isolated in vivo from humans or animals such as cows, goats, pigs, mice, rabbits, hamsters, rats, guinea pigs, etc., or may be recombinants or derivatives thereof, obtained from transformed animal cells or microorganisms. Herein, the Fc region may be obtained from a native immunoglobulin by isolating a whole immunoglobulin from a living human or animal body and treating the isolated immunoglobulin with protease. When the whole immunoglobulin is treated with papain, it is cleaved into Fab and Fc regions, whereas when the whole immunoglobulin is treated with pepsin, it is cleaved into pF'c and F(ab)$_2$ fragments. Fc or pF'c can be isolated using size exclusion chromatography, etc. In a more specific embodiment, a human-derived Fc region is a recombinant immunoglobulin Fc region obtained from a microorganism.

In addition, the immunoglobulin Fc region may have natural glycans, increased or decreased glycans compared to the natural type, or be in a deglycosylated form. The increase, decrease, or removal of the glycans of the immunoglobulin Fc may be achieved by conventional methods such as a chemical method, an enzymatic method, and a genetic engineering method using a microorganism. The immunoglobulin Fc region obtained by removal of glycans from the Fc region shows a significant decrease in binding affinity to the C1q part and a decrease or loss in antibody-dependent cytotoxicity or complement-dependent cytotoxicity, and thus it does not induce unnecessary immune responses in vivo. In this regard, an immunoglobulin Fc region in a deglycosylated or aglycosylated immunoglobulin Fc region may be a more suitable form to meet the original object of the present invention as a drug carrier.

As used herein, the term "deglycosylation" refers to enzymatically removing sugar moieties from an Fc region, and the term "aglycosylation" refers to an unglycosylated Fc region produced in prokaryotes, more specifically, *E. coli*.

Meanwhile, the immunoglobulin Fc region may be derived from humans or other animals including cows, goats, pigs, mice, rabbits, hamsters, rats, and guinea pigs. In a more specific embodiment, it is derived from humans.

In addition, the immunoglobulin (Ig) Fc region may be derived from IgG, IgA, IgD, IgE, IgM, or a combination or hybrid thereof. In a more specific embodiment, it is derived from IgG or IgM, which are among the most abundant proteins in human blood, and in an even more specific embodiment, it is derived from IgG, which is known to enhance the half-lives of ligand-binding proteins. In a yet even more specific embodiment, the immunoglobulin Fc region is an IgG4 Fc region, and in the most specific embodiment, the IgG4 Fc region is an aglycosylated Fc region derived from human IgG4, but is not limited thereto.

In particular, as used herein, the term "combination" means that polypeptides encoding single-chain immunoglobulin Fc: regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

The composition of the present invention can be used for preventing or treating congenital hyperinsulinism, hypoglycemia, or metabolic syndrome.

As used herein, the term "prevention" refers to all kinds of actions associated with the inhibition or delay of the occurrence of the target disease (e.g., congenital hyperinsulinism, hypoglycemia, or metabolic syndrome) by the administration of the glucagon derivative, a conjugate containing the same, or the composition, and the term "treatment" refers to all kinds of actions associated with the improvement or advantageous changes in symptoms of the target disease (e.g., congenital hyperinsulinism, hypoglycemia, or metabolic syndrome) by the administration of the glucagon derivative, a conjugate containing the same, or the composition.

As used herein, the term "administration" refers to an introduction of a particular material to a patient by an appropriate manner. The composition may be administered by a general route that enables the delivery of the composition to a target tissue in vivo, for example, intraperitoneal, intravenous, intramuscular, subcutaneous, intradermal, oral, topical, intranasal, intrapulmonary, and intrarectal administration, but is not particularly limited thereto.

As used herein, the term "hypoglycemia" refers to a health state, in which blood glucose levels are lower than those of normal people, and in general, refers to a state when the blood glucose levels are 50 mg/dL or less, but is not particularly limited thereto. Hypoglycemia is frequently caused when a person who takes an oral hypoglycemic agent or insulin has eaten less than usual or has performed activities or exercised more than usual. Additionally, hypoglycemia may occur due to drinking of alcohols, use of glucose level-lowering drugs, severe physical diseases, hormone deficiency such as adrenocortical hormones and glucagon, tumor in insulin-producing pancreas, insulin autoimmune disease, gastrectomy patients, inborn error of carbohydrate metabolism disorder, etc.

In the present invention, the hypoglycemia includes both acute and chronic hypoglycemia.

Symptoms of hypoglycemia include weakness, trembling, pale skin, cold sweat, dizziness, excitement, anxiety, pounding heart, empty stomach, headache, fatigue, etc. In the case of persistent hypoglycemia, it may lead to convulsion or seizure, and may cause shock and thus fainting.

More specifically, the hypoglycemia may be caused by persistent hyperinsulinism due to a genetic defect. Examples of known causes of hyperinsulinism due to a genetic defect may include a mutation on SUR gene or Kir6.2 gene localized on chromosome 11p15.1, or an increase of glucokinase (GK) activity due to a mutation on GK gene localized on chromosome 7p15-p13, an increase of ATP in islet cells due to a mutation on glutamate dehydrogenase (GDH) gene, etc.

Meanwhile, congenital hyperinsulinism is one of the leading causes of severe and persistent hypoglycemia in newborns and children. It may be caused by an abnormal function of pancreatic cells due to a temporary increase of insulin secretion or genetic mutation in low-birth-weight infants or infants from diabetic mothers, etc. It is known that glucagon may be used for the treatment of the congenital hyperinsulinism.

Additionally, the glucagon derivative or a conjugate containing the same may be used for preventing or treating hypoglycemia.

Additionally, the glucagon derivative or a conjugate containing the same of the present invention may be used as a pharmaceutical medicament not only for preventing body weight increase, promoting body weight decrease, reducing overweight, and treating obesity including morbid obesity (e.g., by controlling appetite, ingestion, food intake, calorie intake, and/or energy consumption), but also for treating obesity-related inflammation, obesity-related gallbladder disease, and obesity-induced sleep apnea, but is not limited thereto, and may be used for treating the associated diseases or health conditions thereof. The glucagon derivative of the present invention or a conjugate containing the same may also be used for treating metabolic syndrome other than obesity, i.e., obesity-related diseases such as impaired glucose tolerance, hypercholesterolemia, dyslipidemia, obesity, diabetes, hypertension, nonalcoholic steatohepatitis (nonalcoholic steatohepatitis, NASH), atherosclerosis caused by dyslipidemia, atherosclerosis, arteriosclerosis, coronary heart disease, stroke, etc. However, the effects of the peptide according to the present invention may be mediated entirely or partially by the body weight-related effects described above or may be independent of the same.

As used herein, the term "metabolic syndrome" refers to a symptom where various diseases that occur due to chronic metabolic disorder occur alone or in combination. In particular, examples of diseases that belong to metabolic syndrome may include impaired glucose tolerance, hypercholesterolemia, dyslipidemia, obesity, diabetes, hypertension, nonalcoholic steatohepatitis (NASH), arteriosclerosis due to dyslipidemia, atherosclerosis, arteriosclerosis, coronary heart disease, stroke, etc., but are not limited thereto.

As used herein, the term "obesity" refers to a medical condition with excess body fat accumulation and people are generally defined to be obese when their body mass index (BMI; a value of body mass (kg) over body height squared (m)) is 25 or higher. Obesity is most commonly caused by energy imbalance due to excessive food intake compared to energy consumption over a long period of time. Obesity, being a metabolic disease that affects the entire body, increases the possibility of developing diabetes and hyperlipidemia, increases the risk of the incidence of sexual dysfunction, arthritis, and cardiovascular disease, and is associated with cancer development in some cases.

The glucagon derivative according to the present invention has an altered pI and thus can exhibit improved solubility and higher stability at a neutral pH condition compared to native glucagon. Additionally, the glucagon derivative according to the present invention can exhibit an activity on a glucagon receptor and thus can be effectively used for preventing or treating target diseases including hypoglycemia, metabolic syndrome, and congenital hyperinsulinism.

The pharmaceutical composition of the present invention may contain a pharmaceutically acceptable carrier, excipient, or diluent. As used herein, the term "pharmaceutically acceptable" refers to the properties of having a sufficient amount to exhibit a therapeutic effect and not causing adverse effects, and may be easily determined by a skilled person in the art based on the factors well known in the medical field, such as the kind of disease, age, body weight, health status, sex, drug sensitivity of a patient, administration route, administration method, administration frequency, duration of treatment, a drug to be mixed or administered simultaneously in combination, etc.

The pharmaceutical composition of the present invention containing the peptide or a conjugate containing the same of the present invention may further contain a pharmaceutically acceptable carrier. The pharmaceutically acceptable carrier may include, for oral administration, a binder, a glidant, a disintegrant, an excipient, a solubilizing agent, a dispersant, a stabilizing agent, a suspending agent, a coloring agent, a flavoring agent, etc.; for injections, a buffering agent, a preserving agent, an analgesic, a solubilizing agent, an isotonic agent, a stabilizing agent, etc., which may be combined to be used; and for topical administrations, a base, an excipient, a lubricant, a preserving agent, etc., although it is not limited thereto.

The formulation type of the composition according to the present invention may be prepared variously by combining with a pharmaceutically acceptable carrier as described above. For example, for oral administration, the composition may be formulated into tablets, troches, capsules, elixirs, suspensions, syrups, wafers, etc. For injections, the composition may be formulated into single-dose ampoules or multidose containers. The composition may be also formulated into solutions, suspensions, tablets, capsules, and sustained-release formulations.

Meanwhile, examples of suitable carriers, excipients, and diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. Additionally, the composition may further contain a filler, an anti-coagulant, a lubricant, a humectant, a flavoring agent, a preservative, etc.

Additionally, the pharmaceutical composition of the present invention may be prepared in any formulation type selected from the group consisting of tablets, pills, powders, granules, capsules, suspensions, liquid medicine for internal use, emulsions, syrups, sterile injection solutions, non-aqueous solvents, lyophilized formulations, and suppositories.

Additionally, the composition may be formulated into a single dosage form suitable for the patient's body, and specifically, it is formulated into a preparation useful for peptide drugs according to the typical method used in the pharmaceutical field to be administered by an oral or parenteral route, such as through skin, intravenously, intramuscularly, intra-arterially, intramedullarily, intrathecally, intraventricularly, pulmonarily, transdermally, subcutaneously, intraperitoneally, intranasally, intragastrically, topically, sublingually, vaginally, or rectally, but is not limited thereto.

Additionally, the peptide or conjugate may be used by blending with various pharmaceutically acceptable carriers such as physiological saline or organic solvents. In order to increase the stability or absorptivity, carbohydrates such as glucose, sucrose, or dextrans; antioxidants such as ascorbic acid or glutathione; chelating agents; low molecular weight proteins; or other stabilizers may be used.

The administration dose and frequency of the pharmaceutical composition of the present invention are determined by the type of active ingredient(s), along with various factors, such as the disease to be treated, administration route, patient's age, sex, and body weight, and severity of the disease.

Although not particularly limited thereto, the pharmaceutical composition of the present invention may contain the above ingredient (active ingredient) in an amount of 0.01% (W/V) to 99% (W/V).

The total effective dose of the composition of the present invention may be administered to a patient in a single dose, or may be administered for a long period of time in multiple doses according to a fractionated treatment protocol. In the pharmaceutical composition of the present invention, the content of active ingredient(s) may vary depending on the disease severity. Specifically, the preferable total daily dose of the peptide or conjugate of the present invention may be approximately 0.0001 µg to 500 mg per 1 kg of body weight of a patient. However, the effective dose of the peptide or conjugate is determined considering various factors including patient's age, body weight, health conditions, sex, disease severity, diet, and excretion rate, in addition to administration route and treatment frequency of the pharmaceutical composition. In this regard, those skilled in the art may easily determine the effective dose suitable for the particular use of the pharmaceutical composition of the present invention. The pharmaceutical composition according to the present invention is not particularly limited to the formulation and administration route and mode, as long as it shows the effects of the present invention.

The pharmaceutical composition of the present invention can exhibit excellent in vivo duration of efficacy and titer, and thus the number and frequency of administration can be significantly reduced compared to other pharmaceutical preparations, but is not particularly limited thereto.

In particular, since the pharmaceutical composition of the present invention contains, as an active ingredient, a glucagon derivative having an altered pI different from that of native glucagon, it shows improved solubility and/or high stability according to the pH of a given solution, and thus the pharmaceutical composition of the present invention can be effectively used in the preparation of a stable glucagon formulation for treating target diseases including congenital hyperinsulinism, hypoglycemia, or metabolic syndrome.

With regard to a pharmaceutical composition for preventing or treating metabolic syndrome, or a therapy for preventing or treating metabolic syndrome, the pharmaceutical composition may further contain a compound or material that has a therapeutic activity with regard to metabolic syndrome, and the therapy may further include the use of the above compound or material.

Examples of the compound or material having a therapeutic activity for metabolic syndrome to be included in the combined administration or the composition of the present invention may include an insulinotropic peptide, a glucagon like peptide-1 (GLP-1) receptor agonist, a leptin receptor agonist, a dipeptidyl peptidase-IV (DPP-IV) inhibitor, a Y5 receptor antagonist, a melanin-concentrating hormone (MCH) receptor antagonist, a Y2/4 receptor agonist, a melanocortin 3/4 (MC 3/4) receptor agonist, a gastric/pancreatic lipase inhibitor, an agonist of 5-hydroxytryptamine receptor 2C (5HT2C), a β3A receptor agonist, an amylin receptor agonist, a ghrelin antagonist, a ghrelin receptor antagonist, a peroxisome proliferator-activated receptor alpha (PPARα) agonist, a peroxisome proliferator-activated receptor delta (PPARδ) agonist, a Farnesoid X receptor (FXR) agonist, an acetyl-CoA carboxylase inhibitor, a peptide YY, cholecystokinin (CCK), xenin, glicentin, obestatin, secretin, nesfatin, insulin, and a glucose-dependent insulinotropic peptide (GIP), but is not limited thereto. Additionally, all medicaments which are effective for obesity treatment and the medicaments capable of inhibiting hepatic inflammation and fibrosis may be included.

Specifically, the insulinotropic peptide may be selected from the group consisting of GLP-1, exendin-3, exendin-4, an agonist thereof, a derivative thereof, a fragment thereof, a variant thereof, and a combination thereof.

More specifically, the insulinotropic peptide may be an insulinotropic peptide derivative in which the N-terminal histidine residue of the insulinotropic peptide is substituted with one selected from the group consisting of desamino-histidyl, N-dimethyl-histidyl, β-hydroxy imidazopropionyl, 4-imidazoacetyl, and β-carboxy imidazopropionyl, but is not limited thereto. In particular, the insulinotropic peptide may be GLP-1, exendin-3, or exendin-4.

Even more specifically, the insulinotropic peptide may be selected from the group consisting of native exendin-4; an exendin-4 derivative in which the N-terminal amine group of exendin-4 is deleted; an exendin-4 derivative in which the N-terminal amine group of exendin-4 is substituted with a hydroxyl group; an exendin-4 derivative in which the N-terminal amine group of exendin-4 is modified with a dimethyl group; an exendin-4 derivative in which the α-carbon of the amino acid of exendin-4, histidine, is deleted; an exendin-4 derivative in which the 12$^{th}$ amino acid of exendin-4, lysine, is substituted with serine, and an exendin-4 derivative in which the 12$^{th}$ amino acid of exendin-4, lysine, is substituted with arginine, but is not limited thereto.

Meanwhile, as an example of the insulinotropic peptide or a long-acting conjugate thereof, the entire disclosure of U.S. Patent Application Publication No. 2010-0105877 is enclosed in the present invention as a reference, but is not limited thereto.

Additionally, the insulinotropic peptide may be in the form of a conjugate which includes a peptide moiety, that includes the amino acid sequence of the above-mentioned insulinotropic peptide, and a biocompatible material moiety linked to the peptide moiety, but is not limited thereto. Specifically, the peptide moiety that includes the amino acid sequence of the insulinotropic peptide is characterized in that it is in the form of a conjugate covalently linked to the biocompatible material moiety through a linker, but is not particularly limited thereto. The conjugate of the insulinotropic peptide may be a long-acting conjugate, and the definition with regard to the long-acting type is the same as explained above.

For all features with regard to the conjugate, in particular, the biocompatible material moiety (immunoglobulin Fc) and linker (e.g., non-peptide polymer), all of those described previously will be applied. For example, the linker may be one that is respectively linked to the peptide moiety and the biocompatible material moiety through covalent bonds, which were respectively formed when one end of the linker reacted with an amine group or thiol group of the biocompatible material moiety while the other end of the linker reacted with an amine group or thiol group of the peptide moiety.

In a specific embodiment, one end of the non-peptide linker may react with an amine group or thiol group of an immunoglobulin Fc region while the other end of the linker react with an amine group or thiol group of the insulinotropic peptide and thereby form a covalent bond, respectively.

In a more specific embodiment, the composition for preventing or treating the above-mentioned metabolic syndrome or therapy may be a composition or therapy containing or using the peptide including the amino acid sequence of General Formula 2 below or the conjugate a biocompatible material moiety covalently linked to the peptide, but is not particularly limited thereto.

(General Formula 2, SEQ ID NO: 46)
Y-Aib-QGTF-X7-SD-X10-S-X12-Y-L-X15-X16-X17-R-A-X20-X21-F-V-X24-W-L-M-N-T-X30

In General Formula 2,
X7 is threonine, valine, or cysteine;
X10 is tyrosine or cysteine;
X12 is lysine or cysteine;
X15 is aspartic acid or cysteine;
X16 is glutamic acid or serine;
X17 is lysine or arginine;
X20 is glutamine or lysine;
X21 is aspartic acid or glutamic acid;
X24 is valine or glutamine; and
X30 is cysteine, or is absent.

The peptide according to the previous specific embodiment, when the amino acid sequence of General Formula 2 is identical to any one of SEQ ID NOS: 19, 33, 49, and 50, all or part of the peptides may be excluded.

More specifically, the composition may include both (i) a conjugate, which includes the peptide moiety including the amino acid sequence of SEQ ID NO: 37, and a biocompatible material moiety covalently linked to the peptide moiety; and (ii) a conjugate, which includes an imidazo-acetyl exendin-4 moiety where the α-carbon of the 1$^{st}$ amino acid of exendin-4 (i.e., histidine) is deleted and a biocompatible material moiety covalently linked to the imidazo-acetyl exendin-4 moiety. Even more specifically, the peptide moiety including the amino acid sequence of SEQ ID NO: 37 and the imidazo-acetyl exendin-4 moiety may be linked to their respective biocompatible material moietys through a linker, but are not particularly limited thereto.

The administration does of the compound or material having a therapeutic activity with regard to metabolic syndrome, specifically the conjugate where the insulinotropic peptide is linked to a biocompatible material moiety, may be in the range of about 0.0001 μg to about 500 mg per 1 kg of body weight of a patient, but is not particularly limited thereto.

Additionally, the pharmaceutical composition of the present invention may contain the above materials for combined administration, that is, the compound or material having a therapeutic activity with regard to metabolic syndrome and a glucagon derivative or a conjugate containing the same (or each ingredient of the above materials for combined administration), in an amount of 0.01% (W/V) to 99% (W/V).

Meanwhile, in an aspect, the compound or material having a therapeutic activity with regard to metabolic syndrome and a glucagon derivative or a conjugate containing the same, specifically a conjugate where a biocompatible material moiety is linked to the insulinotropic peptide (e.g., an insulinotropic peptide-PEG-IgFc conjugate) and a conjugate where a biocompatible material moiety is linked to a glucagon derivative may be used in a molar ratio of 1:0.01 to 1:50, but is not particularly limited thereto.

In another aspect, the present invention provides a kit including a glucagon derivative or a conjugate containing the same, and specifically, a kit for preventing or treating congenital hyperinsulinism, hypoglycemia, or metabolic syndrome including a glucagon derivative or a conjugate containing the same.

The glucagon derivative, or a conjugate containing the same, congenital hyperinsulinism, hypoglycemia, metabolic syndrome, prevention, or treatment are the same as explained above. The kinds of ingredients that may be further contained in the kit of the present invention may include all of those which may be contained in the composition explained above.

In particular, when the kit is a kit for preventing or treating metabolic syndrome, both (i) the glucagon derivative, specifically the peptide including the amino acid sequence of General Formula 1 or 2, or a conjugate containing the same, and (ii) an insulinotropic peptide, in particular GLP-1, exendin-3, exendin-4, or a derivative thereof, or a conjugate containing the same, but is not particularly limited thereto.

In another aspect, the present invention provides a glucagon derivative.

The glucagon derivative is the same as explained above.

More specifically, the derivative is characterized in that it is an isolated peptide including the amino acid sequence of General Formula 1 represented by SEQ ID NO: 45 described above. For the explanation and combination with regard to the isolated peptide including the amino acid sequence of General Formula 1, all of those described above will be applied.

The derivative is characterized in that it is an isolated peptide including the amino acid sequence of the following General Formula 2.

(General Formula 2, SEQ ID NO: 46)
Y-Aib-QGTF-X7-SD-X10-S-X12-Y-L-X15-X16-X17-R-A-
X20-X21-F-V-X24-W-L-M-N-T-X30

In General Formula 2,
X7 is threonine, valine, or cysteine;
X10 is tyrosine or cysteine;
X12 is lysine or cysteine;
X15 is aspartic acid or cysteine;
X16 is glutamic acid or serine;
X17 is lysine or arginine;
X20 is glutamine or lysine;
X21 is aspartic acid or glutamic acid;
X24 is valine or glutamine, and
X30 is cysteine, or is absent.

When the amino acid sequence of General Formula 2 is identical to any one of SEQ ID NOS: 19, 33, 49, and 50, it may be excluded.

More specifically, in the peptide including the amino acid sequence of General Formula 2, X16 may be glutamic acid X20 may be lysine, and the side chains of X16 and X20 may form a lactam ring, but is not limited thereto.

Additionally, the C-terminus of the peptide including the amino acid sequence of General Formula 2 may be amidated or unmodified, but is not limited thereto.

Additionally, the peptide may be a glucagon derivative capable of activating a glucagon receptor, but is not limited thereto.

More specifically, the peptide may include an amino acid sequence selected from the group consisting of SEQ ID NOS: 12, 13, 15, and 36 to 44, but is not limited thereto.

In still another aspect, the present invention provides an isolated polynucleotide encoding the glucagon derivative, a vector including the polynucleotide, and an isolated cell including the polynucleotide or the vector.

The glucagon derivative is the same as explained above. Specifically, the derivative may be an isolated peptide including the amino acid sequence of General Formula 1 represented by SEQ ID NO: 45 described above. For the explanation and combination with regard to the isolated peptide including the amino acid sequence of General Formula 1, all of those described above will be applied. Additionally, specifically, the derivative may be an isolated peptide including the amino acid sequence of General Formula 2 represented by SEQ ID NO: 46 described above. For the explanation and combination with regard to the isolated peptide including the amino acid sequence of General Formula 2, all of those described above will be applied.

As used herein, the term "homology" indicates sequence similarity with a wild-type amino acid sequence or wild-type nucleotide sequence, and the homology comparison may be done with the naked eye or using a commercially available comparison program. Using a commercially available computer program, the homology between two or more sequences may be expressed as a percentage (%), and the homology (%) between adjacent sequences may be calculated.

As used herein, the term "recombinant vector" refers to a DNA construct including the sequence of a polynucleotide encoding a target peptide, e.g., a glucagon derivative, which is operably linked to an appropriate regulatory sequence to enable the expression of the target peptide, e.g., a glucagon derivative, in a host cell.

The regulatory sequence includes a promoter capable of initiating transcription, any operator sequence for the regulation of the transcription, a sequence encoding an appropriate mRNA ribosome-binding domain, and a sequence regulating the termination of transcription and translation. The recombinant vector, after being transformed into a suitable host cell, may be replicated or function irrespective of the host genome, or may be integrated into the host genome itself.

The recombinant vector used in the present invention may not be particularly limited as long as the vector is replicable in the host cell, and it may be constructed using any vector known in the art. Examples of the vector conventionally used may include natural or recombinant plasmids, cosmids, viruses, and bacteriophages. The vectors to be used in the present invention may be any expression vector known in the art.

The recombinant vector is used for the transformation of a host cell for producing glucagon derivatives of the present invention. Additionally, these transformed cells, as a part of the present invention, may be used for the amplification of nucleic acid fragments and vectors, or may be cultured cells or cell lines used in the recombinant production of glucagon derivatives of the present invention.

As used herein, the term "transformation" refers to a process of introducing a recombinant vector including a polynucleotide encoding a target protein into a host cell, thereby enabling the expression of the protein encoded by the polynucleotide in the host cell. For the transformed polynucleotide, it does not matter whether it is inserted into the chromosome of a host cell and located thereon or located outside of the chromosome, as long as it can be expressed in the host cell, and both cases are included.

Additionally, the polynucleotide includes DNA and RNA which encode the target protein. The polynucleotide may be inserted in any form insofar as it can be introduced into a host cell and expressed therein. For example, the polynucleotide may be introduced into a host cell in the form of an expression cassette, which is a gene construct including all the essential elements required for self-expression. The expression cassette may conventionally include a promoter operably linked to the polynucleotide, a transcription termination signal, a ribosome-binding domain, and a translation termination signal. The expression cassette may be in the form of an expression vector capable of self-replication. Additionally, the polynucleotide may be introduced into a host cell as it is and operably linked to a sequence essential for its expression in the host cell, but is not limited thereto.

Additionally, as used herein, the term "operably linked" refers to a functional connection between a promoter sequence, which initiates and mediates the transcription of the polynucleotide encoding the target peptide of the present invention, and the above gene sequence.

An appropriate host to be used in the present invention may not be particularly limited as long as it can express the polynucleotide of the present invention. Examples of the appropriate host may include bacteria belonging to the genus *Escherichia* such as *E. coli*; bacteria belonging to the genus *Bacillus* such as *Bacillus subtilis*; bacteria belonging to the genus *Pseudomonas* such as *Pseudomonas putida*; yeasts such as *Pichia pastoris, Saccharomyces cerevisiae*, and *Schizosaccharomyces pombe*; insect cells such as *Spodoptera frugiperda* (Sf9), and animal cells such as CHO, COS, and BSC.

In still another aspect, the present invention provides an isolated conjugate in which a glucagon derivative is linked to a biocompatible material moiety which is capable of increasing in vivo half-life of the glucagon derivative. The conjugate may be a long-acting conjugate.

Specifically, the present invention provides an isolated conjugate which includes a peptide moiety and a biocompatible material moiety, and the peptide moiety is the same sequence as that of General Formula 1 or 2, or a sequence including the same.

With regard to the glucagon derivative, the amino acid sequence of General Formula 1 or 2, the biocompatible material, and the constitution of the conjugate, all of those described above are applied.

Specifically, the derivative may be an isolated peptide including the amino acid sequence of General Formula 1 represented by SEQ ID NO: 45 described above. For the feature and combination with regard to the isolated peptide including the amino acid sequence of General Formula 1, all of those described above are applied.

Additionally, specifically, the derivative may be an isolated peptide including the amino acid sequence of General Formula 2 represented by SEQ ID NO: 46 described above. For the feature and combination with regard to the isolated peptide including the amino acid sequence of General Formula 2, all of those described above are applied.

Specifically, the biocompatible material moiety may be selected from the group consisting of a polymer, fatty acid, cholesterol, albumin and a fragment thereof, an albumin-binding material, a polymer of repeating units of a particular amino acid sequence, an antibody, an antibody fragment, an FcRn-binding material, in vivo connective tissue or a derivative thereof, a nucleotide, fibronectin, transferrin, a saccharide, heparin, and elastin, but is not limited thereto. In particular, the polymer may be selected from the group consisting of a polyethylene glycol, a polypropylene glycol, an ethylene glycol-propylene glycol copolymer, polyoxyethylated polyol, polyvinyl alcohol, a polysaccharide, dextran, polyvinyl ethyl ether, a biodegradable polymer, a lipid polymer, chitin, hyaluronic acid, an oligonucleotide, and a combination thereof, but is not particularly limited thereto.

More specifically, the FcRn-binding material may be a polypeptide including an immunoglobulin Fc region, but is not particularly limited thereto. The same explanation with respect to the immunoglobulin Fc region is also applied to this aspect.

The isolated conjugate may be one in which the glucagon derivative moiety, specifically the peptide moiety including the amino acid sequence of the glucagon derivative peptide, and a biocompatible material moiety are linked with each other through a linker. The same explanation with respect to the linker is also applied to this aspect.

Additionally, the glucagon derivative moiety, specifically the peptide moiety including the amino acid sequence of the glucagon derivative peptide, may be linked to a biocompatible material moiety by a linker selected from the group consisting of a polyethylene glycol, a polypropylene glycol, an ethylene glycol-propylene glycol copolymer, polyoxyethylated polyol, polyvinyl alcohol, a polysaccharide, dextran, polyvinyl ethyl ether, a biodegradable polymer such as polylactic acid (PLA) and polylactic-glycolic acid (PLGA), lipid polymer, chitin, hyaluronic acid, fatty acid, a polymer, a low molecular weight compound, a nucleotide, and a combination thereof, but is not limited thereto.

Additionally, the biocompatible material moiety may be an FcRn-binding material, and the isolated peptide may be linked to a biocompatible material moiety by a peptide linker or a non-peptide linker selected from the group consisting of a polyethylene glycol, a polypropylene glycol, an ethylene glycol-propylene glycol copolymer, polyoxyethylated polyol, polyvinyl alcohol, a polysaccharide, dextran, polyvinyl ethyl ether, a biodegradable polymer such as polylactic acid (PLA) and polylactic-glycolic acid (PLGA), lipid polymer, chitin, hyaluronic acid, and a combination thereof, but is not limited thereto.

In particular, the FcRn-binding material may be a polypeptide including the immunoglobulin Fc region and the linker may be specifically polyethylene glycol, but is not limited thereto.

Additionally, the linker may be one that is linked to a cysteine residue of the glucagon derivative, but is not particularly limited thereto.

Additionally, the linker may be one that is respectively linked to the glucagon derivative and the biocompatible material moiety through covalent bonds, which were respectively formed when one end of the linker reacted with an amine group or thiol group of the biocompatible material moiety while the other end of the linker reacted with an amine group or thiol group of the peptide moiety, but is not particularly limited thereto.

In still another aspect, the present invention provides a method for preventing or treating congenital hyperinsulinism, hypoglycemia or metabolic syndrome, including administering the glucagon derivative, a conjugate containing the same, or a composition containing the same to a subject.

The glucagon derivative, the conjugate containing the same, composition containing the same, congenital hyperinsulinism, hypoglycemia, metabolic syndrome, prevention, and treatment are the same as explained above.

In the present invention, the term "subject" refers to those suspected of having congenital hyperinsulinism, hypoglycemia or metabolic syndrome, which means mammals including humans, mice, and livestock having congenital hyperinsulinism, hypoglycemia, or metabolic syndrome or having the risk of congenital hyperinsulinism, hypoglycemia, or metabolic syndrome. However, any subject to be treated with the glucagon derivative of the present invention or the composition containing the same is included without limitation. Further, the subject suspected of having congenital hyperinsulinism, hypoglycemia, or obesity can be effectively treated by administering with the pharmaceutical composition containing the glucagon derivative of the present invention. The congenital hyperinsulinism, hypoglycemia, and obesity are the same as explained above.

The method of the present invention may include administering the pharmaceutical composition containing the peptide at a pharmaceutically effective amount. The total daily dose should be determined within appropriate medical judgment by a physician, and administered once or several times in divided doses. Regarding the objects of the present invention, the specific therapeutically effective dose for any particular patient may be preferably applied differently, depending on various factors well known in the medical art, including the kind and degree of the response to be achieved, specific compositions including whether other agents are occasionally used therewith or not, the patient's age, body weight, general health conditions, sex and diet, the time and route of administration, secretion rate of the composition, duration of treatment, other drugs used in combination or concurrently with the composition of the present invention, and like factors well-known in the medical arts.

Meanwhile, the method for preventing or treating metabolic syndrome may be a therapy using combined administration which further contains at least one compound or material having the therapeutic activity with regard to metabolic syndrome, although the method is not particularly limited thereto.

As used herein, the term "combined administration" must be understood to refer to a simultaneous, individual, or sequential administration. When the administration is a sequential or individual administration, the interval for the administration of the secondary ingredient must be one which does not lose the advantageous effect of the combined administration.

In still another aspect, the present invention provides use of the glucagon derivative or the isolated conjugate or the composition in the preparation of a medicament (or a pharmaceutical composition) for preventing or treating congenital hyperinsulinism, hypoglycemia, or metabolic syndrome.

The glucagon derivative, the isolated conjugate, the composition, congenital hyperinsulinism, hypoglycemia, and metabolic syndrome are the same as explained above.

Hereinafter, the present invention will be described in more detail with reference to the following examples and experimental examples. However, the following examples and experimental examples are provided for illustrative purposes only, and the scope of the present invention should not be limited thereto in any manner.

Example 1

Production of Cell Line Showing cAMP Response to Glucagon

PCR was performed using a region corresponding to Open Reading Frame (ORF) in the cDNA (OriGene Technologies, Inc., USA) of human glucagon receptor gene as a template along with the following forward and reverse primers (SEQ ID NOS: 47 and 48, respectively), which include each of the EcoRI and XhoI restriction sites.

In particular, PCR was performed for a total of 30 cycles under the following conditions: 95° C. denaturation for 60 sec, annealing at 55° C. for 60 sec, and polymerization at 68° C. for 30 sec. The amplified PCR products were subjected to a 1.0% agarose gel electrophoresis and a 450 bp band was obtained by elution.

```
Forward primer (SEQ ID NO: 47):
5'-CAGCGACACCGACCGTCCCCCCGTACTTAAGGCC-3'

Reverse primer (SEQ ID NO: 48):
5'-CTAACCGACTCTCGGGGAAGACTGAGCTCGCC-3'
```

The PCR product was cloned into a known animal cell expression vector, x0GC/dhfr, to prepare a recombinant vector x0UC/GCUR.

CHO DG44 cell line cultured in DMEM/F12 (containing 10% FBS) medium was transfected with the recombinant vector xOGC/GCGR using Lipofectamine®, and cultured in a selection medium containing G418 (1 mg/mL) and methotraxate (10 nM). Single clone cell lines were selected therefrom by a limit dilution technique, and a cell line showing excellent cAMP response to glucagon in a concentration-dependent manner was finally selected therefrom.

Example 2

Synthesis of Glucagon Derivative

In order to prepare glucagon derivatives with improved physical properties, the amino acid sequence of native glucagon of SEQ ID NO: 1 was substituted with amino acid residues having positive and negative charges, and thereby glucagon derivatives were synthesized as shown in Table 1 below. The relative in vitro activities described below were measured by the method described in Example 4.

TABLE 1

Amino acid sequences of native glucagon and glucagon derivatives

| SEQ ID NO | Peptide Sequence | Ring Formation | pI | In vitro Activity (Relative Activity to SEQ ID NO: 1, %) |
|---|---|---|---|---|
| SEQ ID NO: 1 | HSQGTFTSDYSKYLDSRRAQDFVQWLMNT | — | 6.8 | 100 |
| SEQ ID NO: 2 | HSQGTFTSDYSKYLDCDRAQDFVQWLMNT | — | 4.56 | 0.6 |
| SEQ ID NO: 3 | HSQGTFTSDYSKYLDCERAQDFVQWLMNT | — | 4.66 | 6.1 |

TABLE 1-continued

Amino acid sequences of native glucagon and glucagon derivatives

| SEQ ID NO | Peptide Sequence | Ring Formation | pI | In vitro Activity (Relative Activity to SEQ ID NO: 1, %) |
|---|---|---|---|---|
| SEQ ID NO: 4 | HSQGTFTSDYSKYLDSCDAQDFVQWLMNT | — | 4.13 | <0.1 |
| SEQ ID NO: 5 | HSQGTFTSDYSKYLDSCEAQDFVQWLMNT | — | 4.22 | 0.3 |
| SEQ ID NO: 6 | HSQGTFTSDYSKYLDSCEADDFVQWLMNT | — | 4.03 | <0.1 |
| SEQ ID NO: 7 | YSQGTFTSDYSKYLDSCEADDFVQWLMNT | — | 3.71 | <0.1 |
| SEQ ID NO: 8 | YXQGTFTSDYSKYLDSCDAQDFVQWLINT | — | 3.77 | <0.1 |
| SEQ ID NO: 9 | YXQGTFTSDYSKYLDSCDAQDFVVWLINT | — | 3.77 | <0.1 |
| SEQ ID NO: 10 | YXQGTFTSDYSKYLDSCDADDFVVWLINT | — | 3.66 | <0.1 |
| SEQ ID NO: 11 | YXQGTFTSDYSKYLDEKCAKEFVQWLMNT | — | 4.78 | 4.6 |
| SEQ ID NO: 12 | YXQGTFTSDYSKYLDEKRAKEFVQWLMNTC | ring formed | 6.20 | 56.3 |
| SEQ ID NO: 13 | YXQGTFTSDYSCYLDSRRAQDFVQWLMNT | — | 4.43 | 5.2 |
| SEQ ID NO: 14 | YXQGTFTSDYSKYLDCKRAKEFVQWLMNT | — | 8.12 | 18.1 |
| SEQ ID NO: 15 | YXQGTFTSDYSKYLCEKRAQDFVVWLMNT | — | 6.11 | 1.1 |
| SEQ ID NO: 16 | YXQGTFTSDYSKYLDCRRAQVFVQWLMRT | — | 9.11 | 4.2 |
| SEQ ID NO: 17 | YXQGTFTSDYSKYLDCVRAQDFVQWLMRT | — | 6.03 | 23.2 |
| SEQ ID NO: 18 | YXQGTFTSDYSKYLDSRRACDFRLWLMNT | — | 8.15 | <0.1 |
| SEQ ID NO: 19 | YXQGTFTSDYSKYLCEKRAKEFVQWLMNT | ring formed | 8.12 | 12.1 |
| SEQ ID NO: 20 | YXQGTFTSDYSKYLDECRAKEFVQWLMNT | ring formed | 4.78 | 299.7 |
| SEQ ID NO: 21 | YXQGTFTSDYSKYLDEKCAKEFVQWLMNT | ring formed | 4.78 | 57.8 |
| SEQ ID NO: 22 | YXQGTFTSDYSKYLDEKRCKEFVQWLMNT | ring formed | 6.20 | 147.8 |
| SEQ ID NO: 23 | YXQGTFTSDYSKYCDEKRAKEFVQWLMNT | ring formed | 6.20 | 76.8 |
| SEQ ID NO: 24 | YXQGTFTSDYSKCLDEKRAKEFVQWLMNT | ring formed | 6.21 | 58.0 |
| SEQ ID NO: 25 | YXQGTFTSDYSKYLDEKRAKCFVQWLMNT | ring formed | 8.12 | 46.9 |
| SEQ ID NO: 26 | WXQGTFTSDYSKYLDECRAKDFVQWLMNT | ring formed | 4.68 | 1.0 |
| SEQ ID NO: 27 | YXQGTFVSDYSKYLDECRAKDFVQWLMNT | ring formed | 4.68 | 93.6 |
| SEQ ID NO: 28 | WXQGTFVSDYSKYLDECRAKDFVQWLMNT | ring formed | 4.68 | <0.1 |

TABLE 1-continued

Amino acid sequences of native glucagon and glucagon derivatives

| SEQ ID NO | Peptide Sequence | Ring Formation | pI | In vitro Activity (Relative Activity to SEQ ID NO: 1, %) |
|---|---|---|---|---|
| SEQ ID NO: 29 | YXQGTFTSDYSKCLDERRAKDFVQWLMNT | ring formed | 6.15 | 61.3 |
| SEQ ID NO: 30 | WXQGTFTSDYSKCLDERRAKDFVQWLMNT | ring formed | 4.44 | 0.3 |
| SEQ ID NO: 31 | YXQGTFTSDYSKYLDCKRAKEFVQWLMNT | ring formed | 8.12 | 6.3 |
| SEQ ID NO: 32 | -SQGTFTSDYSKYLDECRAKEFVQWLMNT | ring formed | 4.78 | 0.7 |
| SEQ ID NO: 33 | YXQGTFTSDYSKYLDSRRAQDFVQWLMNT | — | 6.04 | 108.2 |
| SEQ ID NO: 34 | WXQGTFTSDYSKYCDERRAKEFVQWLMNT | ring formed | 6.21 | 0.2 |
| SEQ ID NO: 35 | YXQGTFTSDYSKYCDERRAKEFVQWLMNT | ring formed | 6.2 | 17.7 |
| SEQ ID NO: 36 | YXQGTFTSDCSKYLDERRAKEFVQWLMNT | ring formed | 6.21 | 9.9 |
| SEQ ID NO: 37 | YXQGTFTSDYSKYLDERRAKEFVQWLMNTC | ring formed | 6.21 | 775.5 |
| SEQ ID NO: 38 | YXQGTFCSDYSKYLDERRAKEFVQWLMNT | ring formed | 6.15 | 167.3 |
| SEQ ID NO: 39 | YXQGTFVSDCSKYLDERRAKDFVQWLMNT | ring formed | 6.15 | 3.7 |
| SEQ ID NO: 40 | YXQGTFVSDYSKYLDERRAKDFVQWLMNTC | ring formed | 6.15 | 40.8 |
| SEQ ID NO: 41 | YXQGTFCSDYSKYLDERRAKDFVQWLMNT | ring formed | 6.03 | 45.2 |
| SEQ ID NO: 42 | YXQGTFCSDYSKYLDSRRAQDFVQWLMNT | — | 6.03 | 37.9 |
| SEQ ID NO: 43 | YXQGTFTSDCSKYLDSRRAQDFVQWLMNT | — | 6.03 | 1.6 |
| SEQ ID NO: 44 | YXQGTFTSDYSKYLDSRRAQDFVQWLMNTC | — | 6.21 | 75.4 |

In the amino acids sequences described in Table 1, the amino acid represented by X represents a non-native amino acid, aminoisobutyric acid (Aib), the underlined amino acid residues represent formation of a lactam ring between the side chains of the corresponding amino acids, and "−" in the amino acid sequence indicates that no amino acid residue is present on the corresponding position. Additionally, in the rows with regard to ring formation, "−" indicates that there is no ring formation in the corresponding sequences.

Example 3

Measurement of pI of Glucagon Derivatives

In order to measure the improved physical properties of glucagon derivatives synthesized in Example 2, pI values were calculated based on the amino acid sequences using the pI/Mw tool (expasy.org/tools/pi_tool; Gasteiger et al., 2003) in the ExPASy server.

As shown in Table 1 above, while the native glucagon of SEQ ID NO: 1 had a pI of 6.8, the some glucagon derivatives according to the present invention showed pI values in the range of from about 4 to about 6. Since the glucagon derivatives according to the present invention have pI values lower or more than that of native glucagon, they can exhibit improved solubility and higher stability at a neutral pH condition compared to native glucagon.

Accordingly, when the glucagon derivatives according to the present invention are used as a therapeutic agent for treating a target disease such as congenital hyperinsulinism, hypoglycemia, etc., they can improve patient compliance, and are also suitable for administration in combination with other anti-obesity agents or anti-diabetes agents, and thus the glucagon derivatives of the present invention can be effectively used as a therapeutic agent for treating hypoglycemia and metabolic syndromes including obesity, diabetes, nonalcoholic steatohepatitis (NASH), dyslipidemia, and coronary heart disease.

Example 4

Measurement of cAMP Activity of Glucagon Derivatives

The activities of the glucagon derivatives synthesized in Example 2 were measured in cell lines having the human glucagon receptors produced in Example 1. Specifically, the transfected cell line was subcultured 3 to 4 times a week, aliquoted into a 384-well plate in an amount of $6 \times 10^3$ cell lines/well, and cultured for 24 hours. Native glucagon and glucagon derivatives were suspended in Hank's balanced salt solution (HBSS) buffer containing 0.5 mM of 3-isobutyl-1-methylxanthine (IBMX), 0.1% bovine serum albumin (BSA), and 5 mM 4-(2-hydroxyethyl)-1-piperazineethanesulfonic acid (HEPES) with the culture cells, at concentrations of 200 nM and 1600 nM, respectively, continuously subjected into a 4-fold dilution 10 times, applied to a cAMP assay kit (LANCE cAMP 384 kit, PerkinElmer), and added to the cultured cells, and their fluorescence value was measured. Upon measurement, the highest fluorescence value was set at 100% and then $EC_{50}$ values of the glucagon derivative were calculated based on the same and compared with that of native glucagon, respectively. The results are shown in Table 1 below.

Example 5

Preparation of a Conjugate Including a Glucagon Derivative and an Immunoglobulin Fc (SEQ ID NO: 12 or 20-Immunoglobulin Fc Region Conjugate)

For the pegylation of a 10 kDa PEG having a maleimide group and an aldehyde group, respectively, at both ends (named as "maleimide-PEG-aldehyde", 10 kDa, NOF, Japan) into the cysteine residue of a glucagon derivative (SEQ ID NO: 12 or 20), the glucagon derivatives and maleimide-PEG-aldehyde were reacted at a molar ratio of 1:1 to 5, at a protein concentration of 3 mg/mL to 10 mg/mL at low temperature for 1 to 3 hours. In particular, the reaction was conducted in an environment in which 20% to 60% isopropanol was added. Upon completion of the reaction, the reactants were applied to SP sepharose HP (GE healthcare, USA) to purify the glucagon derivatives mono-pegylated on cysteine.

Then, the purified mono-pegylated glucagon derivatives and an immunoglobulin Fc were reacted at a molar ratio of 1:2 to 10, at a protein concentration of 10 mg/mL to 50 mg/mL at 4° C. to 8° C. for 12 hours to 18 hours. The reaction was conducted in an environment in which sodium cyanoborohydride (NaCNBH$_3$) and 10% to 20% isopropanol were added to 100 mM calcium phosphate buffer (pH 6.0). Upon completion of the reaction, the reactants were applied to the Butyl sepharose FF purification column (GE healthcare, USA) and Source ISO purification column (GE healthcare, USA) to purify the conjugate including the glucagon derivatives and the immunoglobulin Fc.

After preparation, the purity analyzed by reverse phase chromatography, size exclusion chromatography, and ion exchange chromatography was shown to be 95% or higher.

In particular, the conjugate in which the glucagon derivative of SEQ ID NO: 12 and an immunoglobulin Fc were linked by PEG was named as "the conjugate including the glucagon derivative of SEQ ID NO: 12 and an immunoglobulin Fc", "a long-acting conjugate of SEQ ID NO: 12", or "a long-acting derivative of SEQ ID NO: 12", and they can be used interchangeably in the present invention.

In particular, the conjugate in which the glucagon derivative of SEQ ID NO: 20 and an immunoglobulin Fc were linked by PEG was named as "a conjugate including the glucagon derivative of SEQ ID NO: 20 and an immunoglobulin Fc", "a long-acting conjugate of SEQ ID NO: 20", or "a long-acting derivative of SEQ ID NO: 20", and they can be used interchangeably in the present invention.

Example 6

Preparation of a Conjugate Including an Exendin-4 Derivative and an Immunobulin Fc A 3.4 kDa PEG having a propionaldehyde group at both ends, i.e., 3.4 k PropionALD (2) PEG, was reacted with the Lys of CA exendin-4 using imidazo-acetyl exendin-4 where the alpha carbon of N-terminal histidine was deleted (CA exendin-4, AP, USA), and the isomer peak at the rearmost part (Lys27) between the two Lys peaks, which is quite reactive and clearly distinguished from the N-terminal isomer, was separated. Subsequently, a coupling was conducted using the pegylated peptide isomer.

The coupling was conducted by reacting the above-mentioned pegylated imidazo-acetyl exendin-4 peptide and an immunoglobulin Fc at a molar ratio of 1:8, at the total protein concentration of 60 mg/mL at 4° C. for 20 hours. The reactant was 100 mM K-P (pH 6.0) and 20 mM SCB, a reducing agent, was added. The coupling reactants were purified by passing through with two purification columns. First, a large amount of immunoglobulin Fc not involved in the coupling reaction was removed using the SOURCE Q (XK-16 mL, Amersham Biosciences). Upon application of a salt gradient using 1 M NaCl at 20 mM Tris (pH 7.5) results in the immediate elution of the immunoglobulin Fc, which has a relatively weak binding affinity, followed immediately by the elution of exendin-4-immunoglobulin Fc. The immunoglobulin Fc is removed to some extent by the primary purification, however, complete separation was not achieved by ion exchange column because of the small difference in binding affinity between the immunoglobulin Fc and the exendin-4-immunoglobulin Fc. Accordingly, secondary purification was performed using the hydrophobicity of the two different materials. The sample, which passed through the primary purification, was bound to the SOURCE ISO (HR16 mL, Amersham Biosciences) using 20 mM Tris (pH 7.5) and 1.5 M ammonium sulfate, and was then eluted while the concentration of ammonium sulfate was gradually lowered. As a result, the immunoglobulin Fc, which has a weak binding affinity for the WC column, was eluted first, followed by the elution of the exendin-4-immunoglobulin Fc sample, which has a strong binding affinity, to the rear part. The separation was more easily performed compared with the ion exchange column due to the larger difference in hydrophobicity.

Column: SOURCE Q (XK 16 mL, Amersham Biosciences)
Flow rate: 2.0 mL/min
Gradient: AO→25% 70 min B (A: 20 mM Tris, pH 7.5, B: 1 MNaCl)
Column: SOURCE ISO (HR 16 mL, Amersham Biosciences)
Flow rate: 7.0 mL/min
Gradient: B 100→0% 60 min B [A: 20 mM Tris (pH 7.5), B: A+1.5 M ammonium sulfate ((NH$_4$)$_2$SO$_4$)]

The thus-prepared conjugate, in which the exendin-4 derivative and the immunoglobulin Fc region were linked by PEG, was named as "a long-acting exendin-4 derivative". Also, such term can be interchangeable used with "a long-acting exendin derivative" in the present invention.

Example 7

Preparation of a Conjugate Including a Glucagon Derivative and an Immunoglobulin Fc (SEQ ID NO: 37—Immunoglobulin Fc Region Conjugate)

For the pegylation of a 10 kDa PEG having a maleimide group and an aldehyde group, respectively, at both ends (named as "maleimide-PEG-aldehyde", 10 kDa, NOF, Japan) into the cysteine residue of a glucagon derivative (SEQ ID NO: 37), the glucagon derivatives and maleimide-PEG-aldehyde were reacted at a molar ratio of 1:1 to 5, at a protein concentration of 3 mg/mL, to 10 mg/mL at low temperature for 1 to 3 hours. In particular, the reaction was conducted in an environment in which 20% to 60% isopropanol was added. Upon completion of the reaction, the reactants were applied to SP sepharose HP (GE healthcare, USA) to purify the glucagon derivatives mono-pegylated on cysteine.

Then, the purified mono-pegylated glucagon derivatives and an immunoglobulin Fc were reacted at a molar ratio of 1:2 to 10, at a protein concentration of 10 mg/mL to 50 mg/mL at 4° C. to 8° C. for 12 hours to 18 hours. The reaction was conducted in an environment in which 10 mM to 50 mM sodium cyanoborohydride NaCNBH$_3$), which is reducing agent, and 10% to 20% isopropanol were added to 100 mM calcium phosphate buffer (pH 6.0). Upon completion of the reaction, the reactants were applied to the Butyl sepharose FF purification column (GE healthcare, USA) and Source ISO purification column (GE healthcare, USA) to purify the conjugate including the glucagon derivatives and the immunoglobulin Fc.

After preparation, the purity analyzed by reverse phase chromatography, size exclusion chromatography, and ion exchange chromatography was shown to be 95% or higher.

In particular, the conjugate in which the glucagon derivative of SEQ ID NO: 37 and an immunoglobulin Fc were linked by PEG was named as "the conjugate including the glucagon derivative of SEQ ID NO: 37 and an immunoglobulin Fc", "a long-acting conjugate of SEQ ID NO: 37", or "a long-acting derivative of SEQ ID NO: 37", and they can be interchangeably used in the present invention.

Experimental Example 1

Effect of Body Weight Reduction in Rats with High Fat Diet-Induced Obesity

In this experiment, high-fat diet-induced obesity rats, which are widely used as obesity animal models, were used. Specifically, high fat diet-induced rodents are most commonly used animal models for preclinical evaluation of the effect of obesity-treating agents in reducing body weight and the models were induced as follows. When normal rats or mice were fed with a feed having a 60% fat content for 4 weeks (rats) or 6 months (mice), the body weight of the rats showed an increase of body weight by about 600 g and the mice showed an increase of body weight by about 55 g compared to their body weight before the feeding, and the blood lipid levels also increased thus showing a state of obesity as in humans. The body weight of the rats used in this Experimental Example before administration was about 600 g. The rats were housed individually during the experiment and were given ad libitum access to water. Lighting was not provided between 6 PM and 6 AM.

The test groups fed with high-fat diet include: Group 1, with an excipient not containing long-acting glucagon (administration: 2 mL/kg; injection once every 3 days)—vehicle; Group 2, the long-acting exendin derivative of Example 6 at 3.3 nmol/kg (injection once every 3 days); Group 3, the long-acting derivative of SEQ ID NO: 12 at 1.6 nmol/kg (injection once every 3 days); Group 4, the long-acting derivative of SEQ ID NO: 12 at 3.3 nmol/kg (injection once every 3 days); Group 5, the long-acting derivative of SEQ ID NO: 12 at 6.6 nmol/kg (injection once every 3 days); Group 6, the long-acting exendin derivative of Example 6 at 3.3 nmol/kg+the long-acting derivative of SEQ ID NO: 12 at 1.6 nmol/kg (injection once every 3 days, respectively); Group 7, the long-acting exendin derivative of Example 6 at 3.3 nmol/kg+the long-acting derivative of SEQ ID NO: 12 at 3.3 nmol/kg (injection once every 3 days, respectively); Group 8, the long-acting exendin derivative of Example 6 at 3.3 nmol/kg+the long-acting derivative of SEQ ID NO: 12 at 6.6 nmol/kg (injection once every 3 days, respectively); Group 9, a paired-feeding with Group 4; and Group 10, a paired-feeding with Group 7.

The experiment was terminated on the 15$^{th}$ day, and the changes in body weight of the rats in each group were measured at 3-day intervals during the progress of the experiment. Upon termination of the experiment, the amount of mesenteric fat and liver weight were measured by autopsy. Statistical analysis was performed to compare between the excipient group (vehicle) and test groups by one-way ANOVA.

As a result of the measurement of changes in body weight, as can be confirmed in FIG. 1, the groups administered with either the long-acting exendin derivative alone or the long-acting derivative of SEQ ID NO: 12 alone showed a decrease in body weight by −8% and −7% to −22%, compared to that before administration, whereas in groups with a combined administration of the long-acting exendin derivative and the long-acting derivative of SEQ ID NO: 12, the effect of reducing body weight was improved further from −22% to −35%.

Additionally, when the effect of a body weight decrease in the group administered with the long-acting derivative of SEQ ID NO: 12 alone and the group administered with the combination of the long-acting exendin derivative and the long-acting derivative of SEQ ID NO: 12 was compared with that of the paired feeding group, respectively, a difference of about −11% and about −17% was shown, respectively, thus confirming that the body weight reducing effect was shown when administered with the glucagon derivative alone or the combined administration, by actions other than dietary intake.

That is, it was confirmed that the long-acting glucagon derivative of the present invention could play an additional role in body weight reduction in addition to the effect of anorexia.

Additionally, as a result of the measurement of the amount of mesenteric fat and liver weight, as can be confirmed in FIGS. 2 and 3, the combined administration of the long-acting exendin derivative and the long-acting derivative of SEQ ID NO: 12 showed a significant decrease in body fat and also a decrease in the weight of the liver compared to that of the group administered with an excipient. In particular, the increase/decrease of the weight of the liver is generally caused by the increase/decrease of the fat present in the liver, and the above effect of decrease in the weight of the liver shows the effect of reducing the liver fat. Accordingly, the decrease of the fat in the liver can be measured as a method for measuring the therapeutic effect of metabolic syndrome such as obesity, diabetes, nonalcoholic steatohepatitis, etc.

Experimental Example 2

Effect of Body Weight Reduction in Mice with High Fat Diet-Induced Obesity

In this experiment, high-fat diet-induced obesity mice, which are widely used as obesity animal models, were used. The body weight of the mice before administration was about 55 g. The mice were housed 7 mice per each group during the experiment and were given ad libitum access to water. Lighting was not provided between 6 PM and 6 AM.

The test groups fed with high-fat diet include: Group 1, with an excipient not containing long-acting glucagon (administration: 5 ml/kg; injection once every 2 days)—vehicle; Group 2, the long-acting exendin derivative of Example 6 at 4.3 nmol/kg (injection once every 2 days); Group 3, the long-acting derivative of SEQ ID NO: 20 at 4.4 nmol/kg (injection once every 2 days); Group 4, the long-acting derivative of SEQ ID NO: 20 at 8.8 nmol/kg (injection once every 2 days); Group 5, the long-acting exendin derivative of Example 6 at 4.3 nmol/kg+the long-acting derivative of SEQ ID NO: 20 at 4.4 nmol/kg (injection once every 2 days); Group 6, the long-acting exendin derivative of Example 6 at 2.1 nmol/kg+the long-acting derivative of SEQ ID NO: 20 at 6.6 nmol/kg (injection once every 2 days); and Group 7, the long-acting exendin derivative of Example 6 at 0.8 nmol/kg+the long-acting derivative of SEQ ID NO: 20 at 8.0 nmol/kg (injection once every 2 days).

The experiment was terminated on the $22^{nd}$ day, and the changes in body weight of the mice in each group were measured at 2-day intervals during the progress of the experiment. Upon termination of the experiment, the weight of the mouse livers was measured after autopsy.

As a result of the measurement of changes in body weight, as can be confirmed in FIG. 4, each of the groups administered with the long-acting derivative of SEQ ID NO: 20 (8.8 nmol/kg, injection once every 2 days) alone showed a decrease in body weight by −25% and −29%, respectively, compared to that before administration. Additionally, the effect of reducing body weight was shown to increase further when administered in combination with the long-acting exendin derivative. It was also confirmed that the combined administration of the long-acting exendin derivative and the long-acting derivative of SEQ ID NO: 20 at a ratio of 1:1, 1:3, and 1:10 further increased the effect of reducing body weight by −50% or higher. Additionally, the effect of reducing body weight according to the ratio between the long-acting exendin derivative and the long-acting derivative of SEQ ID NO: 20 was not significant, however, the effect of anorexia became higher along with the increase in the percentage of the long-acting exendin derivative, thus confirming that the glucagon long-acting derivative of the present invention could play an additional role in body weight reduction in addition to the effect of anorexia.

Additionally, as a result of the measurement of the total cholesterol levels in the blood, as can be confirmed in FIG. 5, each of the groups administered with the long-acting exendin derivative (4.4 nmol/kg, injection once every 2 days) and the long-acting derivative of SEQ ID NO: 20 (8.8 nmol/kg, injection once every 2 days) showed a decrease in cholesterol levels by −35% and −71%, respectively. From the above, it was confirmed that the glucagon long-acting derivative of the present invention could play an additional role in reducing blood cholesterol in addition to the effect of anorexia. Statistical analysis was performed to compare between the excipient group (vehicle) and test groups by one-way ANOVA.

Experimental Example 3

Effect of Combined Administration of Long-Acting Exendin Derivative and Long-Acting Conjugate of SEQ ID NO: 37 in Mice with High Fat Diet-Induced Obesity In this experiment, high-fat diet-induced obesity mice, which are widely used as obesity animal models, were used. The body weight of the mice before administration was about 55 g. The mice were housed 7 mice per each group during the experiment and were given ad libitum access to water. Lighting was not provided between 6 PM and 6 AM.

The test groups fed with high-fat diet include: Group 1, with an excipient not containing long-acting glucagon (administration: 5 mL/kg; injection once every 2 days)—vehicle; Group 2, of liraglutide (Novo Nordisk) at 50 nmol/kg (injection twice daily); Group 3, the long-acting exendin derivative of Example 6 at 4.3 nmol/kg (injection once every 2 days); and Group 4, the long-acting exendin derivative of Example 6 at 4.3 nmol/kg (injection once every 2 days)+the long-acting derivative of SEQ ID NO: 37 at 2.2 nmol/kg (injection once every 2 days).

The experiment was terminated on the $28^{th}$ day, and the intraperitoneal glucose tolerance test (IPGTT) was measured. The changes in body weight of the mice in each group were measured at 2-day intervals during the progress of the experiment. Upon termination of the experiment, the blood cholesterol levels and weight of the mouse livers were measured after autopsy.

As a result of the measurement of the changes in body weight, as can be confirmed in FIG. 6, each of the groups administered with liraglutide (Novo Nordisk) at 50 nmol/kg (injection twice daily) or the long-acting exendin derivative of Example 6 at 4.3 nmol/kg (injection once every 2 days) alone showed a decrease of body weight by −22% and −32% compared to that of vehicle, respectively, and the group with combined administration of the long-acting exendin derivative at 4.3 nmol/kg (injection once every 2 days)+the long-acting derivative of SEQ ID NO: 37 at 2.2 nmol/kg (injection once every 2 days) showed a further decrease of body weight by from −32% to −62% compared to that of vehicle.

The effect of reducing fat weight was also increased further in the group with combined administration of the long-acting exendin derivative at 4.3 nmol/kg (injection once every 2 days)+the long-acting derivative of SEQ ID NO: 37 at 2.2 nmol/kg (injection once every 2 days) by from −62% to −88% compared to the group with the administration of the long-acting exendin derivative at 4.3 nmol/kg (injection once every 2 days) alone.

Additionally, as a result of the measurement of the changes in the total cholesterol levels in the blood, as can be confirmed in FIG. 6, each of the groups administered with liraglutide (Novo Nordisk) at 50 nmol/kg (injection twice daily) or the long-acting exendin derivative at 4.3 nmol/kg (injection once every 2 days) alone showed a decrease of cholesterol levels by −40% and −49% compared to that of vehicle, respectively, and the group with combined administration of the long-acting exendin derivative at 4.3 nmol/kg (injection once every 2 days)+the long-acting derivative of SEQ ID NO: 37 at 2.2 nmol/kg (injection once every 2 days) showed a further decrease of cholesterol levels by from −49% to −70% compared to that of vehicle.

As a result of the measurement of the intraperitoneal glucose tolerance test (IPGTT), as shown in FIG. 6, the group with the administration of the long-acting exendin derivative at 4.3 nmol/kg (injection once every 2 days) alone and the group with combined administration of the long-acting exendin derivative at 4.3 nmol/kg (injection once every 2 days)+the long-acting derivative of SEQ ID NO: 37 at 2.2 nmol/kg (injection once every 2 days) showed similar effects of −61% and −67%, respectively.

From the above results, it was confirmed that the combined administration of the long-acting exendin derivative at 4.3 nmol/kg (injection once every 2 days)+the long-acting derivative of SEQ ID NO: 37 at 2.2 nmol/kg (injection once every 2 days) showed a similar effect with regard to the regulation of blood glucose levels while showing more excellent effect with regard to the effects of reducing body weight and blood cholesterol levels compared to that of their respective administration.

Experimental Example 4

Effect of Ameliorating Acute Hypoglycemia of Long-Acting Conjugate of SEQ ID NO: 37

SD rats were fasted for 4 hours and subcutaneously injected with insulin (0.65 U/kg) to induce hypoglycemia. Forty-five minutes after the injection, the rats were confirmed with regard to their hypoglycemia, subcutaneously injected with an excipient (2 mL/kg; single injection, vehicle), intravenously injected with a long-acting conjugate of SEQ ID NO: 37 (at concentrations of 5.16 nmol/kg, 10.31 nmol/kg, and 20.63 nmol/kg, respectively), and subcutaneously injected with native glucagon (60 nmol/kg), and the changes in blood glucose levels were measured.

As a result, it was confirmed that the long-acting conjugate of SEQ ID NO: 37 at all of the administration doses ameliorated the hypoglycemia in the SD rats induced by insulin as shown in FIG. 7. From the results, it was confirmed that the long-acting conjugate of SEQ ID NO: 37 has a therapeutic effect on hypoglycemia-related diseases.

Experimental Example 5

Effect of Ameliorating Chronic Hypoglycemia of Long-Acting Conjugate of SEQ ID NO: 37

An evaluation of the effect of the long-acting conjugate of SEQ ID NO: 37 as a therapeutic agent for congenital hyperinsulinism was conducted in rodents inserted with an insulin pump. The congenital hyperinsulinism disease model was induced by inserting the insulin pump into the rodents (rats or mice) through surgery. Since insulin is continuously secreted from the inserted pump of the rodents, persistent hypoglycemia is induced and the model is thus placed in a state similar to congenital hyperinsulinism in humans.

Specifically, SD rats were subjected to surgery of subcutaneous insertion of an osmotic pump filled with insulin. The blood glucose levels of the SD rats were measured for a week and those rats which showed persistent hypoglycemia were selected and subcutaneously injected with an excipient (vehicle) and the long-acting conjugate of SEQ ID NO: 37 (at a concentration of 3 nmol/kg or 6 nmol/kg) at 3 day intervals (Q3D) and the changes in blood glucose levels were measured for 2 weeks, and the blood glucose area under the curve ($AUC_{BG}$) was calculated.

The area under the curve (AUC) refers to a general method for quantifying the change in blood glucose levels during long-term administration of a drug. As a result, it was confirmed that the SD rats administered with the long-acting conjugate of SEQ ID NO: 37 at all of the administration doses continuously showed a significant increase in the blood glucose levels compared to those administered with the excipient not containing long-acting glucagon (2 mL/kg; once every 3 days, vehicle), which were rats with chronic hypoglycemia, as shown in FIG. 8 ($p<0.01$, *$p<0.001$ vs. chronic hypoglycemia rats, excipient, by one-way ANOVA). From the results, it was confirmed that the long-acting conjugate of SEQ ID NO: 37 has a therapeutic effect on chronic hypoglycemia that occurs in patients with congenital hyperinsulinism.

Those of ordinary skill in the art will recognize that the present invention may be embodied in other specific forms without departing from its spirit or essential characteristics. The described embodiments are to be considered in all respects only as illustrative and not restrictive. The scope of the present invention is therefore indicated by the appended claims rather than by the foregoing description. All changes which come within meaning and range of equivalency of the claims are to be embraced within the scope of the present invention.

The invention claimed is:

1. A method for treating congenital hyperinsulinism comprising administering to a subject in need thereof, an isolated conjugate comprising a peptide moiety and a biocompatible material moiety which is linked to the peptide moiety, wherein the peptide moiety comprises the amino acid sequence of the following General Formula 2:

```
                                          (SEQ ID NO: 46)
Y-Aib-QGTF-X7-SD-X10-S-X12-Y-L-X15-X16-X17-R-A-
X20-X21-F-V-X24-W-L-M-N-T-X30  General Formula 2
``` wherein
X7 is threonine (T), valine (V), or cysteine (C);
X10 is tyrosine (Y) or cysteine (C);
X12 is lysine (K) or cysteine (C);
X15 is aspartic acid (D) or cysteine (C);
X16 is glutamic acid (E) or serine (S);
X17 is lysine (K) or arginine (R);
X20 is glutamine (Q) or lysine (K);
X21 is aspartic acid (D) or glutamic acid (E);
X24 is valine (V) or glutamine (Q); and
X30 is cysteine (C) or is absent,
with the proviso that the amino acid sequence of General Formula 2 identical to SEQ ID NO: 12 is excluded.

2. A method for treating congenital hyperinsulinism comprising administering to a subject in need thereof, an isolated conjugate comprising a peptide moiety and a biocompatible material moiety which is linked to the peptide moiety, wherein the peptide moiety comprises an amino acid sequence selected from the group consisting of SEQ ID NOS: 2 to 11, 13 to 15, and 18 to 44.

3. The method of claim 1, wherein the peptide moiety comprises an amino acid sequence selected from the group consisting of SEQ ID NOS: 13, 15, and 36 to 44.

4. The method of claim 1, wherein the biocompatible material moiety is selected from the group consisting of a polymer, fatty acid, cholesterol, albumin and a fragment thereof, an albumin-binding material, a polymer of repeating units of a particular amino acid sequence, an antibody, an antibody fragment, an FcRn-binding material, in vivo connective tissue or a derivative thereof, a nucleotide, fibronectin, transferrin, a saccharide, heparin, and elastin.

5. The method of claim 4, wherein the FcRn-binding material is a polypeptide comprising an immunoglobulin Fc region.

6. The method of claim 1, wherein the peptide moiety and the biocompatible material moiety are covalently linked with each other through a linker.

7. The method of claim 6, wherein the linker is selected from the group consisting of a peptide, fatty acid, a saccharide, a polymer, a nucleotide, and a combination thereof.

8. The method of claim 7, wherein the polymer is selected from the group consisting of a polyethylene glycol, a polypropylene glycol, an ethylene glycol-propylene glycol copolymer, polyoxyethylated polyol, polyvinyl alcohol, a polysaccharide, dextran, polyvinyl ethyl ether, a biodegradable polymer, a lipid polymer, chitin, hyaluronic acid, an oligonucleotide, and a combination thereof.

9. The method of claim 5, wherein the immunoglobulin Fc region is an IgG4 Fc region.

10. The method of claim 9, wherein the immunoglobulin Fc region is an aglycosylated Fc region derived from human IgG4.

11. The method of claim 6, wherein the linker is respectively linked to the peptide moiety and the biocompatible material moiety through covalent bonds which are respectively formed by reacting one end of the linker with an amine group or thiol group of the biocompatible material moiety and reacting the other end of the linker with an amine group or thiol group of the peptide moiety.

12. The method of claim 6, wherein the linker is linked to a cysteine residue of the peptide moiety.

13. The method of claim 2, wherein the peptide moiety comprises an amino acid sequence selected from the group consisting of SEQ ID NOS: 13, 15, and 36 to 44.

14. The method of claim 2, wherein the biocompatible material moiety is selected from the group consisting of a polymer, fatty acid, cholesterol, albumin and a fragment thereof, an albumin-binding material, a polymer of repeating units of a particular amino acid sequence, an antibody, an antibody fragment, an FcRn-binding material, in vivo connective tissue or a derivative thereof, a nucleotide, fibronectin, transferrin, a saccharide, heparin, and elastin.

15. The method of claim 14, wherein the FcRn-binding material is a polypeptide comprising an immunoglobulin Fc region.

16. The method of claim 2, wherein the peptide moiety and the biocompatible material moiety are covalently linked with each other through a linker.

17. The method of claim 16, wherein the linker is selected from the group consisting of a peptide, fatty acid, a saccharide, a polymer, a nucleotide, and a combination thereof.

18. The method of claim 17, wherein the polymer is selected from the group consisting of a polyethylene glycol, a polypropylene glycol, an ethylene glycol-propylene glycol copolymer, polyoxyethylated polyol, polyvinyl alcohol, a polysaccharide, dextran, polyvinyl ethyl ether, a biodegradable polymer, a lipid polymer, chitin, hyaluronic acid, an oligonucleotide, and a combination thereof.

19. The method of claim 15, wherein the immunoglobulin Fc region is an IgG4 Fc region.

20. The method of claim 19, wherein the immunoglobulin Fc region is an aglycosylated Fc region derived from human IgG4.

21. The method of claim 16, wherein the linker is respectively linked to the peptide moiety and the biocompatible material moiety through covalent bonds which are respectively formed by reacting one end of the linker with an amine group or thiol group of the biocompatible material moiety and reacting the other end of the linker with an amine group or thiol group of the peptide moiety.

22. The method of claim 16, wherein the linker is linked to a cysteine residue of the peptide moiety.

* * * * *

SEQUENCE LISTING

<160> NUMBER OF SEQ ID NOS: 52

<210> SEQ ID NO 1
<211> LENGTH: 29
<212> TYPE: PRT
<213> ORGANISM: homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 29

<212> TYPE: PRT
<213> ORGANISM: Artificial Sequence
<220> FEATURE:
<223> OTHER INFORMATION: glucagon derivative

<400> SEQUENCE: 2

His Ser Gln Gly Thr Phe Thr Ser Asp Tyr Ser Lys Tyr Leu Asp Cys
1               5                   10                  15

Asp Arg Ala Gln Asp Phe Val Gln Trp Leu Met Asn Thr
            20                  25

<210> SEQ ID NO 3
<211> LENGTH: 29
<212> TYPE: PRT
<213> ORGANISM: Artificial Sequence
<220> FEATURE:
<223> OTHER INFORMATION: glucagon derivative

<400> SEQUENCE: 3

His Ser Gln Gly Thr Phe Thr Ser Asp Tyr Ser Lys Tyr Leu Asp Cys
1               5                   10                  15

Glu Arg Ala Gln Asp Phe Val Gln Trp Leu Met Asn Thr
            20                  25

<210> SEQ ID NO 4
<211> LENGTH: 29
<212> TYPE: PRT
<213> ORGANISM: Artificial Sequence
<220> FEATURE:
<223> OTHER INFORMATION: glucagon derivative

<400> SEQUENCE: 4

His Ser Gln Gly Thr Phe Thr Ser Asp Tyr Ser Lys Tyr Leu Asp Ser
1               5                   10                  15

Cys Asp Ala Gln Asp Phe Val Gln Trp Leu Met Asn Thr
            20                  25

<210> SEQ ID NO 5
<211> LENGTH: 29
<212> TYPE: PRT
<213> ORGANISM: Artificial Sequence
<220> FEATURE:
<223> OTHER INFORMATION: glucagon derivative

<400> SEQUENCE: 5

His Ser Gln Gly Thr Phe Thr Ser Asp Tyr Ser Lys Tyr Leu Asp Ser
1               5                   10                  15

Cys Glu Ala Gln Asp Phe Val Gln Trp Leu Met Asn Thr
            20                  25

<210> SEQ ID NO 6
<211> LENGTH: 29
<212> TYPE: PRT
<213> ORGANISM: Artificial Sequence
<220> FEATURE:
<223> OTHER INFORMATION: glucagon derivative

<400> SEQUENCE: 6

His Ser Gln Gly Thr Phe Thr Ser Asp Tyr Ser Lys Tyr Leu Asp Ser
1               5                   10                  15

Cys Glu Ala Asp Asp Phe Val Gln Trp Leu Met Asn Thr
            20                  25

<210> SEQ ID NO 7

<211> LENGTH: 29
<212> TYPE: PRT
<213> ORGANISM: Artificial Sequence
<220> FEATURE:
<223> OTHER INFORMATION: glucagon derivative

<400> SEQUENCE: 7

Tyr Ser Gln Gly Thr Phe Thr Ser Asp Tyr Ser Lys Tyr Leu Asp Ser
1               5                   10                  15

Cys Glu Ala Asp Asp Phe Val Gln Trp Leu Met Asn Thr
            20                  25

<210> SEQ ID NO 8
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 8

Tyr Xaa Gln Gly Thr Phe Thr Ser Asp Tyr Ser Lys Tyr Leu Asp Ser
1               5                   10                  15

Cys Asp Ala Gln Asp Phe Val Gln Trp Leu Ile Asn Thr
            20                  25

<210> SEQ ID NO 9
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 9

Tyr Xaa Gln Gly Thr Phe Thr Ser Asp Tyr Ser Lys Tyr Leu Asp Ser
1               5                   10                  15

Cys Asp Ala Gln Asp Phe Val Val Trp Leu Ile Asn Thr
            20                  25

<210> SEQ ID NO 10
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 10

Tyr Xaa Gln Gly Thr Phe Thr Ser Asp Tyr Ser Lys Tyr Leu Asp Ser
1               5                   10                  15

Cys Asp Ala Asp Asp Phe Val Val Trp Leu Ile Asn Thr
            20                  25

<210> SEQ ID NO 11
<211> LENGTH: 29
<212> TYPE: PRT
<213> ORGANISM: Artificial Sequence

```
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 11

Tyr Xaa Gln Gly Thr Phe Thr Ser Asp Tyr Ser Lys Tyr Leu Asp Glu
1               5                   10                  15

Lys Cys Ala Lys Glu Phe Val Gln Trp Leu Met Asn Thr
            20                  25

<210> SEQ ID NO 12
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 12

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 13
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 13

Tyr Xaa Gln Gly Thr Phe Thr Ser Asp Tyr Ser Cys Tyr Leu Asp Ser
1               5                   10                  15

Arg Arg Ala Gln Asp Phe Val Gln Trp Leu Met Asn Thr
            20                  25

<210> SEQ ID NO 14
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 14

Tyr Xaa Gln Gly Thr Phe Thr Ser Asp Tyr Ser Lys Tyr Leu Asp Cys
1               5                   10                  15

Lys Arg Ala Lys Glu Phe Val Gln Trp Leu Met Asn Thr
            20                  25
```

```
<210> SEQ ID NO 15
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 15

Tyr Xaa Gln Gly Thr Phe Thr Ser Asp Tyr Ser Lys Tyr Leu Cys Glu
1               5                   10                  15

Lys Arg Ala Gln Asp Phe Val Val Trp Leu Met Asn Thr
            20                  25

<210> SEQ ID NO 16
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 16

Tyr Xaa Gln Gly Thr Phe Thr Ser Asp Tyr Ser Lys Tyr Leu Asp Cys
1               5                   10                  15

Arg Arg Ala Gln Val Phe Val Gln Trp Leu Met Arg Thr
            20                  25

<210> SEQ ID NO 17
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 17

Tyr Xaa Gln Gly Thr Phe Thr Ser Asp Tyr Ser Lys Tyr Leu Asp Cys
1               5                   10                  15

Val Arg Ala Gln Asp Phe Val Gln Trp Leu Met Arg Thr
            20                  25

<210> SEQ ID NO 18
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 18

Tyr Xaa Gln Gly Thr Phe Thr Ser Asp Tyr Ser Lys Tyr Leu Asp Ser
1               5                   10                  15

Arg Arg Ala Cys Asp Phe Arg Leu Trp Leu Met Asn Thr
            20                  25
```

<210> SEQ ID NO 19
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 19

Tyr Xaa Gln Gly Thr Phe Thr Ser Asp Tyr Ser Lys Tyr Leu Cys Glu
1               5                   10                  15

Lys Arg Ala Lys Glu Phe Val Gln Trp Leu Met Asn Thr
            20                  25

<210> SEQ ID NO 20
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 20

Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Met Asn Thr
            20                  25

<210> SEQ ID NO 21
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 21

Tyr Xaa Gln Gly Thr Phe Thr Ser Asp Tyr Ser Lys Tyr Leu Asp Glu
1               5                   10                  15

Lys Cys Ala Lys Glu Phe Val Gln Trp Leu Met Asn Thr
            20                  25

<210> SEQ ID NO 22
<211> LENGTH: 29
<212> TYPE: PRT
<213> ORGANISM: Artificial Sequence
<220> FEATURE:

```
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 22

Tyr Xaa Gln Gly Thr Phe Thr Ser Asp Tyr Ser Lys Tyr Leu Asp Glu
1               5                   10                  15

Lys Arg Cys Lys Glu Phe Val Gln Trp Leu Met Asn Thr
            20                  25

<210> SEQ ID NO 23
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 23

Tyr Xaa Gln Gly Thr Phe Thr Ser Asp Tyr Ser Lys Tyr Cys Asp Glu
1               5                   10                  15

Lys Arg Ala Lys Glu Phe Val Gln Trp Leu Met Asn Thr
            20                  25

<210> SEQ ID NO 24
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 24

Tyr Xaa Gln Gly Thr Phe Thr Ser Asp Tyr Ser Lys Cys Leu Asp Glu
1               5                   10                  15

Lys Arg Ala Lys Glu Phe Val Gln Trp Leu Met Asn Thr
            20                  25

<210> SEQ ID NO 25
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
```

-continued

<222> LOCATION: (16)..(20)
<223> OTHER INFORMATION: amino acids at positions 16 and 20 form a ring

<400> SEQUENCE: 25

Tyr Xaa Gln Gly Thr Phe Thr Ser Asp Tyr Ser Lys Tyr Leu Asp Glu
1               5                   10                  15
Lys Arg Ala Lys Cys Phe Val Gln Trp Leu Met Asn Thr
            20                  25

<210> SEQ ID NO 26
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 26

Trp Xaa Gln Gly Thr Phe Thr Ser Asp Tyr Ser Lys Tyr Leu Asp Glu
1               5                   10                  15
Cys Arg Ala Lys Asp Phe Val Gln Trp Leu Met Asn Thr
            20                  25

<210> SEQ ID NO 27
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 27

Tyr Xaa Gln Gly Thr Phe Val Ser Asp Tyr Ser Lys Tyr Leu Asp Glu
1               5                   10                  15
Cys Arg Ala Lys Asp Phe Val Gln Trp Leu Met Asn Thr
            20                  25

<210> SEQ ID NO 28
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 28

Trp Xaa Gln Gly Thr Phe Val Ser Asp Tyr Ser Lys Tyr Leu Asp Glu
1               5                   10                  15

```
Cys Arg Ala Lys Asp Phe Val Gln Trp Leu Met Asn Thr
            20                  25

<210> SEQ ID NO 29
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 29

Tyr Xaa Gln Gly Thr Phe Thr Ser Asp Tyr Ser Lys Cys Leu Asp Glu
1               5                   10                  15

Arg Arg Ala Lys Asp Phe Val Gln Trp Leu Met Asn Thr
            20                  25

<210> SEQ ID NO 30
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 30

Trp Xaa Gln Gly Thr Phe Thr Ser Asp Tyr Ser Lys Cys Leu Asp Glu
1               5                   10                  15

Arg Arg Ala Lys Asp Phe Val Gln Trp Leu Met Asn Thr
            20                  25

<210> SEQ ID NO 31
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (17)..(21)
<223> OTHER INFORMATION: amino acids at positions 17 and 21 form a ring

<400> SEQUENCE: 31

Tyr Xaa Gln Gly Thr Phe Thr Ser Asp Tyr Ser Lys Tyr Leu Asp Cys
1               5                   10                  15

Lys Arg Ala Lys Glu Phe Val Gln Trp Leu Met Asn Thr
            20                  25

<210> SEQ ID NO 32
<211> LENGTH: 28
```

```
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (15)..(19)
<223> OTHER INFORMATION: amino acids at positions 15 and 19 form a ring

<400> SEQUENCE: 32

Ser Gln Gly Thr Phe Thr Ser Asp Tyr Ser Lys Tyr Leu Asp Glu Cys
1               5                   10                  15

Arg Ala Lys Glu Phe Val Gln Trp Leu Met Asn Thr
            20                  25

<210> SEQ ID NO 33
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 33

Tyr Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 34
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 34

Trp Xaa Gln Gly Thr Phe Thr Ser Asp Tyr Ser Lys Tyr Cys Asp Glu
1               5                   10                  15

Arg Arg Ala Lys Glu Phe Val Gln Trp Leu Met Asn Thr
            20                  25

<210> SEQ ID NO 35
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 35
```

Tyr Xaa Gln Gly Thr Phe Thr Ser Asp Tyr Ser Lys Tyr Cys Asp Glu
1               5                   10                  15

Arg Arg Ala Lys Glu Phe Val Gln Trp Leu Met Asn Thr
            20                  25

<210> SEQ ID NO 36
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 36

Tyr Xaa Gln Gly Thr Phe Thr Ser Asp Cys Ser Lys Tyr Leu Asp Glu
1               5                   10                  15

Arg Arg Ala Lys Glu Phe Val Gln Trp Leu Met Asn Thr
            20                  25

<210> SEQ ID NO 37
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 37

Tyr Xaa Gln Gly Thr Phe Thr Ser Asp Tyr Ser Lys Tyr Leu Asp Glu
1               5                   10                  15

Arg Arg Ala Lys Glu Phe Val Gln Trp Leu Met Asn Thr Cys
            20                  25                  30

<210> SEQ ID NO 38
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 38

Tyr Xaa Gln Gly Thr Phe Cys Ser Asp Tyr Ser Lys Tyr Leu Asp Glu
1               5                   10                  15

Arg Arg Ala Lys Glu Phe Val Gln Trp Leu Met Asn Thr
            20                  25

```
<210> SEQ ID NO 39
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 39

Tyr Xaa Gln Gly Thr Phe Val Ser Asp Cys Ser Lys Tyr Leu Asp Glu
1               5                   10                  15

Arg Arg Ala Lys Asp Phe Val Gln Trp Leu Met Asn Thr
            20                  25

<210> SEQ ID NO 40
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 40

Tyr Xaa Gln Gly Thr Phe Val Ser Asp Tyr Ser Lys Tyr Leu Asp Glu
1               5                   10                  15

Arg Arg Ala Lys Asp Phe Val Gln Trp Leu Met Asn Thr Cys
            20                  25                  30

<210> SEQ ID NO 41
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 41

Tyr Xaa Gln Gly Thr Phe Cys Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 42
<211> LENGTH: 29
<212> TYPE: PRT
<213> ORGANISM: Artificial Sequence
<220> FEATURE:
<223> OTHER INFORMATION: glucagon derivative
<220> FEATURE:
```

```
<221> NAME/KEY: MISC_FEATURE
<222> LOCATION: (2)
<223> OTHER INFORMATION: Xaa is aminoisobutyric acid (Aib)

<400> SEQUENCE: 42

Tyr Xaa Gln Gly Thr Phe Cys Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 43
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 43

Tyr Xaa Gln Gly Thr Phe Thr Ser Asp Cys Ser Lys Tyr Leu Asp Ser
1               5                   10                  15

Arg Arg Ala Gln Asp Phe Val Gln Trp Leu Met Asn Thr
            20                  25

<210> SEQ ID NO 44
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 44

Tyr Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Cys
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (1)
<223> OTHER INFORMATION: Xaa is histidine, desamino-histidyl,
      N-dimethyl-histidyl, beta-hydroxy imidazopropionyl,
      4-imidazoacetyl, beta-carboxy imidazopropionyl, tryptophan, or
      tyrosine, or is absent
<220> FEATURE:
<221> NAME/KEY: MISC_FEATURE
<222> LOCATION: (2)
<223> OTHER INFORMATION: Xaa is alpha-methyl-glutamic acid,
      aminoisobutyric acid (Aib), D-alanine, glycine, Sar
      (N-methylglycine), serine, or D-serine
<220> FEATURE:
<221> NAME/KEY: MISC_FEATURE
<222> LOCATION: (7)
<223> OTHER INFORMATION: Xaa is threonine, valine, or cysteine
<220> FEATURE:
<221> NAME/KEY: MISC_FEATURE
<222> LOCATION: (10)
```

```
<223> OTHER INFORMATION: Xaa is tyrosine or cysteine
<220> FEATURE:
<221> NAME/KEY: MISC_FEATURE
<222> LOCATION: (12)
<223> OTHER INFORMATION: Xaa is lysine or cysteine
<220> FEATURE:
<221> NAME/KEY: MISC_FEATURE
<222> LOCATION: (13)
<223> OTHER INFORMATION: Xaa is tyrosine or cysteine
<220> FEATURE:
<221> NAME/KEY: MISC_FEATURE
<222> LOCATION: (14)
<223> OTHER INFORMATION: Xaa is leucine or cysteine
<220> FEATURE:
<221> NAME/KEY: MISC_FEATURE
<222> LOCATION: (15)
<223> OTHER INFORMATION: Xaa is aspartic acid, glutamic acid, or
      cysteine
<220> FEATURE:
<221> NAME/KEY: MISC_FEATURE
<222> LOCATION: (16)
<223> OTHER INFORMATION: Xaa is glutamic acid, aspartic acid, serine,
      alpha-methyl-glutamic acid, or cysteine, or is absent
<220> FEATURE:
<221> NAME/KEY: MISC_FEATURE
<222> LOCATION: (17)
<223> OTHER INFORMATION: Xaa is aspartic acid, glutamine, glutamic acid,
      lysine, arginine, serine, cysteine, or valine, or is absent
<220> FEATURE:
<221> NAME/KEY: MISC_FEATURE
<222> LOCATION: (18)
<223> OTHER INFORMATION: Xaa is alanine, aspartic acid, glutamic acid,
      arginine, valine, or cysteine, or is absent
<220> FEATURE:
<221> NAME/KEY: MISC_FEATURE
<222> LOCATION: (19)
<223> OTHER INFORMATION: Xaa is alanine, arginine, serine, valine, or
      cysteine, or is absent
<220> FEATURE:
<221> NAME/KEY: MISC_FEATURE
<222> LOCATION: (20)
<223> OTHER INFORMATION: Xaa is lysine, histidine, glutamine, aspartic
      acid, lysine, arginine, alpha-methyl-glutamic acid, or cysteine,
      or is absent
<220> FEATURE:
<221> NAME/KEY: MISC_FEATURE
<222> LOCATION: (21)
<223> OTHER INFORMATION: Xaa is aspartic acid, glutamic acid, leucine,
      valine, or cysteine, or is absent
<220> FEATURE:
<221> NAME/KEY: MISC_FEATURE
<222> LOCATION: (23)
<223> OTHER INFORMATION: Xaa is isoleucine, valine, or arginine, or is
      absent
<220> FEATURE:
<221> NAME/KEY: MISC_FEATURE
<222> LOCATION: (24)
<223> OTHER INFORMATION: Xaa is valine, arginine, alanine, cysteine,
      glutamic acid, lysine, glutamine, alpha-methyl-glutamic acid, or
      leucine, or is absent;
<220> FEATURE:
<221> NAME/KEY: MISC_FEATURE
<222> LOCATION: (27)
<223> OTHER INFORMATION: Xaa is isoleucine, valine, alanine, lysine,
      methionine, glutamine, or arginine, or is absent
<220> FEATURE:
<221> NAME/KEY: MISC_FEATURE
<222> LOCATION: (28)
<223> OTHER INFORMATION: Xaa is glutamine, lysine, asparagine, or
      arginine, or is absent
<220> FEATURE:
<221> NAME/KEY: MISC_FEATURE
<222> LOCATION: (29)
<223> OTHER INFORMATION: Xaa is lysine, alanine, glycine, or threonine,
      or is absent
<220> FEATURE:
<221> NAME/KEY: MISC_FEATURE
<222> LOCATION: (30)
<223> OTHER INFORMATION: Xaa is cysteine, or is absent
```

<400> SEQUENCE: 45

Xaa Xaa Gln Gly Thr Phe Xaa Ser Asp Xaa Ser Xaa Xaa Xaa Xaa
1               5                   10                  15

Xaa Xaa Xaa Xaa Xaa Phe Xaa Xaa Trp Leu Xaa Xaa Xaa Xaa
            20                  25                  30

<210> SEQ ID NO 46
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (7)
<223> OTHER INFORMATION: Xaa is threonine, valine, or cysteine
<220> FEATURE:
<221> NAME/KEY: MISC_FEATURE
<222> LOCATION: (10)
<223> OTHER INFORMATION: Xaa is tyrosine or cysteine
<220> FEATURE:
<221> NAME/KEY: MISC_FEATURE
<222> LOCATION: (12)
<223> OTHER INFORMATION: Xaa is lysine or cysteine
<220> FEATURE:
<221> NAME/KEY: MISC_FEATURE
<222> LOCATION: (15)
<223> OTHER INFORMATION: Xaa is aspartic acid or cysteine
<220> FEATURE:
<221> NAME/KEY: MISC_FEATURE
<222> LOCATION: (16)
<223> OTHER INFORMATION: Xaa is glutamic acid or serine
<220> FEATURE:
<221> NAME/KEY: MISC_FEATURE
<222> LOCATION: (17)
<223> OTHER INFORMATION: Xaa is lysine or arginine
<220> FEATURE:
<221> NAME/KEY: MISC_FEATURE
<222> LOCATION: (20)
<223> OTHER INFORMATION: Xaa is glutamine or lysine
<220> FEATURE:
<221> NAME/KEY: MISC_FEATURE
<222> LOCATION: (21)
<223> OTHER INFORMATION: Xaa is aspartic acid or glutamic acid
<220> FEATURE:
<221> NAME/KEY: MISC_FEATURE
<222> LOCATION: (24)
<223> OTHER INFORMATION: Xaa is valine or glutamine
<220> FEATURE:
<221> NAME/KEY: MISC_FEATURE
<222> LOCATION: (30)
<223> OTHER INFORMATION: Xaa is cysteine or is absent

<400> SEQUENCE: 46

Tyr Xaa Gln Gly Thr Phe Xaa Ser Asp Xaa Ser Xaa Tyr Leu Xaa Xaa
1               5                   10                  15

Xaa Arg Ala Xaa Xaa Phe Val Xaa Trp Leu Met Asn Thr Xaa
            20                  25                  30

<210> SEQ ID NO 47
<211> LENGTH: 34
<212> TYPE: DNA
<213> ORGANISM: Artificial Sequence
<220> FEATURE:
<223> OTHER INFORMATION: forward primer

<400> SEQUENCE: 47

```
cagcgacacc gaccgtcccc ccgtacttaa ggcc                              34
```

<210> SEQ ID NO 48
<211> LENGTH: 32
<212> TYPE: DNA
<213> ORGANISM: Artificial Sequence
<220> FEATURE:
<223> OTHER INFORMATION: reverse primer

<400> SEQUENCE: 48

```
ctaaccgact ctcggggaag actgagctcg cc                               32
```

<210> SEQ ID NO 49
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid

<400> SEQUENCE: 49

Tyr Xaa Gln Gly Thr Phe Thr Ser Asp Tyr Ser Cys Tyr Leu Asp Glu
1               5                   10                  15

Lys Arg Ala Lys Glu Phe Val Gln Trp Leu Met Asn Thr
            20                  25

<210> SEQ ID NO 50
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid

<400> SEQUENCE: 50

Tyr Xaa Gln Gly Thr Phe Thr Ser Asp Tyr Ser Lys Tyr Leu Cys Glu
1               5                   10                  15

Lys Arg Ala Gln Asp Phe Val Gln Trp Leu Met Asn Thr
            20                  25

<210> SEQ ID NO 51
<211> LENGTH: 4
<212> TYPE: PRT
<213> ORGANISM: Artificial Sequence
<220> FEATURE:
<223> OTHER INFORMATION: linker sequence

<400> SEQUENCE: 51

Gly Gly Gly Ser
1

<210> SEQ ID NO 52
<211> LENGTH: 5
<212> TYPE: PRT
<213> ORGANISM: Artificial Sequence
<220> FEATURE:
<223> OTHER INFORMATION: linker sequence

```
<400> SEQUENCE: 52

Gly Gly Gly Gly Ser
1               5
```